United States Patent [19]

Matsumura et al.

[11] Patent Number: 5,243,051
[45] Date of Patent: Sep. 7, 1993

[54] TETRAHYDROPYRIDINE DERIVATIVES

[75] Inventors: Hiromu Matsumura; Toshisada Yano, both of Hyogo; Hiroshi Hashizume, Osaka; Akira Matsushita, Hyogo; Masami Eigyo, Nara, all of Japan

[73] Assignee: Shionigi & Co., Ltd., Osaka, Japan

[21] Appl. No.: 903,924

[22] Filed: Jun. 26, 1992

Related U.S. Application Data

[62] Division of Ser. No. 655,585, Feb. 15, 1991, Pat. No. 5,149,817.

[30] Foreign Application Priority Data

Mar. 5, 1990 [JP] Japan .................. 2-54220

[51] Int. Cl.$^5$ .......................... C07D 31/535
[52] U.S. Cl. .................. 544/124; 544/131; 544/333; 544/60; 544/360; 546/148; 546/165; 546/166; 546/281; 546/273; 546/272; 546/329; 546/278
[58] Field of Search ............... 544/124, 131

[56] References Cited

U.S. PATENT DOCUMENTS

| | | | |
|---|---|---|---|
| 4,006,232 | 2/1977 | Hayau et al. | 514/392 |
| 4,012,374 | 3/1977 | Wade et al. | 540/524 |
| 4,487,773 | 12/1984 | Temple, Jr. et al. | 544/295 |
| 4,977,167 | 12/1990 | Matsumura et al. | 514/326 |

FOREIGN PATENT DOCUMENTS 0304330 2/1989 European Pat. Off. .

OTHER PUBLICATIONS

CA 88:105311x Hasegawa (1978).

*Primary Examiner*—Jane T. Fan
*Attorney, Agent, or Firm*—Wenderoth, Lind & Ponack

[57] ABSTRACT

The present invention relates to tetrahydropyridine derivatives which have high affinity and specificity to $\sigma$ receptors, whereby these compounds are thought to be effective for treatment of some psychoses.

2 Claims, No Drawings

TETRAHYDROPYRIDINE DERIVATIVES

This is a divisional application of Ser. No. 07/655585 filed Feb. 15, 1991, now U.S. Pat. No. 5,149,817, issued Sep. 22, 1992.

BACKGROUND OF THE INVENTION

1. Field of the Invention

The present invention relates to novel tetrahydropyridine derivatives with psychotropic activities.

2. Prior Art

Antidopamine agents such as haloperidol (U.S. Pat. No. 3,438,991) are used as an antipsychotic agent. Adverse reactions in the extrapyramidal tract such as delayed dyskinesia are caused by them during long-term therapy. Recently, safer drugs, rimcazole (JP. Pat. Publn. No. 55-64,585) and BMY 148021 (GB Patent No. 2,155, 925), which show high affinity to $\sigma$ receptors but low affinity to dopamine receptors, have been developed as psychotropic drugs. On the other hand, the exsistence of a binding site of dextromethorphan (DM) in the central nervous system has been reported (J. Musacchio, M. Klein and L. J. Santiago, The Journal of Pharmacology and Therapeutics 247 (2), 424 (1988), High Affinity Dextromethorphan Binding Sites in Guinea Pig Brain; Further Characterization and Allosteric Interactions). DM, which is one of the most popular antitussives, is thought to be effective for ischemic encephalopathy (F. C. Tortella, M. Pellicano and N. G. Bowery, Trips, 10(12), 501 (1989), Dextromethophan and neuromodulation: old drug coughs up new activities). It is also thought that the property of $\sigma$ receptors, which is labeled with [3H]3PPP adopted in the present invention, resembles that of the DM binding site (J. M. Musacchio, M. Klein and P. D. Cano 11, Life Sciences, 45, 1721 (1989), Dextromethorphan and Sigma Ligands: Common Sites but Diverse Effects).

SUMMARY OF THE INVENTION

This invention relates to novel tetrahydropyridine derivatives with psychotropic activities. Furthermore, these compounds have high affinity and specificity to $\sigma$ receptors, whereby they are thought to be effective for some psychoses such as depression, mania, and acute and chronic schizophrenia, and cerebral ischemic disease.

DETAILED DESCRIPTION

The present invention relates to compounds of the formula:

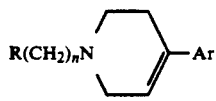

wherein Ar is phenyl or thienyl which may have identically or differently one or two substituents selected from the group consisting of lower alkyl, lower alkoxy, halogen, substituted or unsubstituted phenyl, trifluoromethyl, and hydroxy; n is an integer of from 2 to 6; R is hydroxy or a group of the formula:

$$R^2R^3N(CO)_p(NR^1)_q-$$

or

wherein $R^1$ is hydrogen or lower alkyl; $R^2$ and $R^3$ each is hydrogen or lower alkyl or taken together with the adjacent nitrogen atom may form a 5- or 6-membered heterocyclic group, which may be condensed with a benzene ring, where the heterocyclic group may have identically or differently 1 to 3 substituents selected from the group consisting of lower alkyl, halogen, oxo, pyrimidine, and substituted or unsubstituted phenyl; $R^4$ is NH, O, or a single bond; $X^1$ and $X^2$ each is hydrogen, lower alkyl, halogen, or hydroxy; p and q each is an integer of 0 or 1, excluding the case here p is 0 when q is 1, or a pharmaceutically acceptable acid addition salt thereof.

In this specification, the term "lower alkyl" refers to a straight or branched chain $C_1$ to $C_6$ alkyl including methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl and the like.

The term "lower alkoxy" refers to $C_1$ to $C_6$ alkoxy including methoxy, ethoxy, propoxy, butoxy, pentyloxy, hexyloxy and the like.

The term "halogen" refers to fluorine, chlorine, bromine, and iodine.

"Substituted phenyl" means phenyl substituted by one or more substituents, of which examples are hydroxy, lower alkyl, lower alkoxy, and halogen.

The "5- or 6-membered heterocyclic group" may contain one or more additional heteroatoms including oxygen, sulfur, and nitrogen atoms, and examples of the 5- or 6-membered heterocyclic group are isothiazole, pyrozole, pyridine, pyrimidine, imidazole, and isoxazole, preferably, pyrrolidine, piperidine, piperazine, imidazolidine, thiomorpholine, morpholine, pyrazolidine, and the like. The above mentioned heterocyclic group may be condensed with a benzene ring at any position. Further they may have identically or differently 1 to 3 substituents selected from the group consisting of lower alkyl, halogen, oxo, pyrimidine, and substituted or unsubstituted phenyl.

Pharmaceutically acceptable acid addition salts include mineral acid salts such as hydrocloride, sulfate, nitrate, and phosphate, and organic acid salt such as acetate, fumarate, citrate, tartarate, maleate, and oxalate, most preferably hydrochloride, maleate and oxalate.

The compounds of this invention can be prepared by the following method.

METHOD A

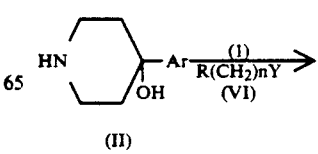

-continued

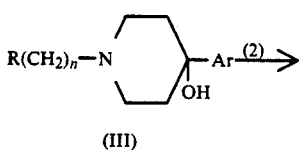

(III)

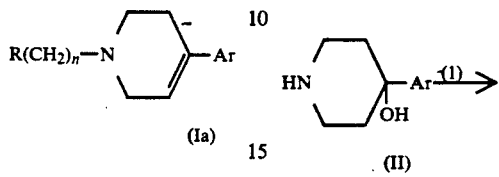

(Ia)

METHOD B

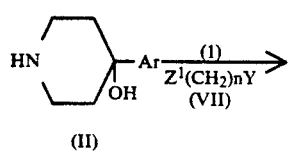

(II)

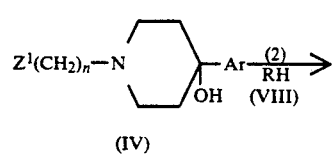

(IV)

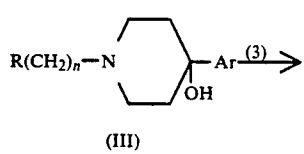

(III)

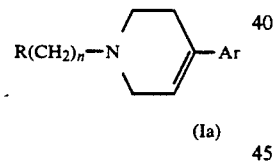

(Ia)

METHOD C

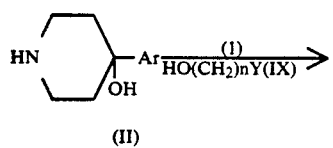

(II)

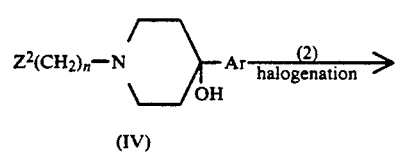

(IV)

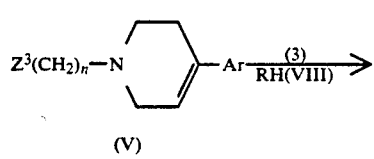

(V)

-continued

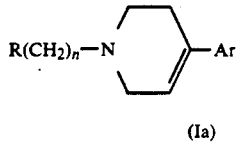

(Ia)

METHOD D

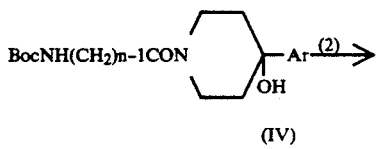

(II)

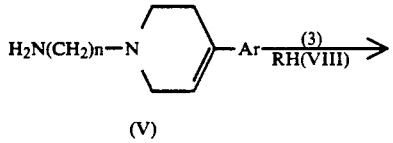

(IV)

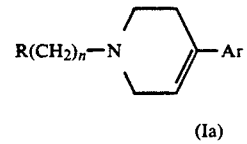

(V)

(Ia)

wherein Ar, R, $X^1$, $X^2$, and n each has the same meaning as defined above, Y means halogen, $Z^1$ means phthaloyl or halogen, $Z^2$ and $Z^3$ each means halogen, hydroxy, alkoxy, or carbonyl,

METHOD A

Step 1

The compound (II) is reacted with the compound of the formula:

R(CH$_2$)nY      (VI)

wherein R, Y, and n each has the same meaning as defined above in an appropriate organic solvent, if necessary in the presence of base to prepare the compound (III).

The reaction is performed at a temperature of from 50° to 200° C., preferably from 85° to 120° C., for 1-15 hours, especially for 5-10 hours.

Organic solvents which may be used are alcohols such as methanol and ethanol, ethers such as diethylether and tetrahydrofuran, dimethylformamide, acetonitrile and the like, most preferably dimethylformamide.

As the base, sodium hydroxide, potassium hydroxide, calcium hydroxide, potassium carbonate, pyridine, triethylamine, and the like may be used.

Step 2

The compound (III) is subjected to dehydration in an organic solvent in the presence of the acid to prepare the compound (I a).

The reaction is performed at a temperature of from 0° to 120° C., preferably at room temperature for 1-96 hours, especially for 3-72 hours.

The same organic solvent as mentioned in Step 1 may be used.

The acid includes hydrochloride, acetic acid, trifluoroacetic acid and p-toluenesulfonic acid.

METHOD B

Step 1

The compound (II) is reacted with the compound of the formula:

$$Z^1(CH_2)_nY \qquad (VII)$$

wherein $Z^1Y$ and n each has the same meaning as defined above in an organic solvent in the presence of a base to prepare the compound (IV).

The reaction is performed at 10°-150° C., preferably from room temperature to 110° C., for 1-20 hours, especially for 3-7 hours.

The same organic solvent and the base as mentioned Method A (step 1) may be used.

The compound (VII) means phthalimide butylbromide, 3-bromo-1-chloropropane and the like.

Step 2

The compound (IV) is reacted with the compound of the formula:

$$RH \qquad (VIII)$$

wherein R has the same meaning as defined above in an organic solvent, if necessary in the presence of base to prepare the compound (III).

The reaction is performed at 80°-200° C., preferably at 100°-130° C., for 1-24 hours, especially for 2-7 hours.

The same organic solvent and the base as mentioned Step 1 may be used.

Step 3

The compound (III) is subjected to dehydration in the same manner as Method A (step 2) to prepare the compound (Ia). Each condition is the same as Method A (step 2).

METHOD C

Step 1

The compound (II) is reacted with the compound of the formula:

$$HO(CH_2)_nY \qquad (IX)$$

wherein Y and n each has the same meaning as defined above, preferably in the presence of the base to prepare the compound (IV).

The reaction is performed at 50°-200° C., preferably at 120°-150° C., for 3-20 hours, especially for 5-9 hours.

Step 2

The compound (IV) is reacted with a chloride of a nonmetal element to prepare the compound (V).

The reaction is performed at 0°-100° C., preferably at room temperature, for 1-48 hours, especially for 2-24 hours.

The chloride includes sulfur chloride, thionylchloride, hydrochloride, carbon tetrachloride, and the like.

Step 3

The compound (V) is reacted with RH (VIII) to prepare the compound (III).

The reaction is performed at 0°-100° C., preferably from room temperature to 50° C. for 1-96 hours, preferably for 3-72 hours.

Step 4

The compound (III) is subjected to dehydration in the same manner as Method A (step 2) to prepare the compound (Ia).

METHOD D

Step 1

The compound (II) is reacted with N-protected-β-alanine, in the presence of condensing agent such as 1,3-dicyclohexylcarbodiimide, and 1-hydroxybenzotriazole in an appropriate organic solvent to prepare the compound (IV).

The reaction is performed at a temperature of from 10° to 150° C., preferably from room temperature to 70° C., for 1-20 hours, especially for 3-7 hours.

The same organic solvent as mentioned in METHOD A (Step 1) may be used.

Step 2

The compound (IV) is reacted in an appropriate solvent to remove the amino-protecting group. Then the obtained compound is subjected to a reduction reaction in the presence of a reductant.

The former reaction is performed at a temperature of from 10° to 150° C., preferably from room temperature to 70° C., for 1-20 hours, especially for 3-7 hours.

The same organic solvent as mentioned in METHOD A (Step 1) may be used, most preferably trifluoroacetic acid.

The latter reduction reaction is performed in an ordinary method in the presence of the reductant such as lithium aluminium hydride, hydro iodide, hydrogen sulfide, and sodium iodide at a temperature of from 0° and 100° C., preferably room temperature, for 1 to 7 hours, especially for 2 to 4 hours.

Step 3

The compound (V) is reacted with RH (VIII) to prepare the compound (Ia).

The reaction is performed at a temperature of from 50° to 200° C., preferably from 100° to 130° C., for 30 minutes to 5 hours, especially for 1-3 hours.

The compound of the present invention can be administered orally or parenterally. For example, the compound of the present invention may be orally administered in the form of tablets, powders, capsules, and granules, or liquid form such as syrup or elixir, and parenterally in the form of injection of an aqueous or oily suspension.

These preparations can be prepared in a conventional manner by using excipients, binders, lubricants, aqueous or oily solubilizers, emulsifier, suspending agents, and the like. And further additives such as preservatives and stabilizers can be used.

The dosages may be varied depending upon the administration route age, weight and condition of the patient, and the kind of disease but is, usually 5-1000 mg/day, preferably 20-200 mg/day through the oral route, and 1-500 mg/day, preferably 5-50 mg/day through the parenteral route in a single or divided doses.

The present invention is illustrated by the following examples and reference examples, which are not to be considered as limiting.

The abbreviations used in examples and reference examples have the following meanings.

Me: methyl, Et: ethyl, t-Bu: tert-butyl, iPr: isopropyl, Ph: phenyl, Ts: tosyl DMF: dimethylformamide, aq.: aqueous

EXAMPLE 1

1-[3-{4-(3,4-dichlorophenyl)-1,2,5,6-tetrahydropyridin-1-yl}-propylcarbamoyl]-2-oxopyrrolidine (I a-1)

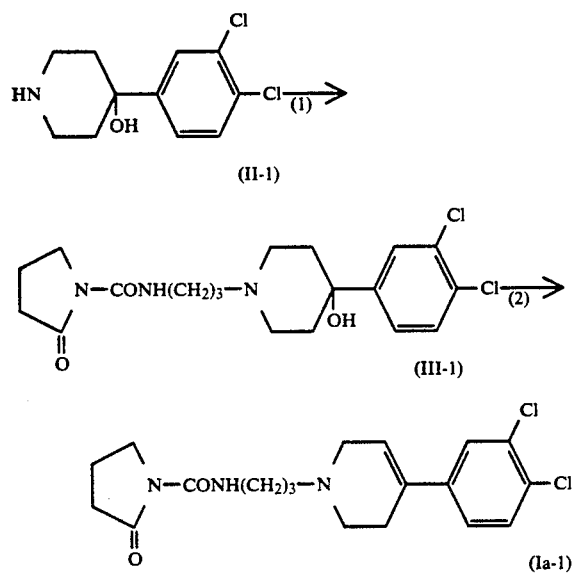

(1) A solution of 3.0 g of 4-hydroxy-4-(3,4-dichlorophenyl)piperidine (II-1) and 2.50 g of 1{(3-chloropropyl)carbamoyl-2-oxopyrrolidine in 35 ml of DMF is stirred at 105°-110° C. for 6 hours in the presence of 2.74 g of NaI and 4.22 g of $K_2CO_3$ (reaction condition 1). The reaction mixture is poured into ice-water, and the solution is extracted with ethyl acetate. The organic layer is washed with water, dried over $MgSO_4$ and concentrated under reduced pressure. The obtained oily substance is subjected to column chromatography with silica gel; eluting with methylene chloride/methanol (15/1-10/1 v/v) to prepare 4.20 g of the objective compound (III-1) as colorless needles. mp.: 135.5°-137.0° C.

Anal Calcd. (%) for $C_{19}H_{25}N_3O_3Cl_2$: :C, 54.90; H, 6.10; N, 10.16; Cl, 17.21. Found: C, 55.08; H, 6.08; N, 10.14; Cl, 17.11.

IR (CHCl$_3$): 3600, 3320, 1712, 1680, 1545, 1489, 1470

NMR (CDCl$_3$) δ (200 MHz): 1.682 (dd, $J_1 = 12$ Hz, $J_2 = 2$ Hz, 2H); 1.772 (quint, J = 7 Hz, 2H); 2.042 (quint, J = 8 Hz, 2H); 2.062 (s, 1H); 2.191 (td, $J_1 = 13$ Hz, $J_2 = 4$ Hz, 2H); 2.409 (t, J = 11 Hz, 2H); 2.497 (t, J = 7 Hz, 2H); 2.628 (t, J = 8 Hz, 2H); 2.837 (dd, $J_1 = 11$ Hz, $J_2 = 2$ Hz, 2H); 3.394 (q, J = 6 Hz, 2H); 3.854 (t, J = 7 Hz, 2H); 7.393,7.401,7.716 (sx3,3H)

(2) A solution of 2.77 g of the compound (III-1) and 1.60 g of p-toluenesulfonic acid in 300 ml of toluene is refluxed for 48 hours to separate water as azeotropic mixture of toluene. After removal of the solvent, the residue is dissolved in ethyl acetate and washed with aq.NaOH and water. The solution is dried over $Na_2SO_4$ and concentrated under reduced pressure. The oily residue is subjected to column chromatography with silica gel, eluting with ethyl acetate-methylene chloride/methanol (20/1 v/v) to prepare 2.26 g (Yield: 89.3%) of the objective compound (I a-1) as an oil. The maleate is recrystallized from i-PrOH to prepare 2.50 g colorless needles. mp. 135.5°-136.5° C.

Anal Calcd. (%) for $C_{19}H_{23}N_3O_2Cl_2 \cdot C_4H_4O_4$: C, 53.84; H, 5.32; N, 8.18; Cl, 13.93. Found: C, 53.91; H, 5.31; N, 8.20; Cl, 13.84.

IR (Nujol) cm$^{-1}$: 3310, 1713. 1680, 1625, 1580, 1550 (sh), 1518, 1485, 1455

NMR (CDCl$_3$) δ (200 MHz): 1.829 (quint, J = 7 Hz, 2H); 2.039 (quint, J = 8 Hz, 2H); 2.50~2.55 (m, 4H); 2.612 (t, J = 8 Hz, 2H); 2.714 (t, J = 6 Hz, 2H); 3.171 (q, J = 3.3 Hz, 2H); 3.398 (q, J = 7 Hz, 2H); 3.874 (t, J = 7 Hz, 2H); 6.100 (quint, J = 2 Hz, 1H); 7.224 (dd, $J_1 = 8$ Hz, $J_2 = 2$ Hz, 1H); 7.397 (d, J = 8 Hz, 1H); 7.463 (d, J = 2 Hz, 2H); 8.513 (brs, 1H)

EXAMPLE 2-16

The reaction is performed in the same manner as Example 1 to prepare the compound (I a). The reaction conditions are shown in table 1 and 2, and physical constants of the compound (III) are shown in table 3 and those of the compound (I a) are shown in table 4.

TABLE 1

(Step 1)

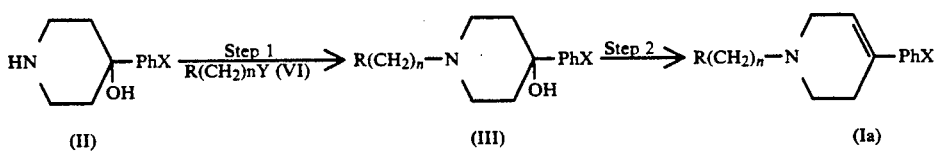

| Ex. No. | (II) X= | R(CH$_2$)nY(VI) | DMF (ml) | K$_2$CO$_3$ (g) | NaI (g) | reaction condition (1) | eluent condition | g (%) compd. No. |
|---|---|---|---|---|---|---|---|---|
| 2 | CF$_3$ (p) 2.50 g (II-2) | NCONH(CH$_2$)$_3$Cl 2.09 g | 25 | 2.28 | 2.29 | 105-110 7 hr. | CH$_2$Cl$_2$/MeOH = 10/1 | 3.89 (92.2) (III-2) |

TABLE 1-continued (Step 1)

$$\text{HN}\underset{\text{OH}}{\bigcirc}\text{PhX} \xrightarrow[R(CH_2)nY\ (VI)]{Step\ 1} R(CH_2)_n-N\underset{\text{OH}}{\bigcirc}\text{PhX} \xrightarrow{Step\ 2} R(CH_2)_n-N=\bigcirc=\text{PhX}$$

(II)　　　　　　　　　　　(III)　　　　　　　　　(Ia)

| Ex. No. | (II) X= | R(CH₂)nY(VI) | DMF (ml) | K₂CO₃ (g) | NaI (g) | reaction condition (1) | eluent condition | g (%) compd. No. |
|---|---|---|---|---|---|---|---|---|
| 3 | n-Pr (p) 2.25 g (II-3) | ⌐NCONH(CH₂)₃Cl ‖ O  2.10 g | 20 | 2.85 | 2.31 | 105 5 hr. | CH₂Cl₂/MeOH = 10/1 | 2.98 (74.6) (III-3) |
| 4 | Et (p) 3.00 g (II-4) | ⌐NCONH(CH₂)₃Cl ‖ O  2.99 g | 30 | 4.04 | 3.28 | 105 7 hr. | CH₂Cl₂/MeOH = 10/1 | 4.10 (75.2) (III-4) |
| 5 | Ph (p) 4.76 g (II-5) | ⌐NCONH(CH₂)₃Cl ‖ O  3.85 g | 57 | 5.19 | 4.22 | 105 24 hr. | CH₂Cl₂/MeOH = 20/1-10/1 | 7.31 (92.3) (III-5) |
| 6 | t-Bu (p) 6.0 g (II-6) | ⌐NCONH(CH₂)₃Cl ‖ O  5.26 g | 60 | 7.11 | 5.78 | 105 10 hr. | CH₂Cl₂/MeOH = 10/1 | 8.36 (81.0) (III-6) |
| 7 | n-Pr (p) 1.95 g (II-3) | ⌐NCO(CH₂)₃Cl ‖ O  2.02 g | 30 | 2.46 | 2.0 | 105° C. 9 hr. | CH₂Cl₂/MeOH = 20/1-10/1 | 2.0 (65.0) (III-7) |
| 8 | t-Bu (p) 1.98 g (II-6) | ⌐NCO(CH₂)₃Cl ‖ O  0.298 g | 20 | 1.35 | 1.10 | 100° C. 2.6 hr. | CH₂Cl₂/MeOH = 19/1-9/1 | 0.853 (46.9) (III-8) |
| 9 | CF₃ (p) 2.33 g (II-2) | ⌐NCO(CH₂)₃Cl ‖ O  2.02 g | 30 | 2.62 | 2.14 | 100-105° C. 8.5 hr. | CH₂Cl₂/MeOH = 20/1-10/1 | 2.46 (65.0) (III-9) |
| 10 | Ph 930 mg (II-5) | ⌐NCONH(CH₂)₃Cl  0.70 g | 11 | 1.015 | 0.825 | 105° C. 5 hr. | CH₂Cl₂/MeOH/ NH₄OH = 128/16/1-32/6/1 | 0.616 (41.0) (III-10) |

TABLE 1-continued (Step 1)

$$\text{HN}\underset{\text{OH}}{\bigcirc}\text{PhX} \xrightarrow[R(CH_2)_nY (VI)]{\text{Step 1}} R(CH_2)_n-N\underset{\text{OH}}{\bigcirc}\text{PhX} \xrightarrow{\text{Step 2}} R(CH_2)_n-N\bigcirc=\text{PhX}$$

(II)                (III)                (Ia)

| Ex. No. | (II) X= | R(CH$_2$)nY(VI) | DMF (ml) | K$_2$CO$_3$ (g) | NaI (g) | reaction condition (1) | eluent condition | g (%) compd. No. |
|---|---|---|---|---|---|---|---|---|
| 11 | t-Bu (p) 844 mg (II-6) | ⌐NCONH(CH$_2$)$_3$Cl⌐ 0.70 g | 11 | 1.00 | 0.813 | 100° C. 5.5 hr. | CH$_2$Cl$_2$/MeOH/ NH$_4$OH = 128/16/1–64/8/1 | 0.830 (57.3) (III-11) |
| 12 | CF$_3$ (m) 2.5 g (II-7) | ⌐NCONH(CH$_2$)$_3$Cl ‖O⌐ 2.05 g | 25 | 2.76 | 2.25 | 100–105° C. 5.5 hr. | CH$_2$Cl$_2$/MeOH = 10/1 | 3.8 (90.2) (III-12) |
| 13 | CF$_3$ (p) 527 mg (II-2) | ⌐NCONH(CH$_2$)$_5$Cl ‖O⌐ 0.50 g | 7 | 0.59 | — | 105° C. 7 hr. | CH$_2$Cl$_2$/MeOH = 20/1–10/1 | 0.82 (86.0) (III-13) |
| 14 | t-Bu (p) 2.03 g (II-6) | ⌐NCONH(CH$_2$)$_3$Cl ‖O⌐ 1.90 g | 20 | 2.40 | 1.95 | 105° C. 7.5 hr. | CH$_2$Cl$_2$/MeOH = 20/1–7/1 | 2.99 (82.8) (III-14) |
| 15 | Me (p) 1.07 g (II-8) | ⌐NCO(CH$_2$)$_3$Cl ‖O⌐ 1.103 g | 26 | 1.61 | 1.31 | 95° C. 7 hr. | CH$_2$Cl$_2$/MeOH = 19/1–9/1 | 0.477 (24.8) (III-15) |
| 16 | t-Bu (p) 980 mg (II-6) | Ph—N⌐ ⌐N(CH$_2$)$_3$Cl 1.0 g | 20 | 1.16 | 0.94 | 105° C. 6.5 hr. | CH$_2$Cl$_2$/MeOH = 10/1–5/1 | 1.69 (92.6) (III-16) |

TABLE 2 (Step 2)

| starting material | acid | solvent (ml) | reflux time | eluting condition (2) | product (g) |
|---|---|---|---|---|---|
| (III-2) 4.24 g | TsOH.H$_2$O (3.90 g) | toluene(280) dichloro- | 48 hr. | ethyl acetate- CH$_2$Cl$_2$/MeOH = 20/1 | Ia-2 2.26 g |
| (III-3) 2.52 g | CF$_3$COOH (25 ml) | — | 10 hr. | toluene/ ethyl acetate = 1/1 CH$_2$Cl$_2$/MeOH = 20/1 | Ia-3 2.22 g |
| (III-4) 4.10 g | CF$_3$COOH (35 ml) | — | 10 hr. | ethyl acetate- CH$_3$Cl$_3$/MeOH = 30/1–10/1 | Ia-4 3.41 g |
| (III-5) 2.73 g | CF$_3$COOH (30 ml) | — | 9 hr. | CH$_3$Cl$_3$/MeOH = 30/1–20/1 | Ia-5 2.40 g |
| (III-6) 2.08 g | CF$_3$COOH (25 ml) | — | 4 hr. | ethyl acetate- CH$_2$Cl$_2$/MeOH = 30/1–20/1 | Ia-6 1.90 g (95.6) |
| (III-7) 2.67 g | CF$_3$COOH (30 ml) | — | 7.5 hr. | toluene/ethyl- ethyl acetate = 1/1- ethyacetate | Ia-7 0.24 g (59.8) |
| (III-8) 0.822 g | CF$_3$COOH (2 ml) | — | 1.8 hr. | toluene/acetone = 2/1 CH$_2$Cl$_2$/MeOH = 9/1 | Ia-8 0.697 g |

TABLE 2 (Step 2)-continued

| starting material | acid | solvent (ml) | reflux time | eluenting condition (2) | product (g) |
|---|---|---|---|---|---|
| | | | | | (88.8) |
| (III-9) 2.27 g | CF$_3$COOH (25 ml) | — | 24.5 hr. | toluene/ ethyl acetate = 1/1 CH$_3$Cl$_2$/MeOH = 20/1-10/1 | Ia-9 1.13 g (52.1) |
| (III-10) 0.766 g | CF$_3$COOH (10 ml) | — | 1 hr. | CH$_2$Cl$_2$/MeOH = 9/1 | Ia-10* 0.572 g (60.5) |
| (III-11) 0.914 g | CF$_3$COOH (10 ml) | — | 1 hr. | CH$_2$Cl$_2$/MeOH = 9/1 | Ia-11* 0.854 g (75.4) |
| (III-12) 3.42 g | CF$_3$COOH (35 ml) | — | 23 hr. | toluene/ ethyl acetate = 1/1 CH$_2$Cl$_2$/MeOH = 20/1 | Ia-12 3.15 g (96.0) |
| (III-13) 3.45 g | CF$_3$COOH (45 ml) | — | 72 hr. | toluene/ ethyl acetate = 1/1 CH$_2$Cl$_2$/MeOH = 20/1 | Ia-13 2.96 g (89.4) |
| (III-14) 2.82 g | CF$_3$COOH (35 ml) | — | 5 hr. | CH$_2$Cl$_2$/MeOH = 20/1 | Ia-14 2.62 g (97.0) |
| (III-15) 0.544 g | CF$_3$COOH (1 ml) | — — | 3 hr. (room temperature) | toluene/acetone = 2/1 | Ia-15 0.313 g (59.6) |
| (III-16) 1.50 g | CF$_3$COOH (20 ml) | — — | 4 hr. | toluene/ ethyl acetate = 1/1 CH$_2$Cl$_2$/MeOH = 20/1-10/1 | Ia-16 1.40 g (97.4) |

*maleate

TABLE 3

| Compd. No. | mp. (°C.) (solvent) | Anal. Calcd. (%) Found (%) | IR (cm⁻¹) | NMR (δ) |
|---|---|---|---|---|
| III-2 | 151.5~152.5 (CH₂Cl₂—Et₂O) (CH₂Cl₂—Et₂O) | $C_{29}H_{26}N_3O_3F_3$: C,57.92 (58.10) H, 6.26 (6.34) N,10.15 (10.16) F,1357 (13.79) | (CHCl₃) 3600, 3310, 1713 1680, 1605, 1510 1489 | (CDCl₃) 1.712(d-d,$J_1$=12Hz, $J_2$=2Hz, 2H); 1.776(quint J=7Hz, 2H); 2.026 quint, J=7Hz, 2H); 2.046(s, 1H); 2.210(t-d, $J_1$=13Hz, $J_2$=4Hz, 2H); 2.432(t-d, $J_1$=11Hz, $J_2$=2Hz, 2H); 2.490(t, J=7Hz, 2 H); 2.601 (t, J=8Hz, 2H); 2.838(d-d, $J_1$=11Hz, $J_2$=2Hz, 2H); 7.595(d, J=8Hz, 2H); 7.679(d, J=8Hz, 2H); 8.619(brs. 1H) |
| III-3 | 96.0~97.0 (ethyl-acetate-Et₂O) | $C_{22}H_{33}N_3O$: C, 67.84 (68.18) H, 8.41 (8.58) N, 10.74 (10.84 | (CHCl₃) 3600, 3320, 1713 1680, 1602, 1547 1490, 1460 | (CDCl₃) 1.634(sextet, J=7Hz, 2H); 1.70~1.85(m, 4H); 2.018(quint, J=8Hz, 2H); 2.185(t-d), $J_1$=13Hz, $J_2$=4Hz, 2H); 2.38~2.64(m, 8H); 2.819(d-d, $J_1$= (d, J=8Hz, 2H); 7.343 (d, j=8Hz, 2H); 8.551(brs. 1H) |
| III-4 | 84.0~85.5 |  | (CHCl₃) 3600, 3320, 1713 1680, 1545 | (CDCl₃) 1.235(t, J=8Hz, 3H); 1.72~1.83(m, 4H); 2.022(quint, J=7Hz, 2H); 2.191(t-d), $J_1$13Hz, $J_2$=4Hz, 2H); 2.4~2.7(m, 8H); 3.848(t, J=7Hz, 2H); 7.1 12Hz, $J_2$=1Hz, 2H); 3.375(q, J=6Hz, 2H); 3.848(t, J=7Hz, 2H); 7.1 86(d, J=8Hz, 2H); 7.442(d, J=8Hz, 2H); 8.555(brs. 1H) |
| III-5 | 155.5~156.5 (CH₂Cl₂—Et₂O) | $C_{26}H_{31}N_3O_3$.1/2H₂O C, 70.50 (70.63) H, 7.46(7.82 N, 965 (9.88) | (CHCl₃) 3600, 3320, 1713 1682, 1545 | (CDCl₃) 1.84~1.73(m, 4H); 2.014(quint, $J_1$=8Hz, 2H); 2.247(t-d, $J_1$=14Hz, $J_2$=4Hz, 2H); 2.458(t-d, $J_1$=14Hz, $J_2$1H, 2H); 2.507(t, J=7Hz, 2H); 2.595(t, J=8Hz, 2H); 2.853(t, J=11Hz, 2H); 3.386(q, J=6Hz, 2H); 3.846(t,J=7Hz, 2H); 7.25~7.65 (m, 9H); 8.577(brs. 1H) |
| III-6 | 149.5~150.5 (CH₂Cl₂—Et₂O) | $C_{23}H_{36}N_3O_3$ C, 68.48 (68.80) H, 8.69 (8.79) N, 10.39(10.46) | (CHCl₃) 3600, 3320, 1713 1680, 1543 | (CDCl₃) 1.303(s, 9H); 1.521(s, 1H); 1.738(d-d, $J_1$=11Hz, $J_2$=3Hz, 2H); 1.793(quint, J=8Hz, 2H); 2.022(quint, J=7Hz, 2H); 2.195(t-d, $J_1$=13Hz, $J_2$=4Hz, 2H); 2.39~2.53(m, 4H); 2.593(t, J=8Hz, 2H); 2.823 (d, J=11Hz, 2H); 3.375(q, J=7Hz, 2H); 3.851(t, J=7Hz, 2H); 7.38, 7.43(ABq, J=9Hz, 4H); 8.543(brs, 1H) |
| III-7 | 161.0~162.5 (CH₂Cl₂-(ethyl-acetate) | $C_{22}H_{33}N_3O_3Cl$.1/2H₂O C, 63.46 (63.68) H, 8.02 (8.18) N, 6.83(6.75)t F, 7.98 (8.54) | (Nujol) 3310, 2640, 2560 1730, 1680 | (CDCl₃) 0.939(t, J=7Hz, 3H); 1.630(sextet, J=7Hz, 2H); 1.791(d, J=12Hz, 2H); 1.87-2.10(m, 4H); 2.246(t-d, $J_1$=12Hz, $J_2$=3Hz, 2H); 2.50-2.68(m, 8H); 2.920(d, J=12Hz, 2H); 2.957(t, J=7Hz, 2H); 3.804 (t, J=7Hz, 2H); 7.156, 7.406(ABq, J=8Hz, 4H) |
| III-8 | 207.0~210.0 (CH₂Cl₂—Et₂O-n-hexane) | $C_{23}H_{34}N_2O_3$: C, 63.73 (71.47) H, 8.09 (8.87) N, 7.31 (7.25) | (CHCl₃) 3663, 3598, 3345 2630, 2460, 2410 1740, 1692, 1611 1509, 1471, 1460 | (CDCl₃) 1.299(s, 9H); 1.960(d, J=14Hz, 2H); 1.95~2.13(m, 4H); 2.17~2.35 (m, 2H); 2.606(t, J=8.hz, 2H); 2.694(t-d, $J_1$=14Hz, $J_2$2Hz, 2H); 2.95~3.10(m, 4H); 3.25~3.45(m, 4H); 3.800(t, J=7Hz, 2H); 7.368. 7.441(ABq, J=8Hz, 4H) |
| III-9 | 147.0~148.0 (CH₂Cl₂—Et₂O) | $C_{29}H_{23}N_3O_3F_3$.1/5H₂O C, 59.79 (59.75) H, 6.27 (6.97) N, 6.79 (6.37) F, 14.26 (14.18) | (CHCl₃) 3600, 3320, 1738, 1693 1620 | (CDCl₃) 1.715(d-d, $J_1$=14Hz, $J_2$=2Hz, 2H); 1.878(s, 1H); 1.898(quint, J=8 Hz, 2H); 2.021(quint, $J_1$=8Hz, 2H); 2.152(t-d, $J_1$=14Hz, $J_2$=4Hz, 2H); 2.451(t-d, $J_1$=15Hz, $J_2$=2Hz, 2H); 2.482(t, J=8Hz); 2.584 (t, J=8Hz, 2H); 2.862 (d, J=15Hz, 2H); 2.936(t, J=7Hz, 2H); 3.794 (t, J=8Hz, 2H) 7.579, 7.627 (ABz, J=8Hz, 4H) |
| III-10 | 225.0~228.0 (CH₂Cl₂—MeOH—Et₂O) | $C_{23}H_{33}N_3O_2$.1/10H₂O C, 73.25 (73.35) H, 8.26 (8.18) N, 1021 (10.27) | (Nujol) 3300, 3055, 3030 1606, 1528, 1487 1471, 1456, 1448 | (CDCl₃) 1.775(quint, J=7Hz, 2H); 1.845(d, $J_1$=14Hz, 2H); 2.89-1.96(m, 4H); 2.171 (t-d, $J_1$=13Hz, $J_2$=4Hz, 2H); 2.52-2.63(m, 4H); 2.900(d, J=12Hz, 2H); 3.25-3.38(m, 4H); 7.30-7.70(m, 9H) |
| III-11 | 138.5~140.5 (CH₂Cl₂—Et₂O) | $C_{23}H_{37}N_3O_2$.2/5H₂O C, 70.07 (69.98) H, 9.54 (9.65) N, 10.66 (10.64) | (Nujol) 3350, 3150, 1631 1542, 1509, 1485 1460, 1441, 1388 | (CDCl₃) 1.322(s, 9H); 1.76-1.94(m, 8H); 2.262(t-d, $J_1$=14Hz, $J_2$=4Hz, 2H); 2.50-2.65(m, 4H); 2.951(d, J=11Hz, 2H); 3.30-3.39(m, 4H); 5.738(brs, 1H); 7.378, 7.418(ABz. J=8Hz, 4H) |
| III-12 | 113.5~114.5 | $C_{20}H_{26}N_3O_3F_3$: | (CHCl₃) | (CDCl₃) |

TABLE 3-continued

| Compd. No. | mp. (°C.) (solvent) | Anal. Calcd. (%) Found (%) | IR (cm$^{-1}$) | NMR (δ) |
|---|---|---|---|---|
| | (CH$_2$Cl$_2$—Et$_2$O) | C, 57.90 (58.10) H, 6.26 (6.34) N, 10.14 (10.16) F, 13.49 (13.79) | 3600, 3320, 1713 1680, 1545, 1490 1385, 1332 | 1.715 (d-d, J$_1$=12Hz, J$_2$=2Hz, 2H); 2.780(quint J=7Hz, 2H); 2.000 (s, 1H); 2.027(quint, J=7Hz, 2H); 2.253(t-d, J$_2$=13Hz, J$_2$=4Hz, 2H); 2.442(d, J=12Hz, 2H); 2.504(t, J=7Hz, 2H); 2.606(t, J=8Hz, 2 H);2.854(d-d, J$_1$=11Hz, J$_2$=3Hz, 2H); 3.394(quint, J=7Hz, 2H); 3.850(t, J=7Hz, 2H); 7.474(d, J=7Hz, 1H); 7.492(t, J=7Hz, 1H); 7.746(d, J=7Hz, 1H); 7.871(s, 1H); 8.678(brs, 1H) (CDCl$_3$) |
| III-13 | oil | — | — | 1.30–1.44(m, 2H); 1.584(quint×2, J=7Hz, 4H); 1.747(d, J=12Hz, 2 H); 2.022(quint, J=7Hz, 2H); 2.216(t-d, J$_1$=13Hz, J$_2$=4Hz, 2H); 2.41–2.49(m, 4H); 2.600(t, J=8Hz, 2H); 2.773(d, J=11Hz, 2H); 3.292 (q, J=7Hz, 2H); 3.837(t, J=7Hz, 2H); 7.598, 7.662(ABz, J=9 Hz, 4H); 8.428(brs, 1H) (CDCl$_3$) |
| III-14 | 153.0–154.0 (CH$_2$Cl$_2$—Et$_2$O) | C$_{24}$H$_{37}$N$_3$O$_3$: C, 69.29 (69.36) H, 8.93 (8.97) N, 10.14 (10.11) | (CHCl$_3$) 3600, 3280, 1702 (sh), 1697, 1645 1530, 1480, 1460 1400 | 1.319(s, 9H); 1.623(s, 1H); 1.71–1.86(m, 8H); 2.190(t-d, J$_1$=13 Hz, J$_2$=4Hz, 2H); 2.39–2.58(m, 6H); 2.824(d, J=11Hz, 2H); 3.375 (q, J=7Hz, 2H); 3.75–3.82(m, 2H); 7.463, 7.372(ABz, J=9Hz, 4H); 9.479(brs, 1H) (CDCl$_3$) |
| III-15 | ~180 (CH$_2$Cl$_2$—Et$_2$O) | — | — | 1.782(d-d, J$_1$=14Hz, J$_2$=2Hz, 2H); 1.90–2.12(m, 6H); 2.275(t-d, J$_1$=14Hz, J$_2$=2Hz, 2H); 2.330(s, 3H); 2.600(t, J=8Hz, 4H); 2.965 (t, J=7Hz, 4H); 3.810(t, J=7Hz, 2H); 7.163, 7.394(ABz, J=8Hz, 4H) (CDCl$_3$) |
| III-16 | 129.0–130.5 (CH$_2$Cl$_2$—Et$_2$O) | C$_{28}$H$_{41}$N$_3$O.1/3H$_2$O C, 76.08 (76.15) H, 9.41 (9.51) N, 9.63 (9.51) | (CHCl$_3$) 3600, 1602, 1580 1505(sh), 1495 1470, 1460(sh), 1455, 1400, 1380 | 1.661(s, 1H); 1.77–1.94(m, 4H); 2.285(t-d, J$_1$=13Hz, J$_2$=2Hz, 2H); 2.460(t, J=7Hz, 2H); 2.53–1.65(m, 6H); 3.18–3.24(m, 2H); 680–7.48(m, 9H); |

TABLE 4

| Compd. No. | mp. (°C.) (solvent) | Anal Calcd. (%) Found (%) | IR (cm$^{-1}$) | NMR (δ) |
|---|---|---|---|---|
| Ia-2 | 187.0–188.5 (oxalate) (i-PrOH) | $C_{20}H_{24}N_3O_2F_3 \cdot C_2H_2O_4$ C, 54.45 (54.43) H, 5.38 (5.40) N, 8.76 (8.66) F, 12.26 (11.74) | (CHCl$_3$) 3290, 2600 (br), 1710, 1685, 1615 1550, 1460 | (CDCl$_3$-CD$_3$OD=1/5) 2.00~2.20(m, 4H); 2.620(t, J=8Hz, 2H); 2.98~2.87(brs, 2H); 3.29 2(t, J=8Hz, 2H); 3.451(t, J=7Hz, 2H); 3.556(t, J=6Hz, 2H); 3.81 9(t, J=7Hz, 2H); 3.977(d, J=3Hz, 2H); 6.239(t, J=3Hz, 1H); 7.64 6(s, 4H) |
| Ia-3 | 162.0–162.5 (maleate) (i-PrOH) | $C_{26}H_{35}N_3O_6$: C, 64.23 (64.31) H, 7.23 (7.27) N, 8.54 (8.65) | (Nujol) 3330, 1705 (s), 1695, 1620, 1575 1528 | (CDCl$_3$) 0.935(t, J=7Hz, 3H); 1.629(sextet, J=7Hz, 2H); 1.828(quint, J= 7Hz, 2H); 2.015 (quint, J=7Hz, 2H); 2.49~2.64(m, 8H); 2.706 (t, J=6Hz, 2H); 3.158(q, J=3Hz, 2H); 3.387(q, J=7Hz, 2H); 3.858(t, J=7Hz, 2H); 6.032(quint, J=2Hz, 1H); 7.117(d, J=8Hz, 2H); 7.302 (d, J332.8Hz, 2H); 8.486(brs, 1H) |
| Ia-4 | 86.0–87.0 (ether) | $C_{27}H_{29}N_3O_2$ C, 70.97 (70.95) H, 8.11 (8.22) N, 11.97 (11.82) | (CDCl$_3$) 3220, 1713, 1682 1545, 1488, 1460 | (CDCl$_3$) 1.227(t, J=7Hz, 3H); 1.824(quint, J=7Hz, 2H); 2.015(quint, J=7 Hz, 2H); 2.527(t, J=8Hz, 2H); 2.561(brs, 2H); 2.591(t, J=8Hz, 2H); 2.629(q, J=8Hz, 2H); 3.150(q, J=3Hz, 2H); 3.386(q, J=7Hz, 2H); 3.856(t, J=7Hz, 2H); 6.017(quint, J=2Hz, 1H); 7.141(d, J= 8Hz, 2H); 7.310(d, J=8Hz, 2H); 8.490(brs. 1H) |
| Ia-5 | 144.0–146.0 (decom. point) (ethyl acetate) | $C_{25}H_{29}N_3O_2$ C, 74.32 (74.41) H, 7.21 (7.24) N, 10.49 (10.41) | (CHCl$_3$) 3320, 1702, 1680 1600, 1545, 1485 | (CDCl$_3$) 1.840(quint, J=7Hz, 2H); 2.019(quint, J=8Hz, 2H); 2.555(t, J=8 Hz, 2H); 2.584(br, 2H); 2.596(t, J=8Hz, 2H); 2.733(t, J=6Hz, 2H); 3.190(q, J=3Hz, 2H); 3.398(q, J=7Hz, 2H); 3.863(t, J=7Hz, 2H); 6.128(quint, J=3Hz, 1H); 7.26~7.63(m, 9H); 8.504(brs, 1H) |
| Ia-6 | 173.0–174.0 (decom.) (maleate) (i-PrOH—MeOH) | $C_{23}H_{33}N_3O_2 \cdot C_4H_4O_4$ C, 64.68 (64.91) H, 7.48 (7.46) N, 8.38 (8.41) | (Nujol) 3320, 1712, 1690 1620, 1580, 1543 | (CDCl$_3$)(free) 1.314(s, 9H); 1.837(quint, J=7Hz, 2H); 2.022(quint, J=7Hz, 2H); 2.5~2.6(m, 6H); 2.717(t, J=6Hz, 2H); 3.169(q, J=3Hz, 2H); 3.387 (q, J=6Hz, 2H); 6.023(q, J=2Hz, 1H); 7.332(s, 4H); 8.496(brs. 1H) |
| Ia-7 | 190.0–191.0 (oxalate) (MeOH) | $C_{20}H_{24}N_3O_2F_3 \cdot C_2H_2O_4$ C, 64.39 (64.85) H, 7.27 (7.26) N, 6.12 (6.30) | (Nujol) 2500, 1732, 1725 (sh), 1685, 1610 (br) | (CDCl$_3$) 0.935(t, J=7Hz, 3H); 1.629(sextet, J=8Hz, 2H); 1.978(sextet, J= 7Hz, 2H); 1.989(sextet, J=7Hz, 2H); 2.52–2.60(m, 8H); 2.745(t, J=6Hz, 2H); 2.973(t, J=7Hz, 2H); 3.195(q, J=3Hz, 2H); 3.795(t, J=7Hz, 2H); 6.022(quint, J=2Hz, 1H); 7.120, 7.299(ABz, J=8Hz, 4H) |
| Ia-8 | 96.0–97.0 (Et$_2$O— n-hexane) | $C_{23}H_{32}N_2O_2$: C, 76.23 (74.96) H, 8.73 (8.75) N, 7.65 (7.60) | (CHCl$_3$) 1737, 1692, 1508 1482, 1459, 1427 1364 | (CDCl$_3$) 1.317(s, 9H); 1.962(sextet, J=6Hz, 2H); 1.996(sextet, J=6Hz, 2H); 2.570(q, J=8Hz, 6H); 2.721(t, J=5Hz, 2H); 2.972(t, J=7Hz, 2H); 3.174(q, J=3Hz, 2H); 3.801(t, J=7Hz, 2H); 6.031(quint, J=2 Hz, 1H); 7.331(s, 4H) |
| Ia-9 | 149.5–150.5 (CH$_2$Cl$_2$— Et$_2$O) | $C_{20}H_{23}N_2O_2F_3$ C, 63.17 (63.15) H, 6.09 (6.09) N, 7.38 (7.36) F, 1506 (14.98) | (CHCl$_3$) 1738, 1692, 1615 1477, 1365, 1325 | (CDCl$_3$) 1.964(sextet, J=7Hz, 2H); 2.001(sextet, J=7Hz, 2H); 2.538(q, J= 8Hz, 6H); 2.745(t, J=6Hz, 2H); 2.980(t, J=7Hz, 2H); 3.207(q, J= 3Hz, 2H); 3.803(t, J=7Hz, 2H); 6.160(quint, J=3Hz, 1H); 7.472, 7.565(ABq, J=8Hz, 4H) |
| Ia-10 | 164.0–166.0 (maleate) (MeOH—Et$_2$O) | $C_{25}H_{31}N_3O \cdot C_4H_4O_4$ C, 68.89 (68.89) H, 6.97 (6.98) N, 8.30 (8.31) | (Nujol) 3403, 3037, 2330 1700, 1640, 1578 1537, 1498, 1457 | (CD$_3$OD) 1.88–2.06(m, 4H); 2.951(brs, 2H); 3.29–3.40(m, 6H); 3.557(brs, 2H); 3.959(brs, 2H); 6.220(s, 1H); 6.248(s, 2H); 7.30–7.70(m, 9H) |
| Ia-11 | 138.0–140.0 (maleate) (MeOH—Et$_2$O) | $C_{23}H_{35}N_3O \cdot C_4H_4O_4 \cdot$ 1/5H$_2$O C, 66.16 (66.29) H, 8.21 (8.12) N, 8.82 (8.59) | (Nujol) 3522, 3362, 2718 2350, 1701, 1630 1579, 1524, 1498 | (CD$_3$OD) 1.316(s, 9H); 1.87–2.08(m, 6H); 2.896(brs, 2H); 3.22–3.36(m, 8H); 3.526(brs, 2H); 3.918(brs, 2H); 6.117(quint, J=3Hz, 1H); 6.245(s, 2H); 7.414(s, 4H) |

TABLE 4-continued

| Compd. No. | mp. (°C.) (solvent) | Anal Calcd. (%) Found (%) | IR (cm⁻¹) | NMR (δ) |
|---|---|---|---|---|
| Ia-12 | 128.0-129.0 (maleate) (i-PrOH—MeOH) | C₂₀H₂₄N₃O₂F₃·C₄H₄O₄<br>C, 56.35 (56.36)<br>H, 5.55 (5.52)<br>N, 8.21 (8.22)<br>F, 11.08 (11.14) | (Nujol)<br>3300, 2300 (br),<br>1710, 1638, 1625<br>1570, 1530, 1500<br>1460, 1445 | (CDCl₃)<br>1.831(quint, J=7Hz, 2H); 2.027(quint, J=8Hz, 2H); 2.51-2.65(m, 6H); 2.729(t, J=6Hz, 2H); 3.186(q, J=3Hz, 2H); 3.397(q, J=7Hz, 2H); 3.865(t, J=7Hz, 2H); 6.145(quint, J=2Hz, 1H); 7.41-7.63(m, 4H); .517 (brs. 1H) |
| Ia-13 | 128.0-129.5 (oxalate) MeOH—i-PrOH) | C₂₂H₂₈N₃O₂F₃·C₂H₂O₄·1/2PrOH<br>C, 56.18 (56.35)<br>H, 6.23 (6.39)<br>N, 7.70 (7.73) | (Nujol)<br>3510, 3310, 1708<br>1690, 1680, 1615<br>1537, 1480, 1460 | (CDCl₃)<br>1.35-1.47(m, 2H); 1.613(quint×2, J=7Hz, 4H); 2.025(quint, J=8 Hz, 2H); 2.44-2.65(m, 6H); 2.716(t, J=5Hz, 2H); 3.181(q, J=3Hz, 2H); 3.312(q, J=6Hz, 2H); 3.862(t, J=7Hz, 2H); 6.157(quint, J=2 Hz, 1H); 7.472, 7.563(ABz, J=8Hz, 4H); 8.419(brs. 1H) |
| Ia-14 | 185.0-186.5 (maleate) (MeOH) | C₂₄H₃₅N₃O₂·C₄H₄O₄<br>C, 65.53 (65.48)<br>H, 7.62 (7.65)<br>N, 8.24 (8.18) | (Nujol)<br>3285, 1695, 1648<br>1620, 1580, 1523<br>1477, 1460, 1450<br>1367 | (CDCl₃)<br>1.312(s, 9H); 1.77-1.88(m, 6H); 2.49-2.56(m, 6H); 2.704(t, J=6 Hz, 2H); 3.160(q, J=3Hz, 2H); 3.380(q, J=7Hz, 2H); 3.76-3.82(m, 2H); 6.026(quint, J=2Hz, 1H); 7.328(s, 4H); 9.444(brs, 1H) |
| Ia-15 | 109.5-110.0 Et₂O—n-hexane) | C₂₀H₂₆N₂O₂<br>C, 73.79 (73.59)<br>H, 8.08 (8.03)<br>N, 8.55 (8.58) | (CHCl₃)<br>1738, 1692, 1512<br>1485, 1460, 1430<br>1367 | (CDCl₃)<br>1.939(quint, J=7Hz, 2H); 2.007(quint, J=7Hz, 2H); 2.328(s, 3H); 2.49-2.63(m, 4H); 2.713(t, J=5Hz, 2H); 2.969(t, J=7Hz, 2H); 3.153 (q, J=3Hz, 2H); 3.794(t, J=7Hz, 2H); 6.018(quint, 1=2Hz, 1H); 7.115, 7.280(ABz, J=8Hz, 4H) |
| Ia-16 | 105.0-106.0 (maleate) (i-PrOH—Et₂O) 210.0-212.5 (MeOH) | C₂₈H₃₉N₃O₂·C₄H₄O₄<br>C, 66.49 (66.54)<br>H, 7.26 (7.29)<br>N, 6.59 (6.47) | (Nujol)<br>7710, 1622, 1598<br>1575, 1495(sh),<br>1480, 1462, 1450<br>1385, 1360 | (CDCl₃)<br>1.315(s, 9H); 1.78-1.84(m, 8H); 2.43-2.75(m, 8H); 3.16-3.25(m, 6H); 6.043(quint, J=2Hz, 1H); 6.80-7.34(m, 9H) |

EXAMPLE 17

1-[4-{4-(4-trifluoromethylphenyl)-1,2,5,6-tetrahydropyridin-1-yl}-butylcarbamoyl]-2-oxopyrrolidine (I a-17)

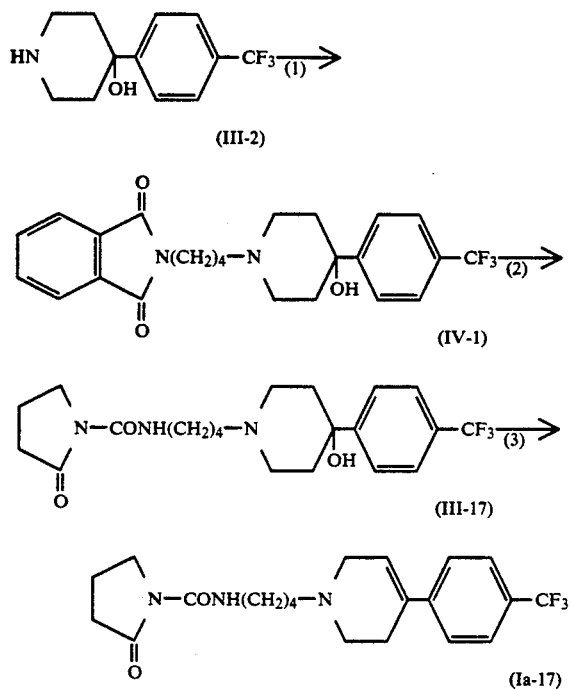

(1) A solution of 2.00 g of 4-hydroxy-4-(4-trifluoromethylphenyl)piperidine (II-2) and 2.42 g of phthalimido butyl bromide in 20 ml of DMF in the presence of 2.26 g of $K_2CO_3$ is stirred at 105° C. for 6 hours. The reaction mixture is poured into ice-water, and the solution is extracted with ethyl acetate. The organic layer is washed with water, dried over $Na_2SO_4$ and concentrated under reduced pressure. The obtained residue is subjected to column chromatography with silia gel eluting with methylene chloride/methanol (20/1 v/v). The purified substance is recrystallized from methylene chloride/ether to prepare 3.0 g of the compound (IV-1). mp. 139.0°-140.5° C.

Anal Calcd. (%) for $C_{24}H_{25}N_2O_3F_3$: C, 64.23; H, 5.73; N, 6.10; F, 12.98. Found: C, 64.57; H, 5.64; N, 6.27; F, 12.77.

IR (CHCl$_3$): 3590, 1772, 1713, 1618, 1470, 1440, 1409(sh), 1389

NMR (CDCl$_3$) (200 MHz) δ: 1.52-1.80 (m, 6H); 1.843 (s, 1H); 2.152 (td, $J_1=13$ Hz, $J_2=4$ Hz, 2H); 2.37-2.50 (m, 4H); 2.838 (dd, $J_1=9$ Hz, $J_2=2$ Hz, 2H); 3.728 (t, $J=7$ Hz, 2H); 7.613, 7.640 (ABq, $J=9$ Hz, 4H) 7.7-7.9 (m, 4H)

(2) A solution of 2.56 g of the compound (IV-1) and 424 mg of hydrazine hydrate in 25 ml of ethanol is refluxed for 3 hours. After the excess agent is distilled off under reduced pressure, the residue is mixed with 1.15 g of 1-phenoxycarbonyl-2-oxopyrrolidine and heated at 105° C. for 1.5 hours. The reaction mixture is subjected to column chromatography with silica gel eluting with methylene chloride/methanol=20/1-10/1 v/v. The obtained material is recrystallized from methylene chloride-ether to prepare 1.76 g (Yield: 73.5%) of the objective compound (III-17) as colorless needles. mp. 150.5°-152.0° C.

Anal Calcd. (%) for $C_{21}H_{28}N_3O_3F_3$: C, 58.78; H, 6.51; N, 9.75; F, 13.56. Found: C, 59.01; H, 6.60; N, 9.83; F, 13.33.

IR (CHCl$_3$): 3590, 3320, 1713, 1680, 1618, 1545, 1489, 1460, 1409, 1385, 1328

NMR (CDCl$_3$): 1.57-1.63 (m, 4H); 1.743 (d, $J=12$ Hz, 2H); 2.019 (quint, $J=7$ Hz, 2H); 2.189 (td, $J_1=13$ Hz, $J_2=4$ Hz, 2H); 2.341 (s, 1H); 2.42-2.55 (m, 4H); 2.595 (t, $J=8$ Hz, 2H); 2.862 (dd, $J_1=10$ Hz, $J_2=2$ Hz, 2H); 3.311 (q, $J=6$ Hz, 2H); 3.822 (t, $J=7$ Hz, 2H); 7.591, 7.653 (ABq, $J=9$ Hz, 4H); 8.438 (brs, 1H)

(3) A solution of 1.40 g of the compound (III-17) in 20 ml of trifluoro acetic acid is refluxed for 72 hours. After removal of the excess reagent, the residue is poured into sodium hydroxide, and the solution is extracted with ethyl acetate. The organic layer is dried over MgSO$_4$ and concentrated under reduced pressure. The oily residue is subjected to column chromatography with silica gel, eluting with methylene chloride/methanol (20/1 v/v) and recrystallized from i-PrOH-ether to prepare 1.31 g (Yield: 97.7%) of the objective compound (I a-17) as needles. mp. 136.0°-136.5° C.

Anal Calcd. (%) for $C_{21}H_{26}N_3O_2F_3$: C, 61.87; H, 6.49; N, 10.26; F, 13.87, Found: C, 61.60; H, 6.40; N, 10.26; F, 13.92.

IR (CHCl$_3$): 3310, 1713, 1680, 1615, 1545, 1487, 1458, 1385, 1327

NMR (CDCl$_3$) (200 MHz) δ: 1.55-1.67 (m, 4H); 2.031 (quint, $J=8$ Hz, 2H); 2.47-2.65 (m, 6H); 2.725 (t, $J=5$ Hz, 2H); 3.190 (q, $J=3$ Hz, 2H); 3.344 (q, $J=6$ Hz, 2H); 3.857 (t, $J=8$ Hz, 2H); 6.156 (quint, $J=2$ Hz, 1H); 7.471, 7.564 (ABq, $J=8$ Hz, 4H); 8.436 (brs, 1H)

EXAMPLE 18

1-[N-propyl-N-[3-{4-(4t-butylphenyl)-1,2,5,6-tetrahydropyridin-1-yl}-propylcarbamoyl]]-2-oxopyrrolidine (I a-18)

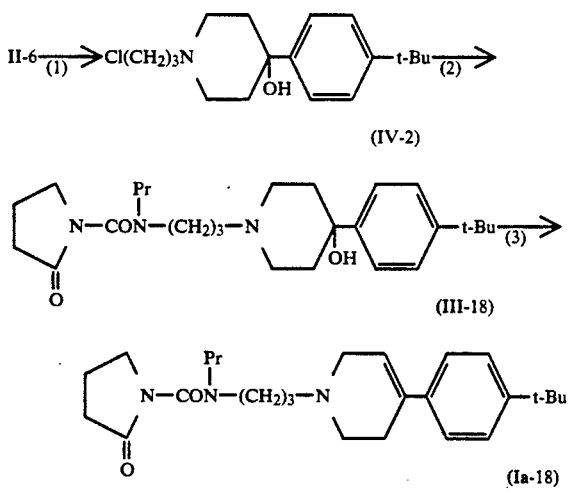

(1) A solution of 2.00 g of the compound (II-6) and 1.42 g of 3-bromo-1-chloropropane in 30 ml of DMF is stirred in the presence of 2.37 g of $K_2CO_3$ at room temperature for 3.5 hours. The reaction mixture is poured into ice-water, and the solution is extracted with ethyl acetate. The organic layer is washed with water, dried and concentrated under reduced pressure to prepare 1.32 g of the compound (IV-2).

(2) A solution of 0.5 g of the compound (IV-2) and 0.44 ml of n-propyl in 1 ml of DMF is heated at 105° C. for 2 hours under stirring. The mixture is concentrated, and the residue is poured into aq.NaOH. The solution is extracted with methylene chloride, the organic layer is dried over MgSO$_4$ under reduced pressure. The oily residue is mixed with 310 mg of 1-phenoxycarbonyl-2-oxopyrrolidine and reacted at 115° C. for 2 hours. The reaction mixture is dissolved into methylene chloride, washed with aq. NaOH and aq.NaCl in order, dried over Na$_2$SO$_4$, and concentrated under reduced pressure. The oily residue is subjected to column chromatography with silica gel, eluting with methylene chloride/methanol (20/1–10/1 v/v) to prepare 500 mg (Yield: 70.0%) of the compound (III-18) as an oil.

IR (CHCl$_3$): 3595, 1720, 1665, 1605, 1517, 1465(sh), 1460, 1425, 1400, 1375

NMR (CDCl$_3$): 0.889 (t, J=7 Hz, 3H); 1.316 (s, 9H); 1.594 (q, J=8 Hz, 2H); 1.74–1.89 (m, 4H); 2.076 (quint, J=7 Hz, 2H); 2.207 (t, J=15 Hz, 2H); 2.435 (t, J=8 Hz, 2H); 2.48–2.60 (m, 4H); 2.80–2.90 (m, 2H); 3.317 (t, J=4 Hz, 2H); 3.421 (t, J=4 Hz, 2H); 3.712 (t, J=7 Hz, 2H); 7.368, 7.436 (ABq, J=8 Hz, 4H)

(3) A solution of 1.40 g of the compound (III-17) in 15 ml of trifluoroacetic acid is refluxed for 2.5 hours. The solution is concentrated, and the residue is poured into aq.NaOH. The solution is extracted with ethyl acetate, and the organic layer is dried over MgSO$_4$ and concentrated under reduced pressure. The oily residue is subjected to column chromatography with silica gel, eluting with toluene/ethyl acetate (1/1 v/v) to prepare 1.07 g (Yield: 80%) of the objective compound (I a-18) as an oil. mp. 158.5°–159.5° C. (dec.)

Anal Calcd. (%) for C$_{26}$H$_{39}$N$_3$O$_2$.1/2 H$_2$O: C, 64.38; H, 8.11; N, 8.05. Found: C, 64.10; H, 8.07; N, 8.01.

IR (Nujol): 3420, 2720, 2590, 2500, 1715, 1692, 1675(sh), 1610(br), 1515, 1460

NMR (CD$_3$OD) (200 MHz)δ: 0.894 (t, J=7 Hz, 3H); 1.312 (s, 9H); 1.618 (q, J=7 Hz, 2H); 2.117 (quint, J=7 Hz, 4H); 2.458 (t, J=8 Hz, 2H); 2.872 (brs, 2H); 3.28–3.37 (m, 4H); 3.49–3.56 (m, 4H); 3.695 (t, J=7 Hz, 2H); 3.932 (brs, 2H); 6.089 (quint, J=2 Hz, 1H); 7.402 (s, 4H)

EXAMPLE 19

1-[3-{4-(4-tert-butylphenyl)-1,2,5,6-tetrahydropyridin-1-yl}propyl]pyrrolidine (I a-19)

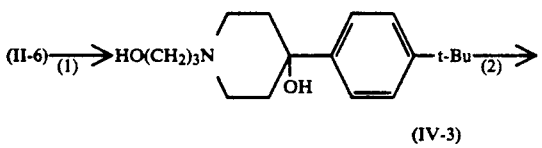

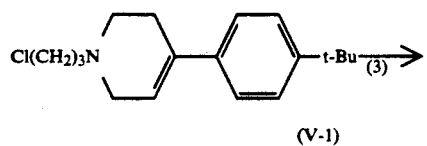

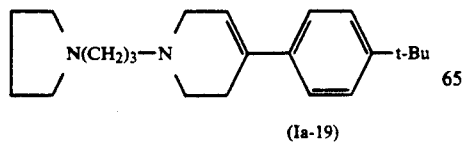

(1) A mixture of 10.061 g of the compound (II-6) and 5.41 ml of 3-chloro-1-propanol is stirred at 140° C. for 6 hours in the presence of 12.03 ml of Et$_3$N. The reaction mixture is recrystallized from methylene chloride-ether-n-hexane to prepare 9.357 g (Yield: 74.0%) of the compound (IV-3). mp. 122.5°–123.5° C.

Anal Calcd. (%) for C$_{18}$H$_{29}$NO$_2$.1/10 H$_2$O : C,73.72; H,9.93; N,4.82. Found: C,73.73; H,10.04; N,4.78.

IR (CHCl$_3$) cm$^{-1}$: 3600, 3225, 1509, 1472, 1437, 1424, 1399, 1372 (sh), 1366

NMR (CDCl$_3$) δ: 1.31 (s, 9H); 1.62–1.85 (m, 4H); 2.119 (td, J$_1$=13 Hz, J$_2$=4 Hz, 2H); 2.507 (td, J$_1$=12 Hz, J$_2$=2 Hz, 2H); 2.707 (t, J=6 Hz, 2H); 2.973 (d, J=11 Hz, 2H); 3.829 (t, J=6 Hz, 2H); 7.367, 7.417 (ABq, J=8 Hz, 4H)

(2) A mixture of 10.568 g of the compound (IV-3) and 26.4 ml of thionyl chloride is stirred at room temperature overnight. Excess reagent is distilled off under reduced pressure, and the residue is poured into aq.Na$_2$CO$_3$. The solution is extracted with methylene chloride, and the organic layer is dried over MgSO$_4$ and concentrated. The residue is subjected to column chromatography with silica gel, eluting with toluene/acetone (8/1–6/1 v/v) and recrystallized from n-hexane to prepare 2.167 g (Yield: 20.5%) of the compound (V-1) as colorless crystals.

Anal Calcd. (%) for C$_{18}$H$_{26}$NCl: : C, 73.86; H, 9.08; N, 4.96; Cl, 12.35. Found: C, 74.07; H, 8.98; N, 4.80; Cl, 12.15.

IR (CHCl$_3$): 1640, 1610, 1510, 1470, 1390, 1380

NMR (CDCl$_3$): 1.315 (s, 9H); 2.041 (quint, J=7 Hz, 2H); 2.50–2.66 (m, 4H); 2.714 (t, J=5 Hz, 2H); 3.169 (q, J=3 Hz, 2H); 3.638 (t, J=7 Hz, 2H); 6.032 (quint, J=3H, 1H); 7.334 (s, 4H)

(3) A mixture of 621 mg of the compound (V−1) and 1.78 ml of pyrrolidine is stirred at room temperature for 72 hours. The excess reagent is distilled off, and the residue is subjeced to column chromatography with silica gel, eluting with methylene chloride/methanol/ammonia (128/16/1 v/v) to prepare 675 mg of the compound (I a-19) as an oil, which is crystallized as maleate and recrystallized from methanol to give 800 mg (yield: 67.3%) of colorless plates. mp. 190.0°–191.0° C. (dec.)

Anal Calcd. (%) for C$_{22}$H$_{34}$N$_2$O$_2$. C$_4$H$_4$O$_4$: C, 64.74; H, 7.58; N, 5.11. Found: C, 64.50; H, 7.58; N, 5.01.

IR (Nujol): 2355, 1711, 1620, 1577, 1543, 1479(sh), 1461, 1378

NMR (CD$_3$OD) δ: 1.314 (s, 9H); 2.122 (quint, J=3 Hz, 2H); 2.20–2.37 (m, 2H); 2.907 (brs, 2H); 3.30–3.43 (m, 6H); 3.567 (t, J=6 Hz, 2H); 3.949 (brs, 2H); 6.129 (brs, 1H); 6.269 (s, 2H); 7.416 (s, 4H)

EXAMPLE 20

1-[3-{4-(4-trifluoromethyl)-1,2,5,6-tetrahydropyridin-1-yl}-propyl]pyrrolidine (I a-20)

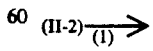

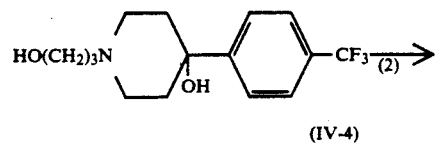

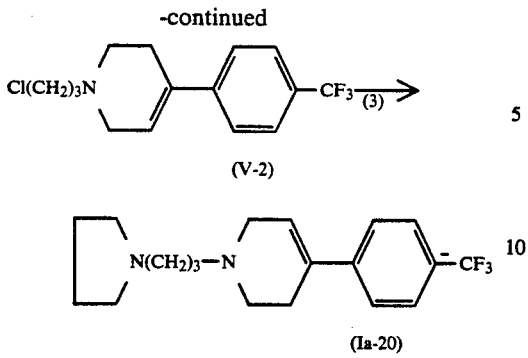

(V-2)

(Ia-20)

(1) A mixture of 5.00 g of the compound (II-2) and 2.22 ml of 3-chloro-1-propanol is stirred in the presence of 4.27 ml of $Et_3N$ at 140° C. for 8 hours. The mixture is subjected to column chromatography with silica gel, eluting with methylene chloride/methanol/ammonium=64/8/1-32/6/1 v/v. The obtained purified substance is recrystallized from ether-n-hexane to prepare 5.155 g (Yield: 75.7%) of the compound (IV-4). mp. 116.0°-116.5° C.

Anal Calcd. (%) for $C_{15}H_{20}NO_2F_3$: C, 59.31; H, 6.59; N, 4.69; F, 18.70. Found: C, 59.40; H, 6.65; N, 4.62; F, 18.79.

IR (Nujol): 3335, 3075, 2773, 1617, 1462, 1436, 1407, 1378

NMR ($CDCl_3$) δ: 1.73-1.83 (m, 4H); 2.119 (td, $J_1=13$ Hz, $J_2=4$ Hz, 2H); 2.494 (td, $J_1=12$ Hz, $J_2=3$ Hz, 2H); 2.716 (t, J=6 Hz, 2H); 3.009 (d-d, $J_1=12$ Hz, $J_2=2$ Hz, 2H); 3.836 (t, J=6 Hz, 2H); 7.612 (s, 4H)

(2) The compound (IV-4) 4.892 g is treated in the same manner as Example 19(2) to prepare 3.357 g of the compound (V-2) as an oil.

IR ($CHCl_3$): 1608, 1453, 1439, 1399, 1368(sh), 1319

NMR ($CDCl_3$): 2.036 (quint, J=7 Hz, 3H); 2.54-2.62 (m, 2H); 2.636 (t, J=7 Hz, 2H); 2.733 (t, J=6 Hz, 2H); 3.192 (q, J=3 Hz, 2H); 3.635 (t, J=7 Hz, 2H); 6.152 (quint, J=2 Hz, 1H); 7.466, 7.562 (ABq, J=8 Hz, 4H)

(3) A mixture of 1.05 g of the compound (V-2) and 1.44 ml of pyrrolidine is stirred at room temperature for 32.5 hours, and the reaction mixture is treated in the same manner as Example 19 (3) to prepare 1.15 g (Yield: 98.2%) of the objective compound (Ia-20) as crystals. The malenate is recrystallized from methanol to prepare 1.04 g (Yield: 98.2%) of colorless needles. mp. 175.0-178.0 (dec.)

Anal. Calcd. (%) for $C_{19}H_{25}N_2F_3O_2 \cdot C_4H_4O_4$: C, 57.92; H, 5.74; N, 4.97; F, 10.05. Found: C, 56.84; H, 5.83; N, 4.91; F, 9.99.

IR (Nujol): 2590, 2360, 2160, 1711, 1620, 1560, 1535(sh), 1483, 1458, 1378, 1359

NMR ($CD_3OD$): 2.119 (quint, J=3 Hz, 4H); 2.20-2.37 (m, 2H); 2.92 7 (brs, 2H); 3.28-3.50 (m, 8H); 3.566 (t, J=6 Hz, 2H); 3.971 (q, J=2 Hz, 2H); 6.266 (s, 4H); 6.295 (brs, 1H); 7.681 (s, 4H)

EXAMPLE 21

1-[3-{4-(4-methylphenyl)-1,2,5,6-tetrahydropyridin-1-yl}-propyl]pyrrolidine (Ia-21)

(II-8) →

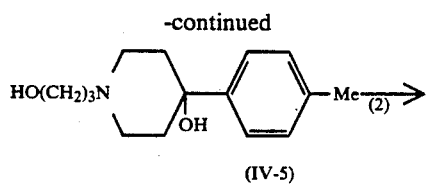

(IV-5)

(V-3)

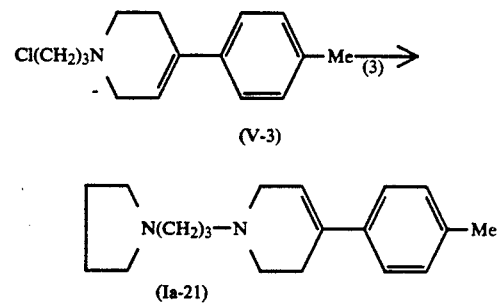

(Ia-21)

(1) A mixture of 10.20 g of the compound (II-8) and 5.51 ml of 3-chloro-1-propanol is stirred in the presence of 11 ml of $Et_3N$ at 140° C. for 5.5 hours. The reaction mixture is recrystallized from methylene chloride-ether to prepare 8.51 g (Yield: 64.0%) of the compound (IV-5). mp. 110.5°-111.5° C.

Anal Calcd. (%) for $C_{15}H_{23}NO_2$: : C, 72.01; H, 9.25; N, 5.58. Found: C, 72.25; H, 9.30; N, 5.62.

IR ($CHCl_3$): 3597, 3220, 1513, 1470, 1452, 1437, 1423, 1397

NMR ($CDCl_3$) δ: 1.67-1.81 (m, 4H); 2.087 (td, $J_1=13$ Hz, $J_2=4$ Hz, 2H); 2.337 (s, 3H); 2.479 (td, $J_1=15$ Hz, $J_2=3$ Hz, 2H); 2.693 (t, J=6 Hz, 2H); 2.952 (d, J=11 Hz, 2H); 3.828 (t, J=5 Hz, 2H); 7.168, 7.372 (ABq, J=8 Hz, 4H)

(2) A solution of 12.82 g of the compound (IV-5) in 38 ml of trifluoroacetic acid is refluxed for 3.1 hours. The reaction mixture is concentrated, and the residue is poured into aq.$NaHCO_3$. The mixture is extracted with ethyl acetate, and the organic layer is dried over $MgSO_4$ and concentrated under reduced pressure. The oily substance is subjected to column chromatography with silica gel, eluting with methylene chloride/methanol/$NH_4OH$ (128/16/1 v/v). A mixture of 870 mg of the product and 8.01 ml of thionyl chloride is stirred at room temperature for 2 hours. The excess reagent is distilled away under reduced pressure. The residue is washed with ether and dried under reduced pressure to give 1.067 g (Yield: 99.2%) of the objective compound (V-3) as a light yellowish powder.

IR ($CHCl_3$): 1600, 1510, 1460, 1410

NMR ($CDCl_3$): 2.046 (quint, J=7 Hz, 2H); 2.334 (s, 3H); 2.54, 2.64 (m, 2H); 2.629 (t, J=7 Hz, 2H); 2.723 (t, J=5 Hz, 2H); 3.173 (q, J=2 Hz, 2H); 3.630 (t, J=7 Hz, 2H); 6.023 (quint, J=2 Hz, 1H); 7.123, 7.287 (ABq, J=8 Hz, 4H)

(3) A mixture of 466 mg of the compound (V-3) and 0.78 ml of pyrrolidine is stirred at 50° C. for 3 hours and treated in the same manner as Example 19(3) to give the maleate of the objective compound (I a-21). It is recrystallized from methanol-iPrOH to prepare 225 mg (Yield: 42.5%) of the compound (I a-21) as needles. mp. 180.0°-181.0° C. (dec.)

Anal Calcd. (%) for $C_{19}H_{28}N_2 \cdot 2C_4H_4O_4$: : C, 62.84; H, 6.99; N, 5.48. Found: C, 62.78; H, 7.02; N, 5.42.

EXAMPLE 22-29

The compound (V-1), (V-2) and (V-3), each of which were obtained in Step 1 of Example 19-21, are reacted with amine (VIII) in the same manner as Step 3 in Example 19-21 to prepare the compound (I a). The reaction conditions and physical constants are shown in table 5 and 6.

TABLE 5

$$HN\underset{OH}{\diagdown}\text{—PhX} \xrightarrow{(1)} OH(CH_2)_3N\underset{OH}{\diagdown}\text{—PhX} \xrightarrow{(2)} Cl(CH_2)_3N\diagdown\text{—PhX} \xrightarrow[(3)]{RH\,(VIII)} R(CH_2)_3N\diagdown\text{—PhX}$$

(II)  (IV)  (V)  (Ia)

| Ex. No. | starting material | RH | reaction condition | purification condition | product mg (%) |
|---|---|---|---|---|---|
| 22 | (V-1) 0.628 g | HN(i-Bu)$_2$ 3.76 ml | 33 hours reflux | CH$_2$Cl$_2$/MeOH = 49/1–19/1 | Ia-22*[1] 685 mg (51.1%) |
| 23 | (V-2) 0.602 g | HN(i-Bu)$_2$ 1.50 g | 32 hours reflux | CH$_2$Cl$_2$/MeOH = 49/1–19/1 | Ia-23*[1] 338 mg (27.1%) |
| 24 | (V-3) 0.517 g | HN(i-Bu)$_2$ 1.36 g | 20 hours reflux | CH$_2$Cl$_2$/MeOH = 49/1 | Ia-24*[1] 457 mg (38.4%) |
| 25 | (V-3) 0.924 g | 1,2,3,4-tetrahydroquinoline 2.32 ml | 150° C. 8.15 hours | toluene/ acetone = 19/1–9/1 | Ia-25*[1] 930 mg (54.4%) |
| 26 | (V-3) 0.624 g | 1,2,3,4-tetrahydroisoquinoline | 150° C. 4.1 hours | CH$_2$Cl$_2$/MeOH = 19/1 | Ia-26*[1] 963 mg (66.6%) |
| 27 | (V-2) 1.02 g | sodium isoindoline *[2] | 100° C. 25 hours (in DMF) | toluene/ acetone = 3/11/1 | Ia-27*[1] 266 mg (15.3%) |
| 28 | (V-2) 0.645 g | H,N-i-Bu 1.1 ml | 15.6 hours reflux | CH$_2$Cl$_2$:MeOH: NH$_4$OH =64/8/1 | Ia-28 461 mg (63.8%) |
| 29 | (V-1) 0.828 g | 1,2,3,4-tetrahydroisoquinoline | 150° C. 3 hours | CH$_2$Cl$_2$/MeOH = 29/1–19/1 | Ia-29*[1] 773 mg (70.2%) |

*[1]: separated as maleate
*[2]: prepared by the reaction with 492 mg of isoindoline and 162 mg of 60% NaH in 5 ml of DMF at 100° C. for 1 hour.

TABLE 6

| Compd. No. | mp. (°C.) Rec. sol.*[1] | Anal Cald. (%) Found (%) | IR (cm$^{-1}$) | NMR ($\delta$) (200MHz) |
|---|---|---|---|---|
| I a-22 | (maleate) 176.5~178.0 (MeOH—Et$_2$O) needleshaped crystals | C$_{26}$H$_{44}$N$_2$O$_2$·C$_4$H$_4$O$_4$ C, 63.46 (63.68) H, 8.02 (8.18) N, 6.83 (6.75) F, 7.98 (8.54) | (Nujol) 2620, 2510, 1690 1657, 1618, 1579 1533, 1488, 1460 1409, 1378 | (CD$_3$OD) 1.083(d, J=7Hz, 12H); 1.314(s, 9H); 2.153(7tct. J=7Hz, 2H); 2.20–2.37(m, 2H); 2.913(brs, 2H); 3.042(d, J=7Hz, 4H); 3.25–3.37(m, 4H); 3.588(t, J=6Hz, 2H); 3.974(s, 2H); 6.131(s, 1H); 6.272(s, 4H); 7.419(s, 4H) |
| I a-23 | (maleate) 135.0~136.5 (MeOH—Et$_2$O) needleshaped crystals | C$_{25}$H$_{35}$N$_2$F$_3$O$_2$·C$_4$H$_4$O$_4$ C, 59.12 (59.23) H, 6.76 (6.89) N, 4.35 (4.46) F, 9.05 (9.07) | (Nujol) 2420, 1707, 1616 1572, 1485, 1456 1377 | (CD$_3$OD) 1.071(d, J=7Hz, 12H); 2.05–2.35(m, 4H); 2.90–3.30(m, 4H); 3.20–3.30(m, 4H); 3.559(brs, 2H); 3.972(brs, 2H); J=7Hz, 2H); 2.54–2.61(m, 2H); 2.747(t, J=5Hz, 2H); 6.260(s, 5H); 7.674(s, 4H) |
| I a-24 | (maleate) 140.5~142.5 (MeOH—Et$_2$O) needleshaped crystals | C$_{23}$H$_{38}$N$_2$·C$_4$H$_4$O$_4$ C, 64.67 (64.79) H, 7.99 (8.07) N, 4.69 (4.87) | (Nujol) 2710, 2500, 1706 1572, 1480, 1455 1375 | (CDCl$_3$) 0.872(d, J=7Hz, 12H); 1.685(quint, J=7Hz, 4H); 2.059(d, J=7Hz, 4H); 2.329(m, 3H); 2.33–2.60(m, 6H); 2.712(t, J=5Hz, 2H); 3.161(q, J=3Hz, 2H); 6.021(quint, J=2Hz, 1H); 7.116, 7.283(ABq, J=9Hz, 4H) |
| I a-25 | (maleate) 148.0~150.0 (iPrOH—Et$_2$O) | C$_{24}$H$_{39}$N$_2$O$_2$·C$_4$H$_4$O$_4$ C, 72.65 (72.70) H, 7.36 (7,41) | (Nujol) 2720, 2575(sh) 2490(sh), 2330, | (CD$_3$OD) 1.80–2.01(m, 4H); 2.331(s, 3H); 2.48–2.63(m, 4H); 2.712(t, J=7Hz, 2H); 2.747(t, J=7Hz, 2H); 3.162(q, |

TABLE 6-continued

| Compd. No. | mp. (°C.) Rec. sol.*1 | Anal Cald. (%) Found (%) | IR (cm$^{-1}$) | NMR (δ) (200MHz) |
|---|---|---|---|---|
| | | N, 6.11 (6.06) | 1708, 1652, 1600 1571, 1502, 1459 (Nujol) | J=3Hz, 2H); 3.283(t, J=6Hz, 2H); 3.329(t, J=7Hz, 2H); 6.026(quint, J=2Hz, 1H); 6.50–6.64(m, 2H); 6.91–7.32(m, 6H) (CDCl$_3$) |
| I a-26 | (maleate) 191.0~192.0 (MeOH—H$_2$O) needleshaped crystals | C$_{24}$H$_{30}$N$_2$O$_2$.C$_4$H$_4$O$_4$ C, 66.48 (66.42) H, 6.61 (6.62) N, 4.92 (4.84) | 3030, 2720, 2278 1711, 1623, 1572 1532, 1513(sh), 1485, 1463, 1435 | 1.322(s, 9H); 1.76–1.94(m, 8H); 2.262(t-d, J$_1$=14Hz, J$_2$=4Hz, 2H); 2.50–2.65(m, 4H); 2.951(d, J=11Hz, 2H); 3.30–3.39(m, 4H); 5.738(brs, 1H); 7.378, 7.418(ABq, J=8Hz, 4H) |
| I a-27 | (maleate) 152.5~154.0 (MeOH—Et$_2$O) needleshaped crystals | C$_{23}$H$_{23}$F$_3$N$_2$O.C$_4$H$_4$O$_4$ C, 62.64 (62.79) H, 5.29 (5.27) N, 5.48 (5.42) F, 11.00 (11.03) | (CHCl$_3$) 2700–1750 (br); 1695, 1663, 1619 1532, 1463, 1412 1378, 1358 | (CD$_3$OD) 2.236(quint, J=7Hz, 2H); 2.934(brs, 2H); 3.334(t, J=7Hz, 2H); 2.369(t, J=5Hz, 2H); 3.808(t, J=7Hz, 2H); 4.010(s, 2H); 4.606 (s, 2H); 6.230(brs, 2H); 6.298(brs, 1H); 7.51–7.81(m, 9H) |
| I a-28 | (maleate) 182.5~184.0 (MeOH—Et$_2$O) needleshaped crystals | C$_{19}$H$_{27}$N$_2$F$_3$.C$_4$H$_4$O$_4$ — | (Nujol) 3483, 2723, 2679 2587, 2415, 1703 1618, 1579, 1478 1460, 1412, 1382 | (CDCl$_3$) 0.952(d, J=7Hz, 6H); 2.093(quint. J=7Hz, 3H); 2.636(brs, 2H); 2.727(d, J=7Hz, 2H); 2.771(t, J=6Hz, 2H); 2.898(t, J=6Hz, 2H); 3.149(t, J=6Hz, 2H); 3.29–3.33(m, 2H); 6.184(quint. J=2Hz, 1H); 7.474, 7.587(ABq, J=8Hz, 4H) |
| I a-29 | (maleate) 183.5~185.0 (CHCl$_3$—MeOH) needleshaped crystals | C$_{27}$H$_{36}$N$_2$.2C$_4$H$_4$O$_4$. 1/10H$_2$O C, 67.29 (67.59) H, 7.08 (7.16) N, 4.56 (4.50) | (Nujol) 2340, 1708, 1619 1568, 1528(sh), 1485, 1461 | (CD$_3$OD) 1.330(s, 9H); 2.424(brs, 2H); 2.867(brs, 2H); 3.204(brs, 2H); 3.370(brs, 4H); 3.544(brs, 4H); 3.948(s, 2H); 4.403(s, 2H); 6.060(s, 1H); 6.252(s, 4H); 7.15–7.44(m, 8H) |

*1: a solvent for recrystallization

EXAMPLE 30

1-[(3-methylamino)propyl]-4-(4-tert-butylphenyl)-1,2,5,6-tetrahydropyridine (I a-30)

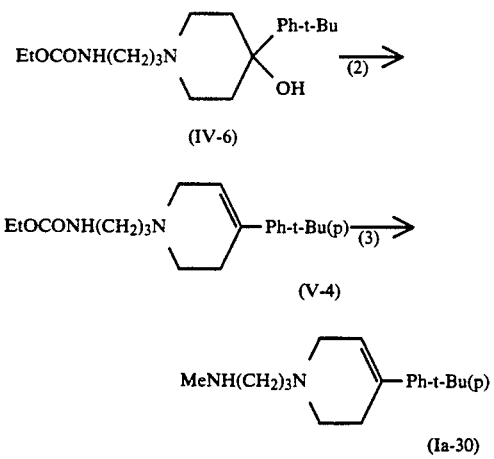

(1) A solution of 3.60 g of the compound (II-6) and 2.80 g of 1-ethoxycarbonylamino-3-chloropropane in 30 ml of DMF is reacted in the presence of 4.26 g of K$_2$CO$_3$ and 3.46 g of NaI at 105°–110° C. for 6 hours. The reaction mixture is poured into ice water and extracted with ethyl acetate. The ethyl acetate layer is washed with water, dried over MgSO$_4$ and evaporated under reduced pressure. The residue is subjected to column chromatography with silica gel, eluting with methylene chlorde/methanol (10/1–5/1 v/v) to give 4.60 g (Yield: 82.0%) of the compound (IV-6) as crystals. Recrystallization from methylene chloride-ether gives colorless needles. mp. 111.5°–113.0° C.

Anal Calcd. (%) for C$_{21}$H$_{34}$N$_2$O$_3$. 1/5H$_2$O: : C, 68.92; H, 9.37; N, 7.78. Found: C, 68.89; H, 9.47; N, 7.65.

IR (Nujol): 3320, 1715, 1700, 1535

NMR (CDCl$_3$) δ: 1.242 (t, J=7 Hz, 3H); 1.320 (s, 9H); 1.66–1.84 (m, 4H); 2.210 (td, J$_1$=13 Hz, J$_2$=4 Hz, 2H) 2.45–2.60 (m, 4H); 2.877 (d, J=12 Hz, 2H); 3.286 (q, J=6 Hz, 2H); 4.103 (q, J=7 Hz, 2H); 5.929 (brs, 1H); 7.376,7.443 (ABq, J=8 Hz, 4H)

(2) A solution of 4.30 g of the compound (IV-6) obtained above in 35 ml of trifluoroacetic acid is refluxed for 5 hours and treated in the same manner as Example 7(2) to prepare 4.05 g (Yield: 99.0%) of the compound (V -4) as an oil.

(3) To a suspension of 146 mg of lithium aluminium hydride in 15 ml of dry ether is added dropwise a solution of 530 mg of the compound (V-4) in 15 ml of THF under stirring. After reflux for 8 hours, the excess reagents are decomposed by careful addition of aq. NaOH and filtered off. The resulting organic layer is dried and evaporated under reduced pressure to prepare 420 mg (Yield: 95.2%) of the compound (I a-30) as an oil.

IR (CHCl$_3$): 3290, 1602, 1510, 1470, 1445

NMR (CDCl$_3$): 1.321 (s, 9H); 1.780 (quint, J=7 Hz, 2H); 2.444 (s, 3H); 2.48–2.62 (m, 2H); 2.532 (t, J=7 Hz, 2H); 2.672 (t, J=7 Hz, 2H); 3.152 (q, J=3 Hz, 2H); 6.039 (quint, J=2 Hz, 1H); 7.333 (s, 4H)

EXAMPLE 31

1-[N-methyl-N-[3-{4-(4-tert-butylphenyl)-1,2,5,6-tetrahydropyridin-1-yl}propylcarbamoyl]]-2-oxopyrrolidine (I a-31)

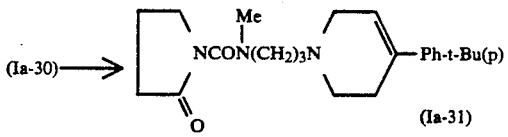

A mixture of 400 mg of the compound (I a-30) obtained in Example 30 and 280 mg of 1-phenoxycarbonyl-2-oxopyrrolidine is heated at 115° C. for 2 hours. The reaction mixture is subjected to column chromatography with silica gel; eluting with toluene/ethyl acetate (1/1)-methylene chloride/methanol (20/1) to prepare 370 mg (Yield: 68.5%) of the compound (I a-31) as an oil. The tosylate is recrystallized from ethyl acetate/methanol to prepare needles. mp. 128.0°–134.0° C.

Anal Calcd. (%) for C$_{24}$H$_{35}$N$_3$O$_2$. C$_7$H$_8$O$_3$S. H$_2$O: C, 63.51; H, 7.56; N, 7.16; S, 5.37. Found: C, 63.35; H, 7.72; N, 7.15; S, 5.45.

IR (Nujol) cm$^{-1}$: 3570, 3500, 2740, 2630, 1720, 1690, 1675(sh), 1663, 1475, 1120, 1033

NMR (CDCl$_3$) δ: 1.314 (s, 9H); 1.895 (quint, J=7 Hz, 2H); 2.071 (quint, J=7 Hz, 2H); 2.454 (t, J=8 Hz, 2H); 2.50-2.60 (m, 4H); 2.720 (t, J=5 Hz, 2H); 2.995 (s, 3H); 3.174 (q, J=3 Hz, 2H); 3.461 (t, J=7 Hz, 2H); 3.735 (t, J=7 Hz, 2H); 6.024 (quint, J=2 Hz, 1H); 7.244, 7.348 (ABq, J=8 Hz, 4H)

EXAMPLE 32

1-[(3-methylamino)propyl]-4-(4-phenylphenyl-1,2,5,6-tetrahydropyridine (I a-32)

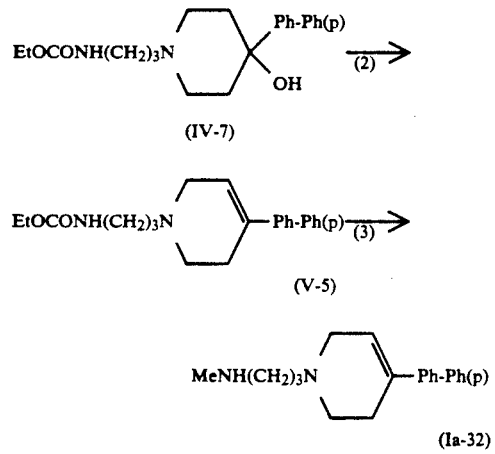

(1) A solution of 3.20 g of the compound (II-5) and 2.30 g of 1-ethoxycarbonylamino-3-chloropropane in 30 ml of DMF is reacted in the presence of 3.48 g of K$_2$CO$_3$ and 2.83 g of NaI at 105° C. for 41 hours. The reaction mixture is poured into ice water and extracted with ethyl acetate. The ethyl acetate layer is washed with water, dried over MgSO$_4$ and evaporated under reduced pressure. The residue is subjected to column chromatography with silica gel, eluting with methylene chloride/methanol (10/1-5/1v/v). The resulting purified substance is recrystallized from methylene chloride to prepare 2.46 g (Yield: 51.0%) of the compound (IV-7). mp. 138.0°-139.0° C.

Anal Calcd. (%) for C$_{23}$H$_{30}$N$_2$O$_3$: C, 72.22; H, 7.84; N, 7.30. Found: C, 72.22; H, 7.91; N, 7.32.

IR (CHCl$_3$) cm$^{-1}$: 3600, 3450, 1705, 1602, 1512, 1490

NMR (CDCl$_3$) δ: 1.240 (t, J=7 Hz, 3H); 1.60-1.80 (m, 4H); 1.830 (s, 1H); 2.195 (t-d, J$_1$=13 Hz, J$_2$=4 Hz, 2H); 2.480 (d-d, J$_1$=14 Hz, J$_2$=2 Hz, 2H); 2.524 (t, J=7 Hz, 2H); 2.850 (d, J=14 Hz, 2H); 3.280(q, J=6 Hz, 2H); 4.101 (q, J=7 Hz, 2H); 6.962 (brs, 1H); 7.25-7.70 (m, 9H) 9H)

(2) A solution of 2.29 g of the compound (IV-7) in 25 ml of trifluoroacetic acid is refluxed for 9.5 hours and treated in the same manner as Example 7 (2) to prepare 2.08 g (Yield: 95.3%) of the compound (V-5). mp. 135.0°-138.0° C.

(3) To a solution of 1.80 g of the compound (V-5) in 26 ml of THF is added dropwise 375 mg of lithium alminium hydride. After reflux for 8 hours, the reaction mixture is treated in the same manner as Example 29 (3) to prepare (I a-32) as an oil.

EXAMPLE 33

1-[3-{4-(4-phenylphenl)-1,2,5,6-tetrahydropyridin-1-yl} propylmethylcarbamoyl]-2-oxopyrrolidine (I a-33)

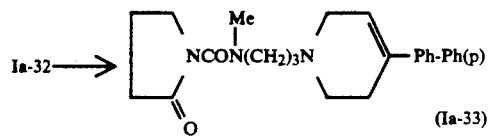

To the compound (I a-32) obtained Example 32 is added dropwise 810 mg of 1-phenoxycarbonyl-2-oxopyrrolidine, and the mixture is heated at 115°-120° C. for 5 hours. The reaction mixture is subjected to column chromatography with silica gel, eluting with methylene chloride/methanol (20/1 v/v) to prepare 650 mg (Yield: 31.5%) of the compound (I a-33). The oxalate is recrystallized from i-PrOH to give needles. mp. 186.0°-187.0° C. (dec.)

Anal Calcd. (%) for C$_{26}$H$_{31}$N$_3$O$_2$.C$_2$H$_2$O$_4$.½H$_2$O: C, 64.71; H, 6.52; N,7.97. Found: C, 65.10; H, 6.63; N,8.13.

IR (Nujol): 3500(br), 2720, 2600, 1720, 1665, 1485, 1455, 1405, 1405, 1375

NMR (CDCl$_3$) δ: 1.900 (quint, J=7 Hz, 2H); 2.107 (quint, J=7 Hz, 2H); 2.455 (t, J=8 Hz, 2H); 2.55-2.64 (m, 4H); 2.741 (t, J=5 Hz, 2H); 3.002 (s, 3H); 3.198 (q, J=3 Hz, 2H); 3.469 (t, J=7 Hz, 2H); 3.737 (t, J=7 Hz, 2H); 6.124 (quint, J=2 Hz, 1H) 7.3-7.6 (m, 9H)

EXAMPLE 34

1-[3-(N-methyl-N-isobutyl)aminopropyl]-4-(4-trifluoromethylphenyl)-1,2,5,6-tetrahydropyridine (I a-34)

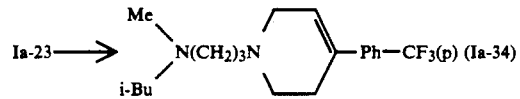

A mixture of 342 mg of the compound (I a-23), 1 ml of formaldehyde, and 1 ml of formic acid is stirred at 70° C. for 3 hours and 40 minutes. The reaction mixture is concentrated, and the residue is poured into aq.NaHCO$_3$. The solution is extracted with methylene chloride-methanol, and the organic layer is dried over MgSO$_4$ and evaporated under reduced pressure. The resulting oily substance is subjected to column chromatography with silica gel, eluting with methylene chloride/methanol (19/1-5/1 v/v) to prepare 252 mg of the objective compound (I a-34). The maleate is recrystallized from ethnol-ether to prepare 325 mg (Yield: 55.2%) of colorless needles. mp. 182.0°-183.5° C.

Anal Calcd. (%) for C$_{20}$H$_{29}$N$_2$F$_3$.2C$_4$H$_4$O$_4$: C, 57.16; H, 6.32; N, 4.82; F, 9.46. Found: C, 57.33; H, 6.36; N, 4.78; F, 9.72.

IR (Nujol): 2360, 1708, 1621, 1570, 1533, 1481, 1460, 1447(sh), 1377, 1359

NMR (CDCl$_3$): 0.938 (d, J=7 Hz, 6H); 1.826 (quint, J=7 Hz, 3H); 2.212 (d, J=7 Hz, 2H); 2.309 (s, 3H); 2.513 (t, J=7 Hz, 2H); 2.548 (t, J=7 Hz, 2H); 2.58, 2.63 (m, 2H); 2.747 (t, J=5 Hz, 2H); 3.208 (q, J=3 Hz, 2H); 6.161 (quint, J=2 Hz, 1H); 7.474, 7.567 (ABq, J=8 Hz, 4H)

EXAMPLE 35

4-[3-{4-(4-tert-butylphenyl)-1,2,5,6-tetrahydropyridin-1-yl}propyl]morpholine (I a-35)

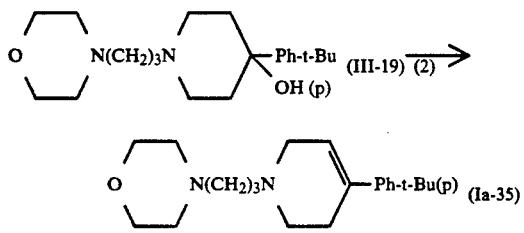

(1) A mixture of 1.09 g of the compound (IV-2) obtained in Example 18 and 1.4 g of morpholine is refluxed for 4 hours. After removal of the excess reagent under reduced pressure, the residue is poured into aq.Na$_2$SO$_4$ and evaporated. The residue is purified by column chromatography with silica gel, eluting with mthylene chloride/methanol (20/1 v/v). The hydrochloride of the compound (III-19) is crystallized from methylene chloride-ether to prepare 850 mg (Yield: 66.3%) of needles. mp. 242° C. (dec.)

NMR (CDCl$_3$.CD$_3$OD=10/1): 1.307 (s, 9H); 2.10-2.22 (m, 2H); 2.48-2.55 (m, 4H); 2.760 (td, J$_1$=15 Hz, J$_2$=4 Hz, 2H); 3.06-3.15 (m, 4H); 3.25-3.50 (m, 4H); 3.731 (t, J=5 Hz, 4H); 7.387, 7.454 (ABq, J=9 Hz, 4H)

(2) A solution of 880 mg of the compound (III-19) in 10 ml of trifluoroacetic acid is refluxed for 8 hours and evaporated under reduced pressure. The residue is poured into aq. sodium hydrogencarbonate, and extracted with methylene chloride. The organic layer is washed with saline, dried over Na$_2$SO$_4$ and evaporated. The residue is purified by column chromatography followed by crystallization as the maleate. Recrystallization from methanol gives 760 mg (Yield: 97.5%) of redish needles. mp. 213.0°-214.5° C. (dec.)

Anal Calcd. (%) for C$_{22}$H$_{34}$N$_2$O.2C$_4$H$_4$O$_4$: C, 62.63; H, 7.35; N, 4.93. Found: C, 62.70; H, 7.37; N, 4.87.

IR (Nujol): 2300 (br); 1717, 1622, 1675, 1535, 1500, 1465, 1458, 1450(sh)

NMR (CDCl$_3$): 1.314 (s, 9H); 1.783 (quint, J=7 Hz, 2H); 2.36, 2.63 (m, 8H); 2.709 (t, J=5 Hz, 2H); 3.164 (q, J=3 Hz, 2H); 3.725 (t, J=5 Hz, 2H); 6.031 (quint, J=1 Hz, 1H); 7.330 (s, 4H)

EXAMPLE 36-71

The reaction is performed in the same manner as Example 1 to prepare the compound (I a). The reaction conditions are shown in Table 7 and 8. Further the physical constants of the compound (I a) obtained in Example 36-71 are shown in Table 9.

TABLE 7

(Step 1)

$$\text{HN}\underset{\text{OH}}{\bigcirc}\xrightarrow{\text{PhX}}\xrightarrow[\text{R(CH}_2)_n\text{Y (VI)}]{\text{Step 1}} \text{R(CH}_2)_n\text{—N}\underset{\text{OH}}{\bigcirc}\xrightarrow{\text{PhX}}\xrightarrow{\text{Step 2}}\text{R(CH}_2)_n\text{—N}\underset{}{\bigcirc}\text{—PhX}$$

(III)    (Ia)

| Exam. No. | starting material X= | R(CH$_2$)nY(VI) | DMF (ml) | K$_2$CO$_3$ (g) | NaI (g) | reaction condition (1) (°C. hr.) | purification condition | g (%) Compd. No. | m.p. (°C.) | IR (cm$^{-1}$) |
|---|---|---|---|---|---|---|---|---|---|---|
| 36 | Me (p) 2.50 g (II-8) | NCOHN(CH$_2$)$_2$Cl 2.49 g (VI-7) | 35 | 4.53 | 2.95 | 105–110 7 hr. | CH$_2$Cl$_2$/MeOH = 10/1 | 3.46 (76.4) (III-20) | 116.0~117.0 | (CHCl$_3$) 3600, 3320, 1713, 1688 (sh), 1680, 1545, 1490 |
| 37 | Me (p) 2.34 g (II-8) | NCOHN(CH$_2$)$_3$Cl 2.50 g (VI-1) | 25 | 4.21 | 2.74 | 105 6 hr. | toluene/ethyl acetone = 20/1–10/1 | 3.07 (70.0) (III-21) | 143.5~144.5 | (CHCl$_3$) 3600, 3320, 1715, 1680, 1608, 1545, 1618, 1550–1520 |
| 38 | Me (m) 1.85 g (II-9) | (VI-1) 2.35 g | 30 | 3.18 | 2.59 | 105–110 8 hr. | CH$_2$Cl$_2$/MeOH = 10/1 | 1.70 (49.0) (III-22) | — | (CHCl$_3$) 3600, 3320, 1715, 1680, 1608, 1545, 1490, 1470 |
| 39 | Me (o) 2.50 g (II-10) | (VI-1) 2.68 g | 35 | 4.53 | 2.95 | 105–110 7 hr. | CH$_2$Cl$_2$/MeOH = 10/1 | 3.18 (67.5) (III-23) | — | (CHCl$_3$) 3600, 3320, 1712, 1680, 1600, 1545, 1489, 1470, 1460 |
| 40 | 3,4-di-Me 2.10 g (II-11) | (VI-1) 2.09 g | 35 | 2.82 | 2.29 | 105 7 hr. | CH$_2$Cl$_2$/MeOH = 10/1 | 2.56 (67.2) (III-24) | — | — |
| 41 | 3,5-di-Me 2.82 g (II-12) | (VI-1) 2.81 g | 35 | 3.79 | 3.08 | 105° C. 6 hr. | CH$_2$Cl$_2$/MeOH = 10/1 | 3.81 (74.4) (III-25) | — | (CHCl$_3$) 3595, 3310, 1715, 1680, 1590, 1565, 1545, 1489, 1470, 1460 |
| 42 | Cl (m) 2.70 g (II-13) | (VI-1) 2.49 g | 30 | 4.18 | 2.72 | 105–110° C. 7 hr. | CH$_2$Cl$_2$/MeOH = 20/1–10/1 | 3.78 (81.8) (III-26) | 90.5~91.5 | (CHCl$_3$) 3600, 3320, 1713, 1658, 1595, 1545, 1490, 1470, 1460 |
| 43 | Cl (m) 2.70 g (II-13) | (VI-7) 2.31 g | 30 | 4.18 | 2.72 | 105–110° C. 7 hr. | CH$_2$Cl$_2$/MeOH = 10/1 | 3.30 (74.3) (III-27) | 94.0~98.0 | (Nujol) 3280, 2720–2520, 1713, 1685, 1600, |

TABLE 7-continued

| | | | | | | | | |
|---|---|---|---|---|---|---|---|---|
| 44 | Cl (o) 2.50 g (II-14) | (VI-1) 2.42 g | 30 | 4.08 | 2.65 | 105–110 6 hr. | ethyl acetate/ toluene = 1/1 CH$_2$Cl$_2$/MeOH = 15/1 | 2.10 (46.7) (III-28) | — | (sh), 1588, 1560 (CHCl$_3$) 3580, 3320, 1715, 1680, 1547 |
| 45 | Cl (o) 1.45 g (II-14) | (VI-7) 1.28 g | 20 | 2.32 | 1.51 | 105–110 6 hr. | CH$_2$Cl$_2$/MeOH = 15/1 | 0.840 (34.1) (III-29) | — | (CHCl$_3$) 3580, 3220, 1715, 1680, 1545(sh), 1540(sh), 1525 |
| 46 | 3,5-diCl 3.86 g (II-15) | (VI-1) 3.0 g | 35 | 4.04 | 3.28 | 105° C. 7.0 hr. | CH$_2$Cl$_2$/MeOH = 10/1 | 5.25 (86.8) (III-30) | 138.0~ 140.0 | (CHCl$_3$) 3595, 3310, 1715, 1680, 1590, 1565, 1545 |
| 47 | Br (p) 2.57 g (II-16) | (VI-1) 1.96 g | 25 | 2.64 | 2.15 | 105° C. 8 hr. | CH$_2$Cl$_2$/MeOH = 10/1 | 3.16 (77.9) (III-31) | — | (CHCl$_3$) 3590, 3310, 1713, 1680, 1545, 1489, 1460 |
| 48 | F (p) 4.00 g (II-17) | (VI-1) 4.20 g | 50 | 7.08 | 4.61 | 105–110° C. 6.0 hr. | CH$_2$Cl$_2$/MeOH = 15/1–8/1 | 4.96 (66.5) (III-32) | 102.5~ 104.0 | (CHCl$_3$) 3600, 3320, 1713, 1680, 1545, 1510, 1489 |
| 49 | F (p) 2.30 g (II-17) | (VI-7) 2.25 g | 25 | 4.08 | 2.65 | 105° C. 6 hr. | CH$_2$Cl$_2$/MeOH = 10/1 | 2.78 (67.4) (III-33) | 118.0~ 119.0 | (CHCl$_3$) 3600, 3320, 1713, 1680, 1605, 1545, 1510, 1489 |
| 50 | CF$_3$ (m) Cl (p) 3.50 g (II-18) | (VI-1) 2.56 g | 50 | 3.46 | 2.81 | 105–110° C. 9 hr. | CH$_2$Cl$_2$/MeOH = 20/1–10/1 | 5.20 (92.9) (III-34) | 238.5~ 240.5 | (Nujol) 3350, 2650, 2525, 2450, 1720, 1677, 1557 |
| 51 | CF$_3$ (m) Cl (p) 3.50 g (II-18) | (VI-7) 2.38 g | 50 | 3.46 | 2.81 | 105–110 15 hr. | CH$_2$Cl$_2$/MeOH = 20/1–10/1 | 4.75 (87.6) (III-35) | 255.0~ 257.0 | (Nujol) 3400, 3260, 2640, 2500, 2430, 1713, 1672, 1547 |

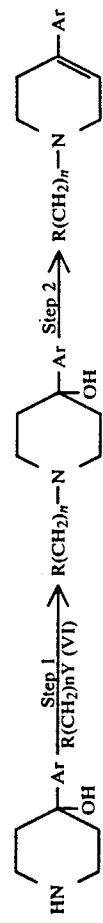

| | | | | | | | | |
|---|---|---|---|---|---|---|---|---|
| 52 | 2.80 g (II-19) *1 | (VI-1) 2.64 g | 36 | 4.46 | 2.90 | 105–110 8 days | CH$_2$Cl$_2$/MeOH = 10/1 | 3.55 (71.3) (III-36) | 122.0~ 123.0 | (CHCl$_3$) 3590, 3320, 1713, 1680, 1544, 1490, 1470, 1460(sh), 1450 |
| 53 | 2.10 g (II-20) | (VI-1) 1.70 g | 30 | 1.73 | 2.50 | 105 7 days | CH$_2$Cl$_2$/MeOH = 10/1 | 3.00 (85.7) | — | (CHCl$_3$) 3600, 3320, 1712, |

TABLE 7-continued

| | *2 | | | | | | | (III-37) | 1680, 1543 |
|---|---|---|---|---|---|---|---|---|---|
| 54 | Cl (p) 1.00 g (II-21) | (VI-5) 1.03 g | 10 | 1.63 | (Ia-52) 1.06 | 90 12 hr. | CH₂Cl₂/MeOH = 20/1–10/1 | 1.37 (74.0) (III-38) | 111.5–112.0 | (CHCl₃) 3600, 3280, 1702, 1698, 1530, 1645, 1495, 1480, 1463 |
| 55 | Cl (p) 2.0 g (II-21) | NCONH(CH₂)₂Cl (VI-8) 2.32 g | 25 | 3.26 | (Ia-53) 2.12 | 90–95 10 hr. | CH₂Cl₂/MeOH = 10/1 | 1.75 (48.7) (III-39) | 128.0–129.0 | (CHCl₃) 3600, 3280, 1525, 1492, 1480, 1460 |
| 56 | t-Bu (p) 1.00 g (II-6) | N(CH₂)₃Cl (VI-9) 0.90 g | 10 | K₂CO₃ 1.184 | NaI 0.96 | 100° C. 3 hr. | CH₂Cl₂/MeOH/ NH₄OH = 64/8/1 | 1.13 (71.0) (III-40) | — | (CHCl₃) 3590, 2498, 1510, 1470, 1455, 1399 |
| 57 | Me (p) 1.00 g (II-8) | (VI-9) 1.10 g | 10 | K₂CO₃ 1.45 | NaI 1.18 | 100° C. 2.5 hr. | CH₂Cl₂/MeOH/ NH₄OH = 64/8/1 | 1.445 (83.6) (III-41) | — | (CHCl₃) 3580, 2498, 1510, 1463, 1450, 1375 |
| 58 | tBu (p) 0.81 g (II-6) | MeN N(CH₂)₃Cl 0.67 g | 12 | K₂CO₃ 0.96 | NaI 0.78 | 100° C. 2.7 hr. | CH₂Cl₂/MeOH/ NH₄OH = 64/8/1 | 1.053 (84.6) (III-42) | — | (CHCl₃) 3580, 2498, 1510, 1463, 1450, 1375 |

TABLE 7-continued

| Exam. No. | (II) | R(CH₂)nY (VI) | K₂CO₃ g | Et₃N | NaI g | DMF ml | reaction condition | | purification condition (I) | g (%) (III) | m.p. (°C.) |
|---|---|---|---|---|---|---|---|---|---|---|---|
| 59 | tBu (p) 0.727 g (II-6) | 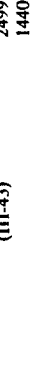 N(CH₂)₃Cl 0.66 g | K₂CO₃ 0.86 | | NaI 0.70 | 11 | 100° C. 2.5 hr. | | — | 0.736 (62.4) (III-43) | — |
| 60 | Me (p) 10.2 g (II-8) | NO(CH₂)₃Cl (VI-12) 5.81 ml | | Et₃N 11.16 ml | | — | 140° C. 4.0 hr. | | CH₂Cl₂/MeOH = 9/1 | 8.51 g (64.0) (III-44) | 183.0~ 185.0 |
| 61 | Me (p) 0.964 g (II-8) | (VI-3) 964 mg | K₂CO₃ 1.40 g | | NaI 1.14 g | 15 | 105° C. 5.75 hr. | | CH₂Cl₂/MeOH = 9/1 CH₂Cl₂/MeOH/ NH₄OH = 64/8/1 | 0.74 g (41.7) (III-45) | 170.0~ 172.5 |
| 62 | Ph (p) 0.93 g (II-5) | (VI-3) 0.70 g | K₂CO₃ 1.02 g | | NaI 0.93 g | 11 | 105° C. 5.75 hr. | | CH₂Cl₂/MeOH = 10/1 CH₂Cl₂/MeOH/ NH₄OH = 128/16/1 | 616 mg (41.0) (III-46) | 225.0~ 228.0 (dec.) |
| 63 | CF₃ (p) 1.50 g (II-2) |  NCC(CH₃)₃Cl (VI-13) 1.50 g | K₂CO₃ 1.69 g | | NaI 1.38 mg | 20 | 105° C. 8.0 hr. | | CH₂Cl₂MeOH = 20/1-10/1 | 0.56 g (19.1) (III-47) | 142.5- 144.0 |
| 64 | Me (p) 1.44 g (II-8) | NCC(CH₂)₂Cl (VI-14) 1.63 g | CH₂Cl₂ 20 | Et₂N 1.16 ml | | | room temperature 92 hr. | | CH₂Cl₂MeOH/ NH₄OH = 128/10/1 ~ 64/8/1 | 2.11 g (88.4) (III-48) | — |
| 65 | (II-6) 3.67 g | (VI-7) 3.00 g | 4.35 | | 3.54 | 45 | 105° C., 8 hr. | | CH₂Cl₂/MeOH = 29/1~9/1 | 4.90 (73.5) (III-49) | 219.0~ 222.0 |
| 66 | (II-1) 3.60 g | (VI-7) 3.07 g | 4.04 | | 3.28 | 45 | 105° C., 9 hr. | | CH₂Cl₂/MeOH = 10/1 | 5.57 (95.0) (III-50) | 232.0~ 239.0 |
| 67 | (II-2) 4.70 g | (VI-7) 3.34 g | 4.63 | | 3.93 | 45 | 105° C., 9 hr. | | CH₂Cl₂/MeOH = 15/1~10/1 | 6.11 (87.4) (III-51) | 266.0~ 268.0 |
| 68 | (II-16) 3.36 g | (VI-7) 2.50 g | 3.62 | | 2.95 | 35 | 105° C., 12 hr. | | CH₂Cl₂/MeOH = 10/1 | 4.50 (83.7) (III-52) | 230.0~ 232.0 |
| 69 | (II-5) 3.99 g | (VI-7) 3.00 g | 4.35 | | 3.54 | 45 | 105° C., 8 hr. | | CH₂Cl₂/MeOH = 39/1~19/1 | 5.61 (80.3) (III-53) | 233.0~ 238.0 |
| 70 | (II-3) 3.45 g | (VI-7) 3.00 g | 4.35 | | 3.54 | 45 | 105° C., 6.5 hr. | | CH₂Cl₂/MeOH = 39/1~9/1 | 5.34 (82.7) (III-54) | 203.0~ 207.5 |
| 71 | (II-22)* 2.23 g | (VI-1) 2.23 g | 3.01 | | 2.44 | 30 | 105° C., 8.5 hr. | | CH₂Cl₂/MeOH | 1.35 (30.5) | 95.0~ |

IR (CHCl₃): 3630, 3590, 3390, 2499, 1506, 1467, 1440, 1421, 1399
(CHCl₃): 3397, 3220, 1513, 1470, 1452, 1437, 1423, 1397
(CHCl₃): 3675, 3599, 3465, 3285, 2465, 1631, 1521, 1488, 1478, 1462, 1457(sh), 1439(sh), 1402
(Nujol): 3300, 3055, 3030, 2810, 2770, 2670, 1606, 1528, 1487, 1471, 1456, 1448
(CHCl₃): 3690, 3600, 1637(sh), 1632, 1587, 1552, 1510(sh), 1495, 1440

TABLE 7-continued

| *(II-22) [structure: 4-(3,4-dimethoxyphenyl)-4-hydroxypiperidine] | 2.60 g | 10/1~5/1 | (III-55) | 96.5 |

TABLE 8

(Step 2)

| (III) (g) | acid | solvent (ml) | reflux time | purification condition (2) | Product g (%) |
|---|---|---|---|---|---|
| (III-20) 2.53 g | TsOH.H$_2$O (2.68 g) | toluene (60) CH$_2$Cl$_2$ (20) | 13 hr. | ethyl acetate CH$_2$Cl$_2$/MeOH = 10/1 | I a-36 2.17 g (90.3) |
| (III-21) 2.66 g | TsOH.H$_2$O (2.93 g) | toluene (300) CH$_2$Cl$_2$ (50) | 30 hr. | CH$_2$Cl$_2$/MeOH = 20/1 | I a-37 2.27 g (90.0) |
| (III-22) 3.30 g | TsOH.H$_2$O (3.49 g) | toluene (300) | 48 hr. | ethyl acetate CH$_2$Cl$_2$/MeOH = 20/1 | I a-38 2.50 g (80.0) |
| (III-23) 3.18 g | TsOH.H$_2$O (4.21 g) | toluene (250) CH$_2$Cl$_2$ (60) | 69 hr. | toluene/ethyl acetate = 1/1 CH$_2$Cl$_2$/MeOH = 20/1 | I a-39 2.96 g (Quantitative) |
| (III-24) 2.56 g | CF$_3$COOH (27 ml) | — | 8 hr. | toluene/ethyl acetate = 30/1 | I a-40 2.40 g (98.0) |
| (III-25) 3.80 g | CF$_3$COOH (26 ml) | — | 8.5 hr. | CH$_2$Cl$_2$/MeOH = 30/1 | I a-41 3.50 g (96.8) |
| (III-26) 3.16 g | TsOH.H$_2$O (3.16 g) | toluene (250) CH$_2$Cl$_2$ (70) | 27 hr. | CH$_2$Cl$_2$/MeOH = 20/1 | I a-42 2.20 g (73.1) |
| (III-27) 2.45 g | TsOH.H$_2$O (2.55 g) | toluene (200) CH$_2$Cl$_2$ (50) | 48 hr. | toluene/ethyl acetate = 1/1 CH$_2$Cl$_2$/MeOH = 20/1 | I a-43 1.87 g (80.2) |
| (III-28) 2.10 g | TsOH.H$_2$O (1.60 g) | toluene (100) | 29 hr. | CH$_2$Cl$_2$/MeOH = 20/1 ethyl acetate | I a-44 1.480 g (73.8) |
| (III-29) 0.84 g | TsOH.H$_2$O (0.52 g) | toluene (60) | 31 hr. | CH$_2$Cl$_2$/MeOH = 15/1 | I a-45 0.80 g (Quantitative) |
| (III-30) 2.10 g | CF$_3$COOH (10 ml) | — | 39 hr. | CH$_2$Cl$_2$/MeOH = 30/1 | I a-46 1.34 g (70.2) |
| (III-31) 3.51 g | CF$_3$COOH (36 ml) | — | 8 hr. | CH$_2$Cl$_2$/MeOH = 20/1 | I a-47 2.80 g (92.9) |
| (III-32) 4.14 g | TsOH.H$_2$O (3.25 g) | toluene (250) | 26.5 hr. | CH$_2$Cl$_2$/MeOH = 20/1 | I a-48 3.16 g (80.3) |
| (III-33) 1.93 g | TsOH.H$_2$O (2.10 g) | toluene (160) CH$_2$Cl$_2$ (60) | 16 hr. | CH$_2$Cl$_2$/MeOH = 15/1 | I a-49 1.50 g (81.9) |
| (III-34) 3.10 g | CF$_3$COOH (35 ml) | — | 25 hr. | CH$_2$Cl$_2$/MeOH = 30/1-20/1 | I a-50 2.80 g (94.1) |
| (III-35) 2.70 g | CF$_3$COOH (35 ml) | — | 19.5 hr. | CH$_2$Cl$_2$/MeOH = 50/1-20/1 | I a-51 2.40 g (92.7) |
| (III-36) 4.09 g | TsOH.H$_2$O (4.03 g) | toluene (280) CH$_2$Cl$_2$ (70) | 26 hr. | toluene = ethyl acetate = 3/1 CH$_2$Cl$_2$/MeOH = 20/1 | I a-52 3.76 g (96.4) |
| (III-37) 3.00 g | CF$_3$COOH (30 ml) | — | 8 hr. | CH$_2$Cl$_2$/MeOH = 25/1 | I a-53 2.57 g (89.5) |
| (III-38) 2.86 g | TsOH.H$_2$O (2.76 g) | benzene (150) CH$_2$Cl$_2$ (50) | 23 hr. | CH$_2$Cl$_2$/MeOH = 10/1-20/1 | I a-54 1.48 g (48.7) |
| (III-39) 1.00 g | TsOH.H$_2$O (1.00 g) | benzene (150) toluene (100) | 25 hr. | toluene/ethyl acetate = 1/1 CH$_2$Cl$_2$/MeOH = 20/1 | I a-55 0.93 g (97.7) |
| (III-40) 1.134 g | CF$_3$COOH (10 ml) | | 1.0 hr. | CH$_2$Cl$_2$/MeOH/ NH$_4$OH = 64/8/1 | I a-56 1.416 g (79.3) |
| (III-41) 1.445 g | CF$_3$COOH (10 ml) | | 1.5 hr. | CH$_2$Cl$_2$/MeOH/ NH$_4$OH = 64/8/1 | I a-57* 1.787 g (75.1) |
| (III-42) 1.002 g | CF$_3$COOH (10 ml) | | 50 min. | CH$_2$Cl$_2$/MeOH/ NH$_4$OH = 64/8/1 | I a-58* 1.117 g (69.8) |
| (III-43) 0.722 g | CF$_3$COOH (6 ml) | | 1 hr. | CH$_2$Cl$_2$/MeOH/ NH$_4$OH = 128/12/1-64/8/1 | I a-59* 0.881 g (64.6) |
| (III-44) 12.82 g | CF$_3$COOH (38.3 ml) | | 3.17 hr. | CH$_2$Cl$_2$/MeOH/ NH$_4$OH = 128/16/1-32/6/1 | I a-60 7.719 g (64.9) |
| (III-45) 721 mg | CF$_3$COOH (10 ml) | | 1.5 hr. | CH$_2$Cl$_2$/MeOH/ NH$_4$OH = 128/16/1 | I a-61* 664 mg (73.1) |
| (III-46) | CF$_3$COOH | | 1 hr. | CH$_2$Cl$_2$/MeOH = | I a-62* |

TABLE 8-continued

| (III) (g) | acid | solvent (ml) | (Step 2) reflux time | purification condition (2) | Product g (%) |
|---|---|---|---|---|---|
| 766 mg | (10 ml) | | | 19/1~9/1 | 572 mg (60.5) |
| (III-47) 540 mg | CF$_3$COOH (8 ml) | | 48 hr. | CH$_2$Cl$_2$/MeOH = 30/1~10/1 | I a-63 529 mg (69.2) |
| (III-48) 2.105 g | CF$_3$COOH (5 ml) | | 1.25 hr. room temperature | CH$_2$Cl$_2$/MeOH = 19/1 | I a-64 1.693 g (85.3) |
| (III-49) 2.87 g | CF$_3$COOH (35 ml) | | 50 min. | CH$_2$Cl$_2$/MeOH = 49/1 | I a-65 2.61 g (86.7) |
| (III-50) 2.85 g | CF$_3$COOH (30 ml) | | 8 hr. | CH$_2$Cl$_2$/MeOH = 20/1-10/1 | I a-66 2.70 g (98.6) |
| (III-51) 3.85 g | CF$_3$COOH (50 ml) | | 3 days | CH$_2$Cl$_2$/MeOH = 15/1-10/1 | I a-67 3.53 g (96.0) |
| (III-52) 1.75 g | CF$_3$COOH (25 ml) | | 7 hr. | CH$_2$Cl$_2$/MeOH = 20/1 | I a-68 1.54 g (92.0) |
| (III-53) 2.98 g | CF$_3$COOH (34 ml) | | 50 min. | CH$_2$Cl$_2$/MeOH = 49/1 | I a-69 2.71 g (87.1) |
| (III-54) 2.62 g | CF$_3$COOH (33 ml) | | 50 min. | toluene/acetone = 9/1-3/1 | I a-70 2.41 g (87.5) |
| (III-55) 1.58 g | CF$_3$COOH (20 ml) | | 2.5 hr. | CH$_2$Cl$_2$/MeOH = 15/1-7/1 | I a-71 1.28 g (49.5) |

*: maleate

TABLE 9

| Compd. No. | m.p. (°C.) (solvent*) | Anal. Calcd. (%) Found (%) | IR (cm$^{-2}$) | NMR (δ) |
|---|---|---|---|---|
| Ia-36 | 130.5–132.0 (CH$_2$Cl$_2$—Et$_2$O) | C$_{19}$H$_{25}$N$_3$O$_2$: C, 69.42 (69.70) H, 7.65 (7.70) N, 12.76 (12.83 | (CHCl$_3$) 3310, 1713, 1680 1545,1489, 1460 | (CDCl$_3$) 2.020(quint, J=8Hz, 2H); 2.329(s, 3H, J=7Hz, 2H); 2.56–2.59(m, 4H); 2.671(t, J=7Hz, 2H); 2.766(t, J=6Hz, 2H); 3.217(q, J=3Hz, 2H); 3.510(q, J=7Hz, 2H); 3.859(t, J=7Hz, 2H); 6.016(quint, J=3 Hz, 1H); 7.116(d, J=8Hz, 2H); 7.284(d, J=8Hz, 2H); 8.596(br, 1H) |
| Ia-38 | 161.5–163.0 (iPrOH) (oxalate) | C$_{22}$H$_{29}$N$_3$O$_6$: C, 60.86 (61.24) H, 6.79 (6.77) N, 9.51 (9.74) | (Nujol) 3330, 2600, 2500 1717, 1645, 1605 1533, 1485, 1460 | (CDCl$_3$) 1.782 (quint, J-7Hz, 2H); 1.969(quint, J=8Hz, 2H); 2.301(s, 3H); 2.44–2.59(m, 6H); 2.658(t, J=6Hz, 2H); 3.111(q, J=3Hz, 2H); 3.3 47(q, J=7Hz, 2H); 3.813(t, J=7Hz, 2H); 5.999(quint, J=3Hz, 1H); 6.00–7.02(m, 1H); 7.14–7.16(m, 3H); 8.456(brs, 1H) |
| Ia-39 | 146.0–147.0 (iPrOH) (oxalate) | C$_{22}$H$_{29}$N$_3$O$_6$: C, 61.08 (61.24) H, 6.70 (6.77) N, 9.71 (9.74) | (Nujol) 3300, 2600(br). 1708, 1683, 1548 1490(sh), 1460 | (CDCl$_3$) 1.873(quint, J=7Hz, 2H); 2.030(quint, J=8Hz, 2H); 2.297(s, 3H); 2.38–2.48(m, 1H); 2.593(t, J=7Hz, 2H); 2.606(t, J=8Hz, 2H); 2.7 46(t, J=6Hz, 2H); 3.184(q, J=3Hz, 2H); 3.402(quint, J=7Hz, 2H); 5.531(quint, J=2Hz, 1H); 7.11–7.17(m, 4H); 8.519(brs, 1H) |
| Ia-40 | 146.5–147.5 (iPrOH) (maleate) | C$_{25}$H$_{33}$N$_3$O$_6$ C 63.40 (63.68) H, 6.99 (7.05) N, 3.87 (8.91) | (Nujol) 3330, 2420–2300, 1700, 1620, 1575 1530, 1460, 1450 (sh) | (CDCl$_3$) 1.825(quint, J=8Hz, 2H); 2.020(quint, J=7Hz, 2H); 2.240(s, 3H); 2.254(s, 3H); 2.48–2.56(m, 4H); 2.594(t, J=8Hz, 2H); 2.697(t, J=5Hz, 2H); 3.147(q, J=3Hz, 2H); 3.390(q, J=7Hz, 2H); 3.859(t, J=7Hz, 2H); 6.002(quint, J=2Hz, 1H); 7.04–7.15(m, 3H); 8.489 (brs, 1H) |
| Ia-41 | 159.0–160.0 (iPrOH) (maleate) | C$_{25}$H$_{33}$N$_3$O$_6$ C, 63.71 (63.38) H, 7.05 (7.05) N, 8.86 (8.91) | (Nujol) 3290, 2400–2300, 1720(sh), 1710 1685, 1620, 1600 (sh), 1577, 1550 | (CDCl$_3$) 1.821(quint, J=7Hz, 2H); 2.013(quint, J=8Hz, 2H); 2.300(s, 6H); 2.48–2.55(m, 4H); 2.592(t, J=7Hz, 2H); 2.690(t, J=6Hz, 2H); 3.1 42(q, J=3Hz, 2H); 3.385(q, J=7Hz, 2H); 3.855(d-d, J$_1$=8Hz, J$_2$= 7Hz, 2H); 6.014(quint, J=2Hz, 1H); 6.878(s, 1H); 6.998(s, 2H) |
| Ia-42 | 155.5–157.0 (iPrOH) (maleate) | C$_{23}$H$_{29}$N$_3$O$_6$Cl C, 57.74 (57.80) H, 5.84 (5.90) N, 8.78 (8.79) Cl, 7.14 (7.42) | (Nujol) 3310, 2350, 2260 1715,1682,1585 1520, 1485(sh). 1455 | (CDCl$_3$) 1.825 (quint, J=7Hz, 2H); 2.022(quint, J=8Hz, 2H); 2.49–2.56(m, 4H); 2.538(t, J=7Hz, 2H); 2.709(t, J=6Hz);3.259(q, J=3Hz, 2H); 3.389(q, J=7Hz, 2H); 3.861(t, J=7Hz, 2H); 6.084(quint, J=2Hz, 1H); 7.18–7.30(m, 3H); 7.346(s, 1H); 8.499(brs, 1H) |
| Ia-43 | 102.0–103.5 (ethyl acetate/ Et$_2$O) | C$_{18}$H$_{22}$N$_3$O$_2$Cl C, 61.99 (62.15) H, 6.31 (6.37) N, 1207 (12.08) Cl, 9.96 (10.19) | (CHCl$_3$) 3310, 1715, 1680 1595, 1545, 1489 1460 | (CDCl$_3$) 2.024(quint, J=7Hz, 2H); 2.55–2.64(m, 4H); 2.673(t, J=7Hz, 2H); 2.766(t, J=6Hz, 2H); 3.218(q, J=3Hz, 2H); 3.504(q, J=6Hz, 2H); 3.860(t, J=7Hz, 2H); 6.082(quint, J=2Hz, 1H); 7.19–7.27(m, 3H); 7.361(s, 1H); 8.615(brs. 1H) |
| Ia-44 | 140.5–142.0 (iPrOH) (maleate) | C$_{23}$H$_{29}$N$_3$O$_6$Cl.1/5H$_2$O C, 57.35 (57.37) H, 5.87 (5.94) N, 8.67 (8.37) Cl, 7.72 (7.36) | (Nujol) 3280, 2580, 2360 1715, 1690, 1620 (sh), 1460 | (CDCl$_3$) 1.846(quint, J=7Hz, 2H); 2.048(quint, J=8Hz, 2H); 2.47–2.51(m, 2H); 2.566(t, J=8Hz, 2H); 2.606(t, J=8Hz, 2H); 2.728(t, J=6Hz, 2H); 5.656(quint, J=2Hz); 7.15–7.37(m, 4H); 8.510(brs, 1H) |
| Ia-45 | 142.0–143.5 (maleate) | C$_{23}$H$_{36}$N$_3$O$_6$Cl C, 56.54 (56.96) H, 5.89 (5.65) N, 8.79 (9.06) Cl, 7.98 (7.64) | (Nujol) 3300, 2580–2400, 1710, 1682, 1617 1565, 1528 | (CDCl$_3$) 2.007(t, quint, J=7Hz, 2H); 2.35–2.57(m, 2H); 2.610(t, J=8Hz); 2.746(g, J=7Hz, 2H); 2.830(t, J=6Hz, 2H); 3.723(q, J=3Hz, 2H); 3.544(q, J=6Hz, 2H); 3.869(t, J=7Hz, 2H); 5.656(q, J=2Hz, 1H); 7.15–7.37(m, 4H); 8.626(brs, 1H) |
| Ia-46 | 216.0–217.5 (MeOH) (oxalate) | C$_{21}$H$_{25}$N$_3$O$_6$Cl$_2$.1/5H$_2$O C, 51.31 (51.48) H, 5.15 (5.23) N, 8.53 (8.58) Cl, 14.65 (14.47) | (Nujol) 3340, 1710, 1645 1588, 1562, 1538 1488, 1460, 1420 | (CDCl$_3$) 1.807(quint, J=7Hz, 2H); 2.027(quint, J=8Hz, 2H); 2.48–2.56(m, 4H); 2.599(t, J=7Hz, 2H); 2.689(t, J=6Hz, 2H); 3.155(q, J=3Hz, 2H); 3.383(q, J=7Hz, 2H); 3.859(t, J=7Hz, 2H); 6.111(quint, J=2 Hz, 1H); 7.20–7.25(m, 3H); 8.510(brs, 1H) |

TABLE 9-continued

| Compd. No. | m.p. (°C.) (solvent*) | Anal. Calcd. (%) Found (%) | IR (cm$^{-2}$) | NMR (δ) |
|---|---|---|---|---|
| Ia-47 | 99.0-100.0 (CH$_2$Cl$_2$—Et$_2$O) | C$_{19}$H$_{22}$N$_3$O$_2$Br: C, 56.32 (56.16) H, 6.04 (5.95) N, 10.35 (10.34) Br, 19.59 (19.67) | (CHCl$_3$) 33.20, 1712, 1680 1545, 1489, 1465 (sh), 1460, 1440 | (CDCl$_3$) 1.819(quint, J=7Hz, 2H); 2.023(quint, J=7Hz, 2H); 2.49-2.56(m, 4H); 2.598(t, J=7Hz, 2H); 2.699(t, J=6Hz, 2H); 3.145(q, J=3Hz, 2H); 3.386(q, J=6Hz, 2H); 3.861(t, J=7Hz, 2H); 6.064(quint, J=2 Hz, 1H); 7.247(d, J=8Hz, 2H); 7.462(d, J=8Hz, 2H); 8.495(brs, 1H) |
| Ia-48 | 97.5-98.5 (CH$_2$Cl$_2$—Et$_2$O) | C$_{19}$H$_{24}$N$_3$O$_2$F: C, 60.47 (7.00) N, 12.07 (12.16) F, 5.57 (5.50) | (CHCl$_3$) 3320, 1713, 1682 1605, 1545, 1510 1490, 1460 | (CDCl$_3$) 1.825(quint, J=7Hz, 2H); 2.021(quint, J=8Hz, 2H); 2.49-2.56(m, 4H); 2.597(t, J=8Hz, 2H); 2.705(t, J=6Hz); 3.152(q, J=3Hz, 2H); 3.389(q, J=7Hz, 2H); 3.862(t, J=7Hz, 2H); 5.998(quint, J=2Hz, 1H); 6.992(t, J=8Hz, 2H); 7.343(d-d, J$_1$=8Hz, J$_1$=5Hz, 2H); 8.495(brs, 1H) |
| Ia-49 | 136.0-136.5 (iPrOH) (maleate) | C$_{22}$H$_{26}$N$_3$O$_6$F: C, 59.13 (59.05) N, 9.31 (9.39) F, 4.48 (4.25) | (Nujol) 3300, 2600(br) 1720, 1675, 1610 1515 | (CDCl$_3$) 2.028(quint, J=8Hz, 2H); 2.50-2.60(m, 4H); 2.674(t, J=7Hz, 2H); 2.741(t, J=5Hz, 2H); 3.216(q, J=3Hz, 2H); 3.551(q, J=6Hz, 2H); 3.866(t, L=7Hz, 2H); 5.993(quint, J=2Hz, 1H); 6.997(t, J=9Hz, 2H); 7.350(d-d, J$_1$=9Hz, J$_2$=5Hz, 2H); 8.615(brs, 1H) |
| Ia-50 | 185.0-188.0 (iPrOH—MEOH—Et$_2$O) (hydrochloride) | C$_{20}$H$_{23}$N$_3$O$_2$ClF$_3$.HCl.1/5H$_2$O C, 50.92 (51.11) H, 515 (5.23) N, 8.71 (8.94) Cl, 14.95 (15.08) F, 11.83 (12.12) | (Nujol) 3320, 2670, 2550 2420, 1710 | (CDCl$_3$) 1.822(quint, J=7Hz, 2H); 2.030(quint, J=8Hz, 2H); 2.544(t, J=8Hz, 2H); 2.55-2.60(m, 2H); 2.602(t, J=8Hz, 2H); 2.718(q, J=5Hz, 2H); 3.177(q, J=2Hz, 2H); 3.393(q, J=7Hz, 2H); 3.865(t, J=7Hz, 2H); 6.10-6.18(m, 1H); 7.40-7.50(m, 2H); 7.679(brs, 1H); 8.511 (brs, 1H) |
| Ia-51 | 213.0-215.0 (iPrOH—MeOH) (hydrochloride) | C$_{19}$H$_{21}$N$_3$O$_2$ClF$_3$.HCl C, 50.38 (50.45) H, 4.90 (4.90) N, 9.22 (9.29) Cl, 15.65 (15.68) | (Nujol) 3500, 2520, 1704 1683, 1548, 1493 1462 | (CDCl$_3$) 2.030(quint, J=7Hz, 2H); 2.50-2.60(m, 2H); 2.597(t, J=8hz, 2H); 2.678(t, J=6Hz, 2H); 2.777(t, J=6Hz, 2H); 3.236(q, J=3Hz, 2H); 3.504(q, J=6Hz, 2H); 3.864(t, J=7Hz, 2H); 6.10-6.16l(m, 1H); 7.40-7.50(m, 2H); 7.685(brs, 1H) |
| Ia-52 | 83.0-84.0 (CH$_2$Cl$_2$—Et$_2$O) | C$_{17}$H$_{22}$N$_3$O$_2$SCl C, 55.38 (55.50) H, 596 (6.03) N, 11.51 (11.42) S, 8.69 (8.71) Cl, 9.69 (9.64) | (CHCl$_3$) 3320, 1712, 1680 1545 | (CDCl$_3$) 1.801(quint, J=7Hz, 2H); 2.024(quint, J=7Hz, 2H); 2.50(brs, 2H) 2.520(t, J=7Hz, 2H); 2.596(t, J=8Hz, 2H); 2.670(t, J=6Hz, 2H); 3.119(q, J=3Hz, 2H); 3.376(q, J=7Hz, 2H); 3.857(t, J=7Hz, 2H); 5.953(quint, J=2Hz, 1H); 6.688(d, J=4Hz, 1H); 6.756(d, J=4Hz, 2H); 8.485(brs, 1H) |
| Ia-53 | 156.5-157.5 (iPrOH) (maleate) | C$_{21}$H$_{25}$N$_3$O$_6$SCl$_2$: C, 48.58 (48.65) H, 4.89 (4.86) N, 8.02 (8.11) S, 5.92 (6.18) | (Nujol) 3300, 1708, 1680 1585, 1535 | (CDCl$_3$) 1.808(quint, J=7Hz, 2H); 2.030(quint, J=7Hz, 2H); 2.48-2.56(m, 4H); 2.604(t, J=8Hz, 2H); 2.659(t, J=6Hz, 2H); 3.136(q, J=3Hz, 2H); 3.383(q, J=7Hz, 2H); 3.862(t, J=7Hz, 2H); 5.995(quint, J=2 Hz, 1H); 6.712(s, 1H); 8.497(brs, 1H) |
| Ia-54 | 144.0-145.0 (iPrOH) (maleate) | C$_{24}$H$_{30}$N$_3$O$_6$Cl C, 58.44 (58.59) H, 6.05 (6.15) N, 8.52 (8.54) Cl, 7.33 (7.21) | (Nujol) 3280, 2400-2280, 1692, 1650, 1622 1575, 1522, 1495 | (CDCl$_3$) 1.78-1.91(m, 6H); 2.45-2.60(m, 6H); 2.703(t, J=6Hz, 2H); 3.161 (q, J=3Hz, 2H); 3.383(q, J=7Hz, 2H); 3.76-3.83(m, 2H); 6.056 (quint, J=2Hz, 1H); 7.264, 7.322(ABq, J=9Hz, 4H); 9.449(brs, 1H) |
| Ia-55 | 134.0-135.5 (CH$_2$Cl$_2$—Et$_2$O) | C$_{19}$H$_{24}$N$_3$O$_2$Cl C, 62.84 (63.06) H, 6.67 (6.68) N, 11.41 (11.61) Cl, 10.05 (9.80) | (CHCl$_2$) 3280, 1795, 1645 1527, 1495, 1480 1463, 1450 | (CDCl$_3$) 1.78-1.85(m, 4H); 2.45-2.60(m, 4H); 2.680(t, J=7Hz, 2H); 2.770 (t, J=6Hz, 2H); 3.238(q, J=2Hz,2H); 3.513(q, J=7Hz, 2H); 3.80-3.83(m, 2H); 6.051(quint, J=2Hz, 1H); 7.24-7.35(m, 4H); 9.521 (brs, 1H) |
| Ia-56 | 192.5-193.5 (CH$_2$Cl$_2$—MeOH-iPrOH) | C$_{24}$H$_{30}$N$_2$.2C$_4$H$_4$O$_4$ C, 65.32 (65.51) H, 7.84 (7.90) | (Nujol) 2340, 1916, 1707 1619, 1563, 1542 | (CDCl$_3$) (free) 0.966(d, J=5Hz, 3H); 1.314(s, 9H); 1.43-1.57(m, 3H); 1.67-1.78 (m, 2H); 1.930(quint, J=7Hz, 2H); 2.239(t, J=12Hz, 2H); 2.49-2.58 |

TABLE 9-continued

| Compd. No. | m.p. (°C.) (solvent*) | Anal. Calcd. (%) Found (%) | IR (cm$^{-2}$) | NMR (δ) |
|---|---|---|---|---|
| | (di-maleate) | N, 4.77 (4.77) | 1481, 1460, 1446 1378 | (m, 2H); 2.528(t, J=7Hz, 2H); 2.63-2.74(m, 4H); 3.14-3.21 (m, 4H); 6.027(quint, J=1Hz, 1H); 7.330(ABq, J=8Hz, 4H) |
| Ia-57 | 191.5-193.0 (CH$_2$Cl$_2$—MeOH-iPrOH) di-maleate) | C$_{21}$H$_{32}$N$_2$.2C$_4$H$_4$O$_4$ C, 63.75 (63.95) H, 7.31 (7.40) N, 5.16 (5.14) | (Nujol) 2340, 1995, 1709 1621, 1525(sh), 1510(sh), 1483 1462, 1449(sh), 1379 | (CDCl$_3$) 0.980(d, J=5Hz, 3H); 1.48-1.66(m, 3H); 1.70-1.82(m, 2H); 1.953 (quint, J=7Hz, 2H); 2.333(s, 3H); 2.357(t, J=12Hz, 2H); 2.544 (t, J=7Hz, 4H); 2.715(t, J=8Hz, 2H); 2.78-2.84(m, 2H); 3.160 (q, J=3Hz, 1H); 3.298(d, J=12Hz); 6.013(quint, J=1Hz, 1H); 7.123.7.2 84 (ABq, J=8Hz, 4H) |
| Ia-58 | 190.0-192.0 (MeOH-iPrOH) (di-maleate) | C$_{23}$H$_{36}$N$_2$.2C$_4$H$_4$O$_4$ C, 64.92 (65.02) H, 7.68 (7.74) N, 4.91 (4.89) | (Nujol) 2360, 1997, 1708 1619, 1570, 1535 1480, 1457, 1448 (sh), 1379 | (CDCl$_3$) 1.324(s, 9H); 1.50-2.00(m, 8H); 2.50-2.80(m, 12H); 3.200(q, J= 3Hz, 2H); 6.056(s, 1H); 7.347(ABq, J=8Hz, 4H) |
| Ia-59 | 193.0-195.0 (CHCl$_3$—MeOH) (tri-maleate) | C$_{23}$H$_{37}$N$_3$.3C$_4$H$_4$O$_4$ C, 59.39 (59.58) H, 6.95 (7.03) N. 602 (5.96) | (Nujol) 2335, 1995, 1706 1621, 1568, 1542 (sh), 1478, 1460 1439, 1380(sh) | (CDCl$_3$) 1.313(s, 9H); 1.786(quint, J=7Hz, 2H); 2.296(s, 3H); 2.37-2.60 (m, 17H); 2.703(t, J=5Hz, 2H); 3.158(q, J=3Hz, 2H); 6.028 quint, J=1Hz, 1H); 7.382(ABq. J=8Hz, 4H) |
| Ia-60 | 75.0-77.0 (Et$_2$O-n-hexane) | C$_{16}$H$_{21}$NO C, 77.94 (77.88) H, 9.16 (9.15) N, 6.22 (6.05) | (Nujol) 3110, 3023, 2773 1518, 1467, 1412 1397, 1379 | (CDCl$_3$) 1.791(quint, J=7Hz, 2H); 2.332(s, 3H); 2.50-2.60(m, 2H); 2.735 (t, J=6Hz, 2H); 2.775(t, J=6Hz, 2H); 3.221(q, J=3Hz, 2H); 3.834 (t, J=5Hz, 2H); 6.001(quint, J=2Hz, 1H); 7.123.7.272(ABq, J=8Hz, 4H) |
| Ia-61 | 115.0-116.0 (iPrOH—Et$_2$O) (maleate) | C$_{20}$H$_{39}$N$_3$O.C$_4$H$_4$O$_4$ C, 64.88 (64.99) H, 7.54 (7.50) N, 9.42 (9.47) | (Nujol) 3405, 2720, 2570 2295, 1642, 1580 1538, 1499, 1457 | (CD$_3$OD) 1.87-12.05(m, 6H); 2.333(s, 3H); 2.886(brs, 2H); 3.21-3.36(m, 1H); 3.522(brs, 2H); 3.913(s, 2H); 6.099(s, 1H); 6.245(s, 2H); 7.188.7.369(ABq, J=9Hz, 4H) |
| Ia-62 | 164.0-166.0 (MeOH—Et$_2$O) (maleate) | C$_{25}$H$_{31}$N$_3$O.C$_4$H$_4$O$_4$ C, 68.89 (68.89) H, 6.97 (6.98) N, 8.30 (8.31) | (Nujol) 3403, 3037, 2330 1700, 1640, 1578 1537, 1498, 1457 (sh), 1449, 1409 | (CD$_3$OD) 1.88-2.06(m, 4H); 2.951(brs, 2H); 3.20-3.40(m, 6H); 3.557(brs, 1H); 3.959(brs, 2H); 6.220(s, 1H); 6.248(s, 2H); 7.30-7.70(m, 9H) |
| Ia-63 | 150.0-151.5 (CH$_2$Cl$_2$—Et$_2$O) | C$_{24}$H$_{28}$N$_5$OF$_3$ C, 62.55 (62.73) H, 6.08 (6.14) N, 1513 (15.24) F, 12.36 (12.40) | (CHCl$_3$) 1632, 1617(sh), 1588, 1552, 1495 1437 | (CDCl$_3$) 1.940(quint, J=7Hz, 2H); 2.450(t, J=8Hz, 2H); 2.547(t, J=7Hz, 2H); 5.565(brs, 2H); 2.727(t, J=6Hz, 2H); 6.142(s, 1H); 6.515 (t, J=5Hz, 1H); 7.448.7.540(ABq, J=8Hz, 4H); 8.301(d, J=5Hz, 2H) |
| Ia-64 | 108.0-109.0 (CH$_2$Cl$_2$—Et$_2$O-n-hexane) | C$_{19}$H$_{26}$N$_2$O C 76.26 (76.47) H, 8.70 (8.78) N, 9.32 (9.39) | (CHCl$_3$) 1625, 1512, 1466 1448, 1378 | (CDCl$_3$) 1.78-2.04(m, 4H); 2.332(s, 3H); 2.574(t, J=8Hz, 4H); 2.765(t, J=6Hz, 2H); 2.881(t, J=8Hz, 2H); 3.211(q, J=3Hz, 2H); 3.448(t, J=6Hz, 2H); 3.477(t, J=6Hz, 2H); 6.02(quint, J=2Hz, 1H); 7.122.7 .285 (ABq, J=8Hz, 4H) |
| Ia-65 | 183.0-190.0 (MeOH—Et$_2$O) (hydro-chloride) | C$_{22}$H$_{31}$N$_3$O$_2$.HCl C, 65.06 (65.09) H, 8.04 (7.95) N, 10.38 (10.35) Cl, 8.46 (8.73) | (Nujol) 3310, 2725, 2670 2405, 1709, 1688 1549, 1519, 1488 1459, 1430, 1412 1392 | (CDCl$_3$) 1.313(s, 9H); 2.018(quint, J=6Hz, 2H); 2.52-2.64(m, 6H); 2.678 (6, J=7Hz, 2H); 2.774(t, J=6Hz, 2H); 3.212.3.242(ABq, J=3Hz, 2H) 3.545.3.484(ABz, J=7Hz, 2H); 3.859(t, J=7Hz, 2H); 6.029(quint, J=2Hz, 1H); 7.332(s, 4H); 8.604(brs, 1H) |
| Ia-66 | 216.0-219.0 (MeOH—Et$_2$O) (hydro-chloride) | C$_{18}$H$_{21}$N$_3$O$_2$Cl$_2$.HCl C, 51.66 (51.63) H, 5.34 (5.30) | (Nujol) 3290, 2510, 1712 1672, 1521 | (CDCl$_3$) 2.024(quint, J=7Hz, 2H); 2.45-2.55(m, 2H); 2.594(t, J=8Hz, 2H); 2.665(t, J=8Hz, 2H); 2.754(t, J=6Hz, 2H); 3.214(q, J=3Hz, 2H); |

TABLE 9-continued

| Compd. No. | m.p. (°C.) (solvent[a]) | Anal. Calcd. (%) Found (%) | IR (cm$^{-1}$) | NMR (δ) |
|---|---|---|---|---|
| Ia-67 | 238.0–248.0 (MeOH—Et$_2$O) (hydrochloride) | N, 10.01 (10.03) Cl, 25.12 (25.40) C$_{19}$H$_{22}$N$_3$O$_2$F$_3$·HCl C, 54.43 (54.61) H, 5.59 (5.55) N, 9.89 (10.06) Cl, 8.45 (8.48) | (Nujol) 3310, 2930, 2860 2460, 1711, 1687 1617, 1541 | 3.497(q, J=6Hz, 2H); 3.860(t, J=7Hz, 2H); 6.0–6.14(m, 1H); 7.208 (dd, J$_1$=8Hz, J$_2$=2Hz, 1H); 7.365(d, J=8Hz, 1H); 7.450(d, J=2Hz, 1H); 8.615(brs, 1H) (CDCl$_3$) 2.032(quint, J=8Hz, 2H); 2.50–2.66(m, 4H); 2.69(t, J=6Hz, 2H); 2.722(t, J=6Hz, 2H); 3.256(q, J=3Hz, 2H); 3.518(q, J=6Hz, 2H); 3.868(t, J=7Hz, 2H); 6.14–6.17(m, 1H); 7.478, 7.567(ABq, J=9Hz, 4H); 8.625(brs, 1H) (CD$_3$OD) |
| Ia-68 | 228.0–232.0 (MeOH—Et$_2$O) (hydrochloride) | C$_{18}$H$_{22}$N$_3$O$_2$Br·HCl C, 50.89 (50.52) H, 5.58 (5.41) N, 9.90 (9.80) Cl, 8.22 (8.27) | (Nujol) 3320, 2920, 2860 2460, 1710, 1685 1537 | 2.029(quint, J=8Hz, 2H); 2.50–2.60(m, 2H); 2.598(t, J=8Hz, 2H); 2.675(6, J=7Hz, 2H); 2.769(t, J=6Hz, 2H); 3.216(q, J=3Hz, 2H); 3.509(q, J=6Hz, 2H); 3.865(t, J=7Hz, 2H); 6.04–6.08(m, 1H); 7.429, 7.247(ABq, J=9Hz, 4H); 8.611(brs, 1H) (CDCl$_3$) |
| Ia-69 | 205.0–210.0 (MeOH—Et$_2$O) (hydrochloride) | C$_{22}$H$_{27}$N$_3$O$_2$·HCl C, 67.72 (67.67) H, 6.64 (6.63) N, 9.80 (9.87) Cl, 8.10 (8.32) | (Nujol) 3305, 3045, 2415 2405, 1702, 1679 1578, 1540, 1488 1457, 1444, 1420 | 2.205(quint, J=8Hz, 2H); 2.54–2.66(m, 4H); 2.695(t, J=7Hz, 2H); 2.803(t, J=6Hz, 2H); 3.261(q, J=3Hz, 2H); 3.558, 3.497(ABq, J=7 Hz, 2H); 3.865(t, J=7Hz, 2H); 6.128(quint, J=2Hz, 1H); 7.28–7.67 (m, 9H); 8.624(brs, 1H) |

[a] a solvent for recrystallization

EXAMPLE 72

1-{3-(1-Methyl-2-oxo-imidazolidin-1-yl)propyl}-4-(4-tolyl)-1,2,5,6-tetrahydropyridine (I a-72)

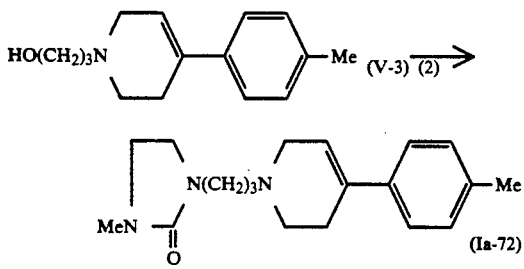

(1) A mixture of 870 mg of the compound (I a-60) and 8.0 ml of thionylchloride is stirred at room temperature for 2 hours. After removal of the excess reagent under reduced pressure, the residue was washed with Et$_2$O and dried under reduced pressure to prepare 1.067 g (Yield: 99.2%) of the compound (V-3) as pale yellow powder.

IR(CHCl$_3$) cm$^{-1}$: 1600, 1510, 1460, 1410

NMR (CDCl$_3$): 2.046 (quint, J=7 Hz, 2H); 2.334 (s, 3H); 2.54–2.64 (m, 2H); 2.629 (t, J=7H, 2H); 2.723 (t, J=5 Hz, 2H); 3.173 (q, J=2 Hz, 2H); 3.630 (t, J=7 Hz, 2H); 6.023 (quint, J=2 Hz, 1H); 7.123, 7.287 (ABq, J=8 Hz, 4H)

(2) To a solution of 266 mg of 1-methyl-2-oxo-imidazolidine in 5 ml of DMF was added 115 mg of 60% NaH under ice-cooling. After stirring at room temperature for 20 minutes, a solution of 553 mg of the compound (V-3) in 4 ml of DMF was added to the reaction mixture and stirred at room temperature for 90.5 hours. The reaction mixture was concentrated under reduced pressure and poured into d-HCl. The aqueous layer is made alkaline with NaHCO$_3$, extracted with CHCl$_3$—MeOH (19/1), dried over MgSO$_4$, and evaporated. The residue is subjected to column chromatography with silica gel, eluting with CHCl$_3$—MeOH (19/1) to prepare 491 mg of the compound (I a-72). The maleate is recrystallized from iPrOH-Et$_2$O to prepare 439 mg (Yield: 45.8%) of colorless needles. mp. 126.5°–128.0° C.

Anal Calcd. (%) for C$_{19}$H$_{27}$N$_3$O.C$_4$H$_4$O$_4$.1/5H$_2$O: C, 63.73; H, 7.20; N, 9.61. Found: C, 63.78; H, 7.31; N, 9.70.

IR (CHCl$_3$): 2450, 2340, 1910, 1689, 1622, 1502, 1451, 1409, 1382

NMR (CDCl$_3$): 1.797 (quint, J=8 Hz, 2H); 2.329 (s, 3H); 2.46–2.62 (m, 4H); 2.712 (t, J=5 Hz, 2H); 2.790 (s, 3H); 3.166 (q, J=3 Hz, 2H); 3.255 (t, J=7 Hz, 2H); 3.295 (s, 4H); 6.014 (quint, J=2 Hz, 1H ); 7.117, 7.283 (ABq, J=8 Hz, 4H)

EXAMPLE 73-91

The compounds (V) obtained in Example 19-21 are reacted in the same manner as Example 72 to prepare the compound (Ia). The reaction conditions are shown in Table 10.

TABLE 10

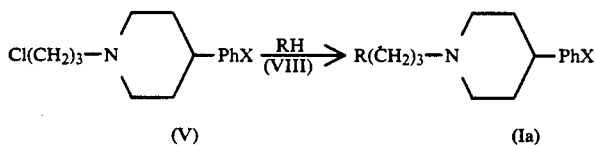

| Ex. No. | (V) | (VIII) | solvent | reaction condition | purification condition | product mg (Yield) | m.p. (°C.) | IR |
|---|---|---|---|---|---|---|---|---|
| 73 | (V-3) 742 mg | NNa / O 532 mg | DMF 5 ml | 100° C. 47 min. | CH$_2$Cl$_2$/MeOH = 19/1 | Ia-73*$^1$ 602 mg (46.2%) | 119.0–121.0 (iPrOH) | (CHCl$_3$) 2455, 2310, 1677 1622, 1512, 1497 1464, 1380, 1351 |
| 74 | (V-2) 1.02 g | HN / O 492 mg | DMF 10 ml | 100° C. 25 hr. | toluene/ acetone = 3/1–1/1 | Ia-74*$^1$ 266 mg (15.3%) | 152.0–154.0 (MeOH-Et$_2$O) | (Nujol) 2700–1750(br), 1695, 1663, 1619 1532, 1463, 1412 1378, 1358 |
| 75 | (V-3) 500 mg | CH$_3$N / O NH / O 215 mg | DMF 8 ml | 70° C. 10 hr. | CH$_2$Cl$_2$/MeOH = 39/1 | Ia-75 409 mg (62.4%) | 98.0–100.0 (CDCl$_3$-MeOH) | (CHCl$_3$) 3690, 1771, 1602 1511, 1488, 1454 1429, 1416, 1384 |

TABLE 10-continued $$Cl(CH_2)_3-N\underset{}{\overset{}{\bigcirc}}-PhX \xrightarrow[(VIII)]{RH} R(CH_2)_3-N\underset{}{\overset{}{\bigcirc}}-PhX$$

$$(V) \qquad\qquad\qquad (Ia)$$

| Ex. No. | (V) | (VIII) | solvent | reaction condition | purification condition | product mg (Yield) | m.p. (°C.) | IR |
|---|---|---|---|---|---|---|---|---|
| 76 | (V-3) 500 mg | H₂NPh 0.192 ml (K₂CO₃ 576 mg, NaI 468 mg, Pyridine 178 ml) | DMF 8 ml | 80° C. 15 hr. | toluene/ acetone = 4/1 | Ia-76*¹ 130 mg (72.1%) | 154.0– 155.5 (MeOH- Et₂O) | (Nujol) 3050, 2660, 2615 2570, 2480, 2410 1606, 1590, 1578 1517, 1498, 1479, 1447, 1423, 1398 1376 |
| 77 | (V-3) 650 mg | [Ph₂C-CH₂-C(=O)-NH cyclic] 788 mg (Pyridine 231 mg, NaI 608 mg) | DMF 6 ml | 100° C. 5 hr. | toluene/ acetone = 9/1 | Ia-77*¹ 1.08 g (71.4%) | 174.0– 176.0 (dec.) (MeOH- Et₂O) | (CHCl₃) 3685, 2495, 3350 2700–1800 (br), 1778, 1707, 1621 1511, 1496, 1446 1395 |
| 78 | (V-2) 440 mg | CH₃NHPh 0.20 ml (Pyridine 0.157 ml, NaI 412 mg) | DMF 8 ml | 110° C. 6 hr. 20 min. | toluene/ acetone = 9/1 | Ia-78*¹ 135 mg (17.6%) | 149.0– 151.0 MeOH- Et₂O) | (CHCl₃) 3575, 3338 |
| 79 | (V-3) 0.828 g | NaOPh 207 mg | DMF 8 ml | 70° C. 3 hr. 10 min. | toluene/ acetone = 9/1 | Ia-79*¹ 562 mg (66.3%) | 148.0– 150.0 (MeOH- Et₂O- iPrOH) | (Nujol) 2720, 2370, 1701 1620, 1598, 1584 1499, 1467, 1458(sh), 1387 |
| 80 | (V-3) 942 mg | 1,2,3,4-tetrahydroquinoline 2.34 ml | — | 150° C. 8 hr. 15 min. | toluene/ acetone = 19/1–9/1 | Ia-80 930 mg (54.4%) | 148.0– 150.0 (iPrOH- Et₂O) | (Nujol) 2720, 2575(sh), 2490(sh), 2330, 1708, 1652, 1600 1571, 1502, 1459 |
| 81 | (V-3) 624 mg | 1,2,3,4-tetrahydroisoquinoline 1.56 ml | — | 150° C. 4 hr. 10 min. | CH₂Cl₂MeOH = 19/1 | Ia-81 963 mg (66.6%) | 191.0– 192.0 (dec.) (MeOH- Et₂O) | (Nujol) 3030, 2720, 2278 1711, 1623, 15722 1532, 1513(sh), 1485, 1463, 1435 |
| 82 | (V-3) 517 mg | HN(iBu)₂ 1.358 g | — | 20 hr. reflux | CH₂Cl₂MeOH = 49/1 | Ia-82*¹ 457 mg (38.4%) | 140.5– 142.5 (CH₂Cl₂- Et₂O) | (Nujol) 2710, 2500, 1706 1572, 1480, 1455 1375 |
| 83 | (V-3) 511 mg | H₂N(iBu), 1.02 ml | — | 10.5 hr. reflux | CH₂Cl₂MeOH/ NH₄OH = 128/12/1 | Ia-83*¹ 471 mg (44.4%) | 179.5– 182.5 (CH₂Cl₂- Et₂O) | (Nujol) 3340, 2780, 2545 2460, 1699, 1618 1577, 1474, 1458 1441, 1381 |
| 84 | (V-3) 466 mg | [pyrrolidine NH] 0.78 ml | — | 50° C. 3 hr. | CH₂Cl₂MeOH/ NH₄OH = 128/16/1– 32/4/0.5 | Ia-84*¹ 225 mg (42.4%) | 180.0– 181.0 | (Nujol) 2340, 1709, 1550 1458, 1377, 156 |
| 85 | (V-3) 511 mg | H₂N(CH₂)₂N(iPr), 1.054 g | — | 105° C. 7 hr. | CH₂Cl₂MeOH/ NH₄OH = 128/16/1– 64/8/1 | Ia-85*¹ 436 mg (32.0%) | 125.0– 127.0 | (Nujol) 2668, 2500, 2400 (sh), 1702, 1619 1570, 1462, 1378 |
| 86 | (V-2) | HN(iBu), 1.50 g | — | 32 hr. | CH₂Cl₂MeOH = | Ia-86*¹ | 135.0– | (Nujol) |

TABLE 10-continued $$Cl(CH_2)_3-N\underset{\phantom{X}}{\bigcirc}-PhX \xrightarrow[(VIII)]{RH} R(CH_2)_3-N\underset{\phantom{X}}{\bigcirc}-PhX$$

(V)               (Ia)

| Ex. No. | (V) | (VIII) | solvent | reaction condition | purification condition | product mg (Yield) | m.p. (°C.) | IR |
|---|---|---|---|---|---|---|---|---|
|  |  | 654 mg |  | reflux | 49/1–19/1 | 338 mg (27.1%) | 136.5 | 2420, 1707, 1616 1572, 1485, 1456 1377 |
| 87 | (V-2) 645 mg | HN(iBu), 1.1 ml | — | 32 hr. reflux | CH$_2$Cl$_2$MeOH = 49/1–19/1 | Ia-87*1 338 mg (27.1%) | 135.0–136.0 (MeOH-Et$_2$O) | (Nujol) 2420, 1707, 1616 1572, 1485, 1456 1377 |
| 88 | (V-2) 1.05 g | ⌐NH⌐ | — | room temperature 32.5 hr. | CH$_2$Cl$_2$MeOH/ NH$_4$OH = 128/16/1– 32/4/0.5 | Ia-88*1 1.034 g (52.4%) | 176.0–178.0 (MeOH) | (Nujol) 3483, 2723, 2679 2587, 2415, 1703 1608, 1570, 1478 1460, 1412, 1382 |
| 89 | (V-2) 621 mg | ⌐NH⌐ | — | room temperature 5 days | CH$_2$Cl$_2$MeOH/ NH$_4$OH = 128/16/1 | Ia-89*1 800 mg (67.3%) | 190.0–191.0 (dec.) (MeOH) | (Nujol) 2355, 1711, 1620 1577, 1543, 1479 (sh), 1461, 1378 |
| 90 | (V-1) 828 mg | tetralin | — | 150° C. 3 hr. | CH$_2$Cl$_2$MeOH = 29/1–19/1 | Ia-90*1 1.025 g (58.0%) | 183.5–185.0 (CHCl$_3$-MeOH) | (Nujol) 2340, 1708, 1619 1568, 1528(sh), 1485, 1461 |
| 91 | (V-1) 628 mg | HN(iBu), 3.76 ml | — | 33 hr. reflux | CH$_2$Cl$_2$MeOH = 49/1–19/1 | Ia-91*1 685 mg (51.6%) | 176.5–178.0 (dec.) (MeOH-Et$_2$O) | (Nujol) 2620, 2510, 1690 1657, 1618, 1579 1533, 1488, 1460 1409, 1378 |

*1: maleate

EXAMPLE 92

4-(4-tert-Butylphenyl)-1-[3-{4-(pyrimidin-2-yl)piperazin-1-yl}propyl]-1,2,5,6-tetrahydropyridine (I a-92)

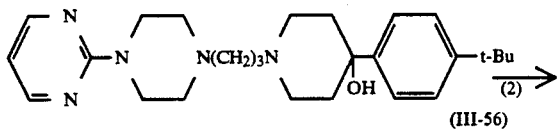

(1) A mixture of 1.1 g of 3-{4-pyrimidin-2-yl)piperazin-1-yl}propylchloride, 1.07 g of the compound (II-6), 1.26 g of K$_2$CO$_3$, and 1.03 g of NaI in 12 ml of DMF is stirred at 100° C. for 4 hours. The reaction mixture is poured into ice-water and extracted with ethyl acetate. The organic layer is washed with water, dried and evaporated. The residue is purified by silica gel chromatography (CH$_2$Cl$_2$/MeOH=10/1) followed by recrystallization from CH$_2$Cl$_2$-Et$_2$O to prepare 1.70 g (Yield: 85%) of the compound (III-56). mp. 215.0°–225.0° C. (dec.)

(2) A solution of 1.58 g of the compound (III-56) in 15 ml of CF$_3$COOH is refluxed for 3.5 hours. After removal of the excess reagent, the residue is poured into ice-cooled aq.NaHCO$_3$ and extracted. The organic layer is dried over Na$_2$SO$_4$ and evaporated under reduced pressure. The oily residue is purified by column chromatography with silica gel, eluting with CH$_2$Cl$_2$/MeOH (10/1–5/1) to prepare 1.44 g (Yield: 95%) of the compound (I a-92) as crystals (mp. 79.0°–81.0° C.) The maleate is recrystallized from methanol to prepare colorless needles. mp. 209.0°–211.0° C. (dec.)

EXAMPLE 93–94

The reactions are performed in the same manner as Example 92 to prepare the compound (III) and (I a). The reaction conditions and physical constants are shown in Tables 11 and 12.

TABLE 11

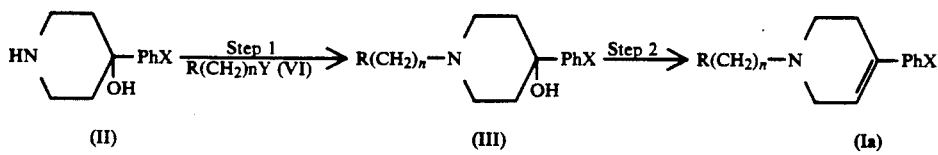

(Step 1)

| Ex. No. | (II) | R(CH₂)nY (VI) | DMF (ml) | K₂CO₃ (g) | NaI (g) | reaction condition (1) | purification condition (1) | g (Yield) Compd. No. | m.p. (°C.) |
|---|---|---|---|---|---|---|---|---|---|
| 93 | (II-6) 980 mg | Ph—N⟨ ⟩N(CH₂)₃Cl 1.0 g | 20 | 1.16 | 0.94 | 105 6.5 hr. | CH₂Cl₂/MeOH = 10/1–5/1 | 1.69 (92.6) (III-57) | 129.0– 130.5 (CH₂Cl₂- Et₂O) (maleate) |
| 94 | (II-6) 2.67 g | S⟨ ⟩N(CH₂)₃Cl 2.1 g | 20 | 3.18 | 2.60 | 95–100 17 hr. | CH₂Cl₂/MeOH = 20/1–10/1 | 4.04 (93.3) (III-58) | 137.0– 138.5 (CH₂Cl₂- Et₂O) (maleate) |

TABLE 12

(Step 2)

| (III) (g) | CF₃COOH | reflux time | purification condition | (I a) g (Yield) | m.p. (°C.) | IR |
|---|---|---|---|---|---|---|
| (III-57) 1.50 g | 20 ml | 4 hr. | CH₂Cl₂/MeOH = 20/1–10/1 | I a-93 1.40 g (97.4) | 105–106 (MeOH) | (Nujol) 1710, 1622, 1598, 1575, 1495 (sh), 1480, 1462, 1450, 1385, 1360 |
| (III-58) 0.88 g | 10 ml | 8 hr. | CH₂Cl₂/MeOH = 20/1 | I a-94 maleate 0.74 g (97.5) | 213.0– 214.5 (MeOH) | (Nujol) 2300, 1717, 1622, 1575, 1535, 1500, 1465, 1458, 1450 |

EXAMPLE 95

4-(4-Hydroxyphenyl)-1-{3-(4-morpholinyl)propyl}-1,2,5,6-tetrahydropyridine (I a-95)

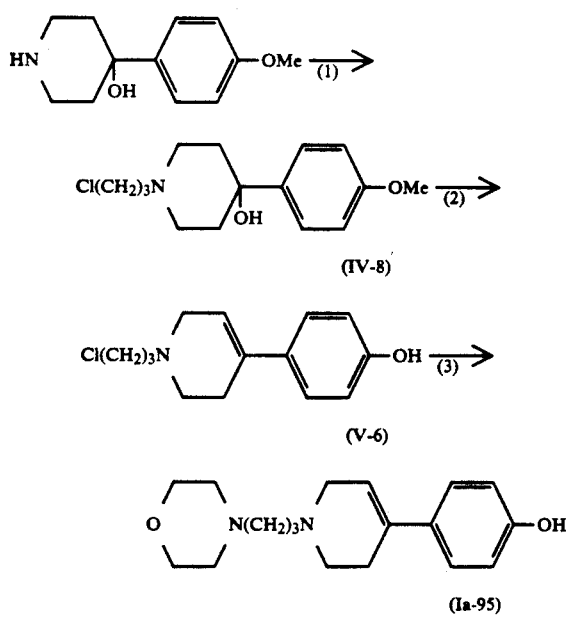

(1) A mixture of 2.829 g of 4-(4-methoxyphenyl)-4-hydroxypiperidine, 2.02 ml of 3-bromopropylchloride, and 3.773 g of K₂CO₃ in 30 ml of DMF is stirred at room temperature for 3 hours. The reaction mixture is poured into ice-water and extracted with ethyl acetate. The organic layer is dried and evaporated under reduced pressure to prepare 4:525 g of pale yellow solid. Purification is conducted by column chromatography with silica gel; eluting with CH₂Cl₂/MeOH (29/1–5/1) to prepare 3.316 g (Yield: 85.6%) of the compound (IV-8) as solid which is recrystallized from n-hexane-Et₂O to prepare colorless needles. mp. 103.5°–105.0° C.

Anal Calcd. (%) for $C_{15}H_{22}ClNO_2$: C,63.48; H,7.81; N,4.94; Cl,12.49 Found : C,63.47; H,7.78; N,5.01; Cl,12.45.

IR (CHCl₃) : 3595, 1610, 1582, 1510, 1468, 1462, 1454, 1441, 1375

NMR (CDCl₃) δ: 1.761 (d-d, $J_1=14$ Hz, $J_2=3$ Hz, 2H); 1.998 (quint, J=7 Hz, 2H); 2.121 (t-d, $J_1=13$ Hz, $J_2=4$ Hz, 2H); 2.475 (t-d, $J_1=12$ Hz, $J_2=3$ Hz, 2H); 2.560 (t, J=7 Hz, 2H); 2.782 (d-d, $J_1=14$ Hz, $J_2=3$ Hz, 2H); 3.618 (t, J=7 Hz, 2H); 3.805 (s, 3H); 6.866, 7.427 (ABq, J=9 Hz, 4H)

(2) To a solution of 3.176 g of the compound (IV-8) is added 3.17 ml of BBr₃ with stirring under ice-cooling. After refluxing for 1.5 hours, the reaction mixture is poured into ice-water and the aqueous layer is made alkaline with c.NH₄OH and extracted with CH₂Cl₂/MeOH (4/1). The organic layer is dried and evaporated to dryness. The crude product is dissolved in 20 ml of CF₃COOH and refluxed for 1 hour. The reaction mixture is concentrated under reduced pressure and poured into ice-water. The aqueous layer is made alkaline with c.NH₄OH and extracted with CH₂Cl₂/MeOH (4/1). The organic layer is dried and evaporated to prepare 1.701 g (Yield: 57.2%) of the compound (V-6) as solid, which is recrystallized from MeOH-n-hexane to prepare the compound (V-6) as pale orange plates. mp. 208.0°–209.0° C.

Anal Calcd. (%) for $C_{14}H_{18}ClNO$: C,66.79; H,7.21; N,5.56; Cl,14.08. Found: C,66.79; H,7.26; N,5.52; Cl,14.25.

IR(Nujol): 3025, 2773, 2650, 2560, 1607, 1578, 1515, 1453, 1429, 1382

NMR (CDCl₃–CD₃OD) δ: 2.66 (quint, J=8 Hz, 2H); 2.47-2.76 (m, 4H); 2.774 (t, J=6 Hz, 2H); 3.200 (q, J=2 Hz, 2H); 3.637 (t, J=6 Hz, 2H); 5.972 (s, 1H); 6.803, 7.275 (ABq, J=9 Hz, 4H)

(3) A stirred mixture of 1.482 g of the compound (V-6) and 2.57 ml of morpholine is refluxed for 2 hr.15 min. After removal of the reagent, the residue is purified by column chromatography with silica gel, eluting with CH₂Cl₂/MeOH/NH₄OH (128/16/1-64/8/1) to give 1.047 g (Yield: 58.8%) of the compound (I a-95) as a solid. The maleate is recrystallized from MeOH-Et₂O to prepare pale yellow plates. mp. 166.0°–167.5° C. (d.)

Anal Calcd. (%) for $C_{18}H_{26}N_2O_2 \cdot 2C_4H_4O_4$: C,58.22; H,6.48; N,5.35. Found: C,58.42; H,6.41; N,5.24.

IR (Nujol): 3230, 3063, 2725, 2355, 1715, 1625, 1579, 1519, 1464, 1387

NMR (CD₃OD) δ: 2.13-2.35 (m, 2H); 2.866 (brs, 2H); 3.03-3.25 (m, 6H); 3.25-3.40 (m, 2H); 3.564 (t, J=6 Hz, 3H); 3.883 (t, J=5 Hz, 4H); 3.953 (brs, 2H); 5.999 (brs, 1H); 6.264 (s, 4H); 6.778, 7.320 (ABq, J=9 Hz, 4H)

EXAMPLE 96

4-(4-Hydroxyphenyl)-1-{3-(1-pyrrolidinyl)propyl}-1,2,5,6-tetrahydropyridine (I a-96)

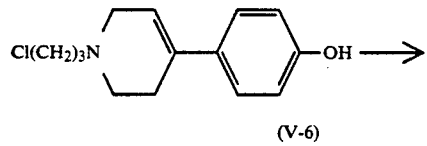

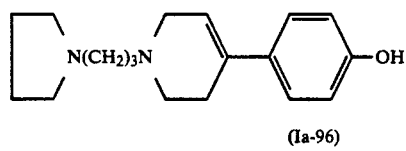

A mixture of 1.50 g of the compound (V-6) and 4.97 ml of pyrrolidine is stirred at room temperature for 18.5 hours and treated in the same manner as Example 95 (3) to prepare 2.041 g (Yield: 66.1%) of the maleate of the compound (I a-96) as needles. mp. 145.0°–147.0° C. (dec.)

Anal Calcd. (%) for $C_{18}H_{25}N_2O \cdot 2C_4H_4O_{44}$: C, 60.03; H, 6.42; N,5.50. Found: C, 60.22; H, 6.61; N, 5.40.

IR (Nujol): 3230, 3041, 2710(sh), 2590, 2360, 1709, 1622, 1578, 1518, 1461, 1377

NMR (CD₃OD) δ: 2.00-2.175 (m, 4H); 2.175-2.375 (m, 2H); 2.859 (brs, 2H); 3.23-3.48 (m, 8H); 3.542 (t, J=6 Hz, 3H); 3.992 (brs, 2H); 5.995 (brs, 1H); 6.257 (s, 4H); 6.778, 7.320 (ABq, J=8 Hz, 4H)

EXAMPLE 97

1-{3-(N-methylamino)propyl}-4-(4-hydroxyphenyl)-1,2,5,6-tetrahydropyridine (I a-97)

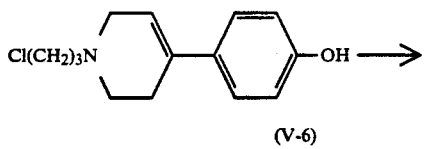

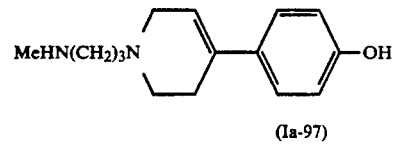

A mixture of 3.00 g of the compound (V-6) and 11.84 ml of BuNH₂ is refluxed for 5 hours, and treated in the same manner as Example 96 to prepare 2.188 g (Yield: 63.7%) of the compound (I a-97) as needles. mp. 233.0°–236.0° C. (dec.)

IR (Nujol): 3425, 3055, 2778, 2670, 2582, 1665, 1613, 1590, 1515, 1471, 1453, 1439, 1428

NMR (CDCl₃): 0.920 (d, J=7 Hz, 6H); 1.92-2.18 (m, 3H); 2.554 (brs, 2H); 2.692 (d, J=7 Hz, 2H); 2.751 (t, J=6 Hz, 2H); 2.854 (t, 2H); 2.854 (t, J=6 Hz, 2H); 3.134 (t, J=6 Hz, 2H); 3.247 (brs, 2H); 5.922 (brs, 1H); 6.818, 7.194 (ABq, J=9 Hz, 4H)

EXAMPLE 98

1-{3-(N-isobutyl-N-methylamino)propyl}-4-(4-hydroxyphenyl)-1,2,5,6-tetrahydropyridine (I a-98)

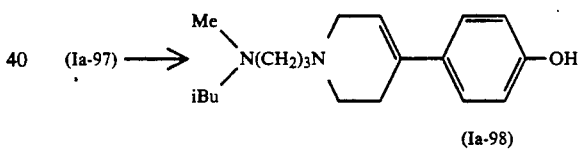

Treatment of 2.138 g of the compound (I a-97) in the same manner as Example 34 prepares 1.528 g (Yield: 70.1%) of the compound (I a-98) as solid, which is crystallized as maleate and recrystallized from MeOH-Et₂O to prepare pale yellow plates. mp.150.0°–153.0° C. (dec.)

Anal Calcd. (%) for $C_{19}H_{30}N_2O \cdot 2C_4H_4O_4$: : C, 60.38; H, 7.16; N, 5.38. Found: C, 60.66; H, 7.16; N, 5.24.

IR (Nujol): 3235, 2700(sh), 2400, 1618, 1576, 1517, 1459, 1380 (sh), 1372(sh), 1359

NMR (CD₃OD) δ: 1.051 (d, J=7 Hz, 6H); 2.025-2.400 (m, 3H); 2.852 (brs, 2H); 2.916 (s, 3H); 3.026 (d, J=7 Hz, 2H); 3.15-3.38 (m, 4H); 3.533 (t, J=6 Hz, 2H); 3.917 (brs, 2H); 5.995 (brs, 1H); 6.257 (s, 4H); 6.777,7.318 (ABq, J=9 Hz, 4H)

EXAMPLE 99

4-(4-Methoxyphenyl)-1-{3-(4-morpholinyl)propyl}-1,2,5,6-tetrahydropyridine (I a-99)

(IV-8) ⟶

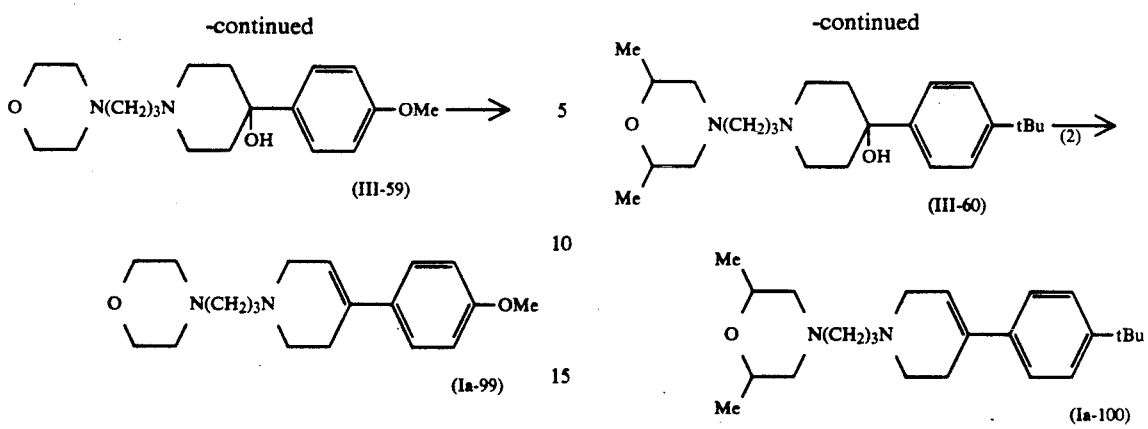

A stirred mixture of 1.147 g of the compound (IV-8) and 1.76 ml of morpholine is refluxed for 1 hour. After removal of the reagent, the residue is purified by silica gel column chromatography ($CH_2Cl_2$/MeOH/$NH_4OH$=64/8/1-32/6/1) to prepare 1.34 g of the compound (III-59) as oily substance. The oily product is dissolved in 10 ml of $CF_3COOH$ and refluxed for 1 hour. After removal of the reagent, the residue is poured into aq. $NH_4OH$ and extracted with methylene chloride. The organic layer is dried and evaporated under reduced pressure to prepare 1.012 g of the oily product. The oily product is subjected to column chromatography with silica gel; eluting with $CH_2Cl_2$/MeOH(19/1). The eluate is recrystallized from $Et_2O$-n-hexane to prepare of 637 mg (Yield: 50.2%) of the compound (I a-99) as colorless needles. mp. 69.0°–70.5° C.

Anal Calcd. (%) for $C_{19}H_{28}N_2O_2$: C, 72.12; H, 8.92; N, 8.85. Found: C, 72.01; H, 8.88; N, 9.05.

IR ($CHCl_3$): 2490, 1610, 1572, 1512, 1466, 1446, 1417, 1402, 1378

NMR ($CHCl_3$) δ: 1.799 (quint, J=7 Hz, 2H); 2.33–2.63 (m, 10H); 2.7 06 (t, J=5 Hz, 2H); 3.151 (q, J=4 Hz, 2H); 3.725 (t, J=5 Hz, 4H); 3.802 (s, 3H); 5.969 (quint, J=2 Hz, 1H); 6.851, 7.322 (ABq, J=9 Hz, 4H)

Example 100

4-(4-tert-Butylphenyl)-1-{3-(2,6-dimethylmorpholino)propyl}-1,2,5,6-tetrahydropyridine (I a-100)

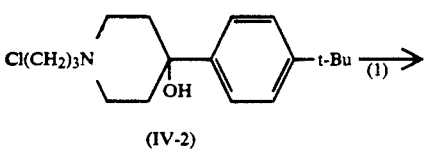

(1) A mixture of 1.150 g of the compound (IV-2) and 2.29 ml of cis 2,6-dimethylmorpholine is stirred at 103°–135° C. for 4 hours. After removal of the reagent, the residue is poured into aq.NaOH and extracted with methylene chloride. The organic layer is dried and evaporated under reduced pressure. The residue is purified by column chromatography with silica gel, eluting with $CH_2Cl_2$-MeOH (15/1-5/1) to prepare 1.37 g (Yield: 95.0%) of the compound (III-60) as crystals. mp. 137.5°–138.0° C. (dec.)

IR ($CHCl_3$): 3610, 3010, 2970, 2870, 2820, 1780, 1605, 1512 cm$^{-1}$

NMR ($CDCl_3$) δ: 1.161 (d, J=6 Hz, 6H); 1.319 (s, 9H); 1.63-1.88 (m, 7H); 2.215 (td, $J_1$=13 Hz, $J_2$=4 Hz, 2H); 2.30–2.60 (m, 6H); 2.753 (dd, $J_1$=12 Hz, $J_2$=2 Hz, 2H); 2.875 (dd, $J_1$=11 Hz, $J_2$=2 Hz, 2H); 3.60–3.75 (m, 2H); 7.377,7.451 (ABq, J=9 Hz, 4H)

(2) A solution of 1.35 g of the compound (III-60) in 10 ml of $CF_3COOH$ is refluxed for 4 hour. After removal of the reagent, the residue is poured into aq.$NaHCO_3$ and extracted with ethyl acetate. The organic layer is washed with water, dried and evaporated under reduced pressure. The oily residue is purified by column chromatography with silica gel, eluting with $CH_2Cl_2$/MeOH (25/1-15/1) to prepare. 1.29 g (Yield: 86.8%) of the compound (I a-100) as an oil. The maleate is recrystallized from MeOH-iPrOH to prepare colorless needles. mp. 192.0°–193.0° C.

Anal Calcd. (%) for $C_{24}H_{38}N_2O$. $2C_4H_4O_4$: C, 63.58; H, 7.79; N, 4.64. Found: C, 63.77; H, 7.69; N, 4.65.

IR (Nujol): 1707, 1618 cm$^{-1}$

NMR ($CDCl_3$): 1.260 (d, J=7 Hz, 6H); 1.330 (s, 9H); 2.20–2.40 (m, 2H); 2.491 (t, J=12 Hz, 2H); 2.80–2.95 (m, 2H); 3.111 (t, J=8 Hz, 2H); 3.28–3.40 (m, 4H); 3.542 (t, J=6 Hz, 2H); 3.80–4.00 (m, 4H); 3.542 (t, J=6 Hz, 2H); 3.80–4.00 (m, 4H); 6.02–6.08 (m, 1H); 6.283 (s, 2H); 7.355,7.422 (ABq, J=9 Hz, 4H)

EXAMPLE 101-104

The reaction is performed in the same manner as Example 100 to prepare the compound (I a). The reaction conditions are shown in Tables 13 and 14.

TABLE 13

Reaction scheme:

Cl(CH₂)₃N[piperidine]-PhX(p) with OH + (XI) R-Z-NH-R → (1) → Z-N(CH₂)₃N[piperidine]-PhX with OH → (2) → Z-N(CH₂)₃N[piperidine]-PhX (IV) → (III) → (Ia)

| Ex. No. | (IV) | (XI) | solvent | reaction condition | purification condition | product g (Yield) | m.p. (°C.) | IR |
|---|---|---|---|---|---|---|---|---|
| 101 | X = Me 3.55 g | Z = O, R = H 5.77 g | — | 2 hr. reflux | CH₂Cl₂/MeOH = 15/1–5/1 | III-61 4.23 g (96.0%) | 103.0– 104.5 | (CHCl₃) 3600, 3020, 2950, 2920, 2820, 1513, 1472 |
| 102 | X = Cl 5.1 g | Z = O, R = H 7.71 g | — | 130–135° C. 2.5 hr. | — | III-62 5.97 g (99.5%) | 236.0– 237.0 | (Nujol) 3440, 2930, 2870, 2640, 2550, 2460 |
| 103 | X = t-Bu 2.35 g | Z = NH, R = Me 1.73 g | DMF 20 ml | 95–100° C. 2 hr. | CH₂Cl₂/MeOH/ NH₄OH = 30/6/1 | III-63 1.92 g (65.3%) | — | (CHCl₃) 3000, 3330, 2960, 2820, 2470, 1665, 1635, 1605, 1590, 1510 |
| 104 | X = Cl 2.05 g | Z = NH, R = Me 1.62 g | DMF 15 ml | 80–85° C. 3.5 hr. | CH₂Cl₂/MeOH/ NH₄OH = 32/6/1 | III-64 2.10 g (80.9%) | — | (CHCl₃) 3590, 3160, 2930, 2810, 2490, 1677, 1596, 1492 |

TABLE 14

| Ex. No. | (III) | CF₃COOH | reaction condition | purification condition | product g (Yield) | m.p. (°C.) | IR |
|---|---|---|---|---|---|---|---|
| 101 | (III-61) 4.45 g | 45 ml | 2.5 hr. reflux | CH₂Cl₂/MeOH = 15/1–5/1 | Ia-101 3.99 g (92.0%) | 186.5– 188.5*¹ | (Nujol) 1709, 1621 |
| 102 | (III-62) 3.78 g | 45 ml | 7 hr. reflux | CH₂Cl₂/MeOH = 15/1–5/11 | Ia-102 3.00 g (84.2%) | 185.5– 186.5*¹ | (Nujol) 2300(br), 1709, 1622 |
| 103 | (III-63) 1.92 g | 20 ml | room temperature 2.5 hr. reflux | CH₂Cl₂/MeOH/ NH₄OH = 128/16/1 | Ia-103 1.60 g (87.4%) | 235.0– 250.0*² | (Nujol) 3440, 3410, 2670, 2580, 2470, 2420, 1658, 1555, 1507 |
| 104 | (III-64) 2.10 g | 25 ml | room temperature 15 hr. reflux | CH₂Cl₂/MeOH/ NH₄OH = 128/16/1 | Ia-104 1.79 g (89.6%) | 179.0– 181.0*² | (Nujol) 3600, 2680, 2530, 2440, 1642, 1597, 1496 |

*¹maleate
*²hydrochloride

EXAMPLE 105

1-[3-{4-(3,4-Dimethoxyphenyl)-1,2,5,6-tetrahydropyridin-1-yl}propylcarbamoyl]-2-oxopyrrolidine (I a-105)

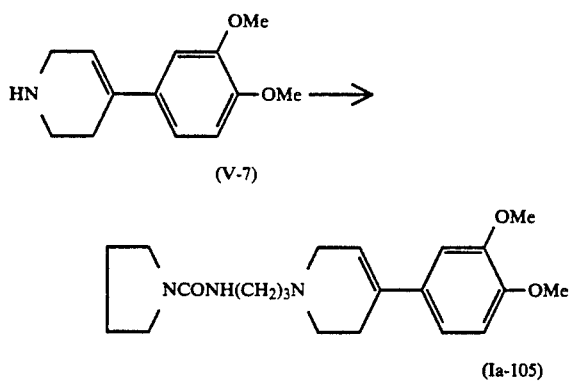

To a solution of 3.76 g of 4-(3,4-dimethoxyphenyl)-1,2,5,6-tetrahydropyridine (V-7), which was prepared by the reaction of 4-hydroxy-4-(3,4-dimethoxyphenyl)-piperidine and p-toluenesulfonic acid, and 2.94 g of 1-(3-chloropropylcarbamoyl)-2-oxopyrrolidine in 35 ml of DMF is added 3.98 g of K₂CO₃ and 3.22 g of NaI. The reaction mixture is stirred at 100°–105° C. for 6 days under nitrogen gas. After cooling to room temperaure, the mixture is diluted with ethyl acetate, washed with brine and dried over MgSO₄. After removal of the solvent, the residue is subjected to column chromatography with silica gel, eluting with CH₂Cl₂/MeOH (20/1) to prepare 1.78 g (Yield: 33.4%) of the compound (I a-105) as solid. The oxalate is recrystallized from iPrOH-MeOH to prepare needles. mp. 178.0°–182.0° C.

Anal Calcd. (%) for C₂₃H₃₁N₃O₈.1/5 H₂O: C, 57.35; H, 6.33; N, 8.67. Found: C, 57.42; H, 6.58; N, 8.73.

IR (Nujol): 3310, 1725(sh), 1708, 1682, 1675, 1600, 1580, 1545, 1545, 1520

NMR (CDCl₃): 1.764 (quint, J=7 Hz, 2H); 1.954 (quint, J=8 Hz, 2H); 2.44–2.51 (m, 4H); 2.530 (t, J=8 Hz, 2H); 2.646 (t, J=5 Hz, 2H); 3.094 (q, J=3 Hz, 2H); 3.328 (q, J=7 Hz, 2H); 3.795 (t, J=7 Hz, 2H); 3.809, 3.827 (sx2, 6H); 5.915 (quint, J=3 Hz, 1H); 6.755 (d, J=9 Hz, 2H); 6.84–6.89 (m, 2H); 8.434 (brs, 1H)

EXAMPLE 106

1-[3-{4-(4-Methoxyphenyl)-1,2,5,6-tetrahydropyridin-1-yl}-propylcarbamoyl]-2-oxopyrrolidine (I a-106)

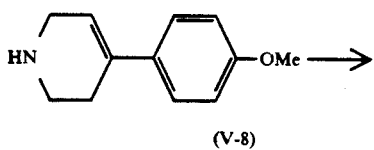

(V-8)

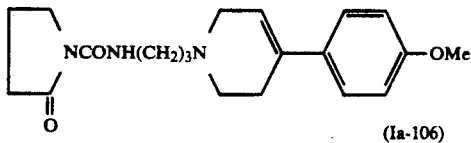

(Ia-106)

The compound (V-8) is reacted in the same manner as Example 105 to prepare the compound (I a-106). mp. 199.5°–200.0° C. (dec.)

Anal Calcd. (%) for $C_{22}H_{29}N_3O_7$: C, 58.81; H, 6.31; N, 9.32. Found: C, 59.02; H, 6.53; N, 9.39.

IR (Nujol): 3300, 2730, 2620, 1700, 1685, 1612, 1548, 1529, 1465

NMR (CDCl$_3$): 1.90–2.10 (m, 4H); 2.590 (t, J=7 Hz, 2H); 2.80–2.86 (m, 2H); 3.23–3.30 (m, 2H); 3.33–3.52 (m, 4H); 3.778 (s, 3H); 3.898 (m, 2H); 5.995 (s, 1H); 6.893, 7.379 (ABq, J=8 Hz, 4H)

EXAMPLE 107

1-[{-(4-Tolyl)-1,2,5,6-tetrahydropyridin-1-yl}butylcarbamoyl]-2-oxopyrrolidine (I a-107)

(II-8) 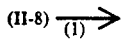

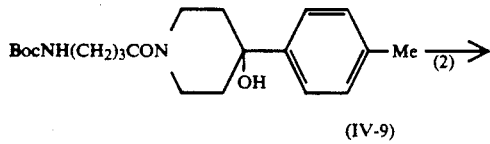

(IV-9)

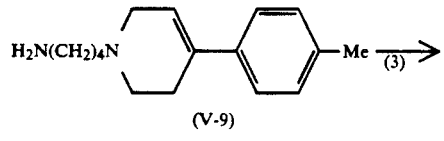

(V-9)

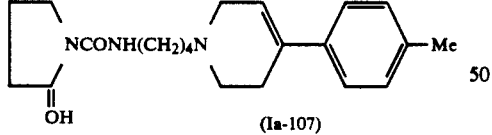

(Ia-107)

(1) To a solution of 4.00 g of the compound (II-8) and 4.675 g of N-Boc-β-alanine in 90 ml of THF are added 5.178 g of 1,3-dicyclohexylcarbodiimide and 848 mg of 1-hydroxybenzotriazole hydrate. The reaction mixture is stirred at room temperature for 2 hours and 10 minutes. After removal of precipitates, the reaction mixture is concentrated under reduced pressure. The residue is poured into d.HCl and extracted with CH$_2$Cl$_2$. The organic layer is washed with aq.NaHCO$_3$ and water in order, dried over MgSO$_4$ and evaporated under reduced pressure. The residue is subjected to column chromatography with silica gel, eluting with toluene-/acetone (3/1–2/1) to prepare 6.862 g of crystalline residue. It is recrystallized from methylene chloride-ether-n-hexane to prepare 6.674 g (Yield: 84.8%) of the compound (IV-9) as colorless needles. mp. 161.5°–163.0° C.

Anal calcd. (%) for $C_{21}H_{32}N_2O_4$: C, 67.18; H, 8.46; N, 7.50. Found: C, 66.99; H, 8.57; N, 7.44.

IR (CHCl$_3$): 3597, 3457, 1709, 1628, 1508, 1474, 1448, 1393, 1369

NMR (CDCl$_3$) δ: 1.432 (s, 9H); 1.75,2.05 (m, 8H); 2.344 (s, 3H); 2.147 (t, J=7 Hz. 2H); 3.04,3.20 (m, 3H); 3.560 (td, J$_1$=12 Hz, J$_2$=4 Hz, 1H); 3.737 (d, J=14 Hz, 1H); 4.548 (d, J=13 Hz, 1H); 4.833 (brs, 1H); 7.177,7.353 (ABq, J=8 Hz, 4H)

(2) A solution of 6.654 g of the compound (IV-9) in 13 ml of CF$_3$COOH is stirred at room temperature for 2.5 hours. After removal of the excess reagent, 6.36 g of the crystalline residue is obtained. The residue is recrystallized from MeOH-Et$_2$O to prepare 5.798 g of colorless plates. Then to a solution of 4.818 g of the plates in 30 ml of methanol is added 5 ml of triethylamine. After removal of the solvent to dryness, the resulting solid is dropwise added to a stirred suspension of 737 mg of LiAlH$_4$ in 80 ml of THF at room temperature and stirred at the same temperature for 2.5 hours. After decomposition of the excess reagent by careful addition of water, the resulting precipitate is filtered off. The organic layer is evaporated to dryness to prepare 3.612 g of the yellow oily residue. The residue is subjected to column chromatography with silica gel, eluting with CHCl$_3$/MeOH/c.NH$_4$OH (32/4/0.5–32/6/1) to prepare 1.341 g (Yield: 42.4%) of the compound (V-9).

(3) A mixture of 1.341 g of the compound (V-9) and 1.126 g of 1-phenoxycarbonyl-2-oxopyrrolidine is heated at 115° C. for 1 hour 43 minutes. The reaction mixture is purified by column chromatography with silica gel, eluting with toluene/acetone (2/1– 1/1) followed by recrystallization from Et$_2$O-n-hexane to prepare 540 mg (Yield: 24.7%) of the compound (I a-107) as prisms. mp. 104.0°–104.5° C.

Anal Calcd. (%) for $C_{21}H_{29}N_3O_2$: C, 71.05; H, 8.22; N, 11.84. Found: C, 70.95; H, 8.22; N, 11.82.

IR (CHCl$_3$): 3325, 1714, 1682, 1602, 1548, 1516, 1490, 1461, 1442, 1387

NMR (CDCl$_3$) δ: 1.62,1.66 (m, 4H); 2.025 (quint, J=7 Hz, 2H); 2.330 (s, 3H); 2.30–2.73 (m, 8H); 3.145 (q, J=3 Hz, 2H); 3.338 (q, J=6 Hz, 2H); 3.858 (t, J=7 Hz, 2H); 6.016 (quint, J=2 Hz, 1H); 7.11 7, 7.283 (ABq, J=8 Hz, 4H); 8.430 (brs, 1H)

EXAMPLE 108

1-[{5-(4-Tolyl)-1,2,5,6-tetrahydropyridin-1-yl}pentylcarbamoyl]-2-oxopyrroridine (I a-108)

(II-8) 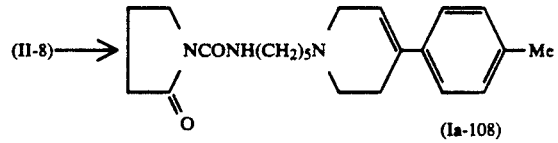

(Ia-108)

A mixture of 4.675 g of BocNH(CH$_2$)$_4$COOH and 4.00 g of the compound (II-8) is treated in the same manner as Example 107 (1)–(3) to prepare 392 mg (Yield: 15.0%) of the compound (I a-108). mp. 58.5°–59.5° C.

Anal Calcd. (%) for $C_{22}H_{31}N_3O_2$: C, 71.23; H, 8.42; N, 11.46. Found: C, 71.51; H, 8.46; N, 11.37.

IR (CHCl$_3$): 3321, 1714, 1681, 1548, 1516, 1489, 1461, 1387

NMR (CDCl$_3$—CD$_3$OD) δ: 1.32–1.45 (m, 2H); 1.52–1.70 (m, 4H); 2.039 (quint, J=7 Hz, 2H); 2.333 (s, 3H); 2.429–2.507 (m, 2H); 2.615 (t, J=8 Hz, 4H); 2.723 (t, J=6 Hz, 2H); 3.161 (q, J=3 Hz, 2H); 3.303 (q, J=6 Hz, 2H); 3.854 (t, J=7 Hz, 2H); 6.032 (s, 1H); 7.126, 7.292 (ABq, J=8 Hz, 4H); 8.460 (brs, 1H)

EXAMPLE 109

1-{3-(3,4-Dichlorophenoxy)propyl}-4-(4-hydroxyphenyl)-1,2,5,6-tetrahydropyridine (I a-109)

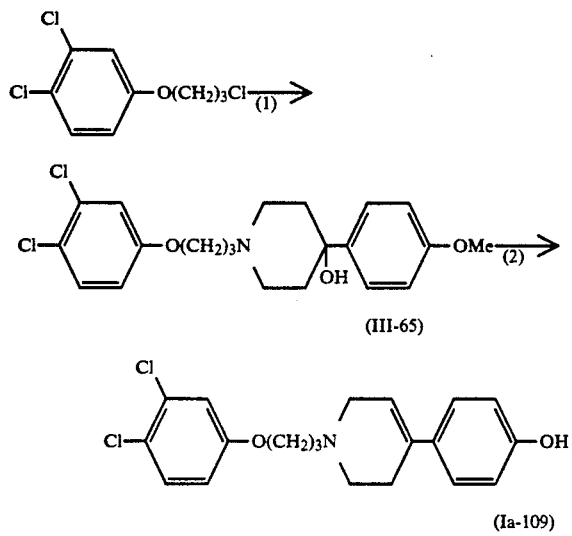

(1) A mixture of 3.6 g of 3-(3,4-dichlorophenoxy)propylchloride, which was prepared by the reaction of 3,4-dichlorophenol with 3-bromopropylchloride, and 3.12 g of 4-hydroxy-4-(4-methoxyphenyl)piperidine, 4.15 g of K$_2$CO$_3$, and 3.37 g of NaI in 35 ml of DMF is stirred at 105° C. for 10 hour. The reaction mixture is poured into ice-water, and the resulting precipitates are extracted with methylene chloride. The organic layer is dried and evaporated under reduced pressure. The residue is purified by column chromatography with silica gel, eluting with CH$_2$Cl$_2$/MeOH (20/1–10/1) followed by recrystallization from methylene chloride to prepare 5.86 g (Yield: 95.2%) of the compound (III-65) as colorless needles. mp. 131.0°–132.0° C.

Anal Calcd. (%) for C$_{21}$H$_{25}$N$_2$O$_3$Cl$_2$: C, 61.39; H, 6.20; N, 3.55; Cl, 17.28. Found: C, 61.47; H, 6.14; N, 3.41; Cl, 17.30.

IR (CHCl$_3$): 3600, 1612, 1595, 1568, 1513, 1480(sh), 1468

NMR (CDCl$_3$) δ: 1.563 (s, 1H); 1.772 (dd, J$_1$=14 Hz, J$_2$=3 Hz, 2H); 1.999 (quint, J=6 Hz, 2H); 2.137 (td, J$_1$=13 Hz, J$_2$=4 Hz, 2H); 2.478 (td, J$_1$=12 Hz, J$_2$=2 Hz, 2H); 2.575 (t, J=7 Hz, 2H); 2.811 (J$_1$=11 Hz, J$_2$=3 Hz, 2H); 3.803 (s, 3H); 4.004 (t, J=6 Hz, 2H); 6.760 (dd, J$_1$=9 Hz, J$_2$=3 Hz, 1H); 6.887 (d, J=9 Hz, 2H); 7.013 (d, J=3 Hz, 1H); 7.308 (d, J=9 Hz, 1H); 7.438 (d, J=9 Hz, 2H)

(2) To a stirred solution of 2.08 g of the compound (III-65) in 50 ml of methylene chloride is added 1.44 ml of BBr$_3$ under ice-cooling. After removal of the reagent, the residue is poured into aq.NaHCO$_3$ and extracted with ethyl acetate. The organic layer is washed with water, dried and evaporated under reduced pressure. The resulting oily residue 1.91 g is dissolved in 20 ml of CF$_3$COOH and refluxed for 2 hour. After removal of the reagent, the residue is poured into aq.NaHCO$_3$ and extracted with ethylacetate. The organic layer is washed, dried and evaporated. The residue is purified by column chromatography with silica gel, (toluene/ethyl acetate(1/1)—CH$_2$Cl$_2$/MeOH (20/1)) to prepare 270 mg (Yield: 33%) of the compound (I a-109) as a solid. The maleate is recrystallized from MeOH-iPrOH to prepare needles. mp. 167.0°–168.0° C. (dec.)

Anal Calcd. (%) for C$_{20}$H$_{21}$NO$_2$Cl$_2$: C,58.08; H,5.05; N,2.93; Cl,14.55. Found: C,58.31; H,5.10; N,2.83; Cl,14.34.

EXAMPLE 110

1-{3-(3,4-Dichlorophenoxy)propyl}4-(3,4-dichlorophenyl)-1,2,5,6-tetrahydropyridine (I a-110)

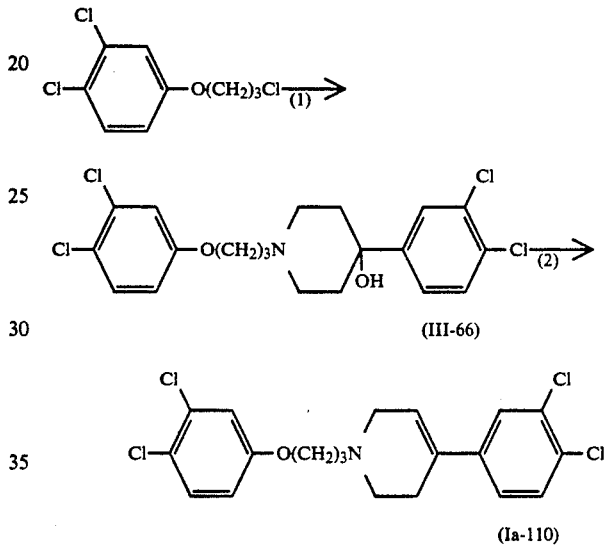

(1) 3-(3,4-dichlorophenoxy)propylchloride 1.38 g and 4-hydroxy-4-(3,4-dichlorophenyl)piperidine 1.35 g are reacted in the same manner as Example 109 (1) to prepare 2.40 g (Yield: 97.5%) of 1-{3-(3,4-dichlorophenoxy)propyl}-4-hydroxy-4-(3,4-dichlorophenyl) piperidine (III-66). mp. 118.0°–118.5° C.

(2) A solution of 1.61 g of the compound (III-66) in 20 ml of trifluoroacetic acid is refluxed for 3.5 hours. After removal of the reagent, the residue is poured into aq.NaHCO$_3$ and extracted with methylene chloride. The organic layer is washed, dried and evaporated. The residue is purified by column chromatography with silica gel; eluting with CH$_2$Cl$_2$/MeOH(25/1) to prepare 1.45 g (Yield 94.0%) of the compound (I a-110) as oxalate. The oxalate is recrystallized from MeOH-iPrOH to prepare the compound (I a-110) as needles. mp. 163.5°–165.0° C. (dec.)

Anal Calcd. (%) for C$_{20}$H$_{19}$NO$_2$Cl$_4$: C, 50.43; H, 4.09; N, 2.72; Cl, 27.15. Found: C, 50.70; H, 4.06; N, 2.69; Cl, 27.21.

IR (Nujol): 2930, 1713, 1695(sh), 1615, 1597, 1563

NMR (CDCl$_3$): 2.045 (quint, J=7 Hz, 2H); 2.657 (t, J=8 Hz, 2H); 2.554 (m, 2H); 2.745 (t, J=5 Hz, 2H); 3.202 (q, J=3 Hz, 2H); 4.026 (t, J=6 Hz, 2H); 6.110 (m, 1H); 6.766 (dd, J$_1$=19 Hz, J$_2$=3 Hz, 1H); 7.015 (d, J=3 Hz, 1H); 7.19–7.47 (m, 4H)

EXAMPLE 111

1-{3-(3,4-Dichlorophenoxy)propyl}-4-(4-trifluoromethylphenyl)-1,2,5,6-tetrahydropyridine (I a-111)

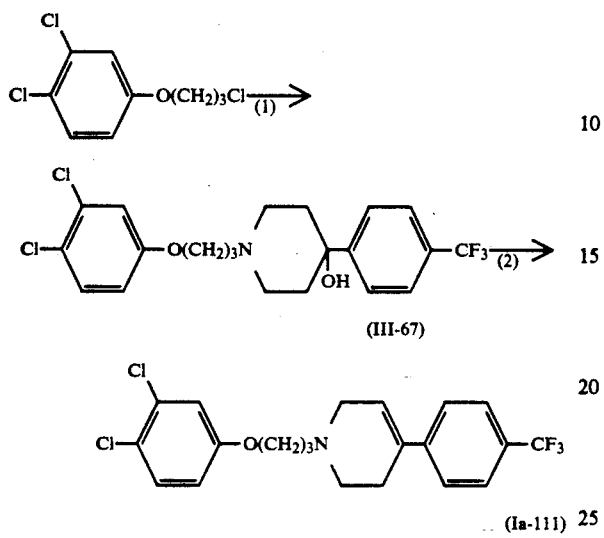

(1) 3-(3,4-dichlorophenoxy)propylchloride 2.00 g and 4-hydroxy-4-(4-trifluoromethylphenyl)piperidine 1.95 g are reacted in the same manner as Example 109 (1) to prepare 3.16 g (Yield: 88.7%) of the compound (III-67). mp. 196.0°-196.5° C.

(2) A solution of 2.65 g of the compound (III-67) in 30 ml of trifluoroacetic acid is refluxed for 41 hours. After removal of the reagent, the residue is poured into aq.-NaHCO₃ and extracted with ethyl acetate. The organic layer is dried and evaporated. The residue is purified by column chromatography with silica gel. (toluene/ethyl acetate (3/1), CH₂Cl₂/MeOH(25/1)) to prepare 1.65 g (Yield: 65.9%) of the compound (I a-111) as a solid, which is recrystallized from Et₂O to prepare colorless needles, mp. 83.5°-84.0° C. The oxalate melts at mp. 195.5°-196.0° C.

Anal Calcd. (%) for $C_{21}H_{20}NO_2Cl_2F_3 \cdot C_2H_2O_4$: C, 52.93; H, 4.33; N, 2.71; Cl, 13.42; F, 11.08. Found: C, 53.09; H, 4.26; N, 2.69; Cl, 13.65; F, 10.95.

IR (CHCl₃): 2950, 2930, 2830, 2790, 1618, 1597, 1469

NMR (CDCl₃): 2.052 (quint, J=7 Hz, 2H); 2.52–2.65 (m, 2H); 2.661 (t, J=7 Hz, 2H); 2.759 (t,J=6 Hz, 2H); 3.222 (q, J=3 Hz, 2H); 6.171 (m, 1H); 6.765 (dd, J₁=9 Hz, J₂=3 Hz, 1H); 7.015 (d, J=3 Hz, 1H); 7.312 (d, J=9 Hz, 1H); 7.479, 7.574 (ABq, J=8 Hz, 4H)

REFERENCE EXAMPLE 1

4-Hydroxy-4-(3,4-dichlorophenyl)piperidine (II-1)

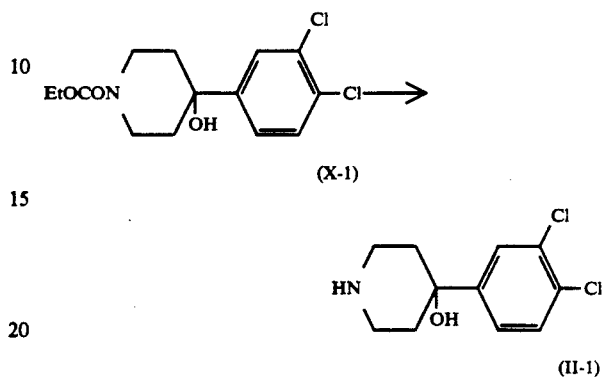

A mixture of 64.2 g of 1-ethoxycarbonyl-4-hydroxy-4-(3,4-dichlorophenyl)piperidine (X−1) and a solution of 72.4 g of KOH in 700 ml of nBuOH is refluxed for 2 hours and evaporated. The reaction mixture is concentrated under reduced pressure and extracted with ethyl acetate. The organic layer is washed with water, dried and evaporated. The resulting crystalline residue is recrystallized from ethyl acetate to prepare 44.7 g (Yield: 90.0%) of the compound (II-1). mp. 144.5°-146.0° C.

Anal Calcd. (%) for $C_{14}H_{17}NO_3Cl_2$: C, 53.62; H, 5.26; N, 5.68; Cl, 28.98. Found: C, 53.68; H, 5.32; N, 5.69; Cl, 28.81.

IR (Nujol): 3320, 3100, 1438

NMR (CD₃OD) δ: 1.651 (dd, J₁=12 Hz, J₂=2 Hz, 2H); 1.936 (td, J₁=12 Hz, J₂=5 Hz, 2H); 1.651 (dd, J₁=12 Hz, J₂=2 Hz, 2H); 3.074 (td, J₁=12 Hz, J₂=3 Hz, 2H); 7.402 (dd, J₁=8 Hz, J₂=2 Hz, 1H); 7.480 (d, J=8 Hz, 1H); 7.662 (d, J=2 Hz, 1H)

REFERENCE EXAMPLE 2-19

The reaction is performed in the same manner as Reference Example 1 to prepare the compound (II). The reaction conditions and physical constants are shown in Tables 15 and 16.

TABLE 15

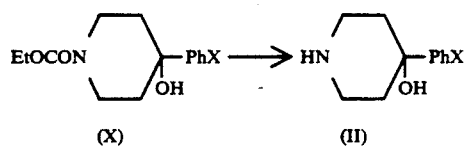

| Ref. Ex. No. | (X) X = | Base | solvent | reflux time | (II) g (Yield) m.p. (°C.) | IR |
|---|---|---|---|---|---|---|
| 2 | CF₃ (p) 27.3 g (X-2) | KOH (28.07 g) | EtOH (450 ml) | 5 hours | (II-2) 13.24 g (63.0%) | |
| 3 | n-Pr (p) 44.0 g (X-3) | KOH (49.3 g) | n-BuOH (640 ml) | 5.5 hours | (II-3) 30.47 g (92.0%) | |
| 4 | Et (p) 22.42 g (X-4) | KOH (26.37 g) | n-BuOH (500 ml) | 2 days | (II-4) 13.88 g (83.7%) | |
| 5 | Ph (p) 18.65 g (X-5) | KOH (18.70 g) | n-BuOH (500 ml) | 15 hours | (II-5) 13.44 g (92.6%) | |

TABLE 15-continued

EtOCON⟨ring⟩(OH)—PhX → HN⟨ring⟩(OH)—PhX (X) → (II)

| Ref. Ex. No. | (X) X = | Base | solvent | reflux time | (II) g (Yield) m.p. (°C.) | IR |
|---|---|---|---|---|---|---|
| 6 | t-Bu (p) 46.67 g (X-6) | KOH (50.9 g) | n-BuOH (700 ml) | 5.5 hours | (II-6) 33.64 g (92.0%) | |
| 7 | CH$_3$ (p) 49.86 g (X-7) | KOH (61.8 g) | BuOH (700 ml) | 3.5 hours | (II-8) 33.20 g (92.0%) 135.5–137.5 | (Nujol) 3310, 1598, 1502, 1490 1445 |
| 8 | CH$_3$ (m) 21.2 g (X-8) | KOH (26.3 g) | EtOH (450 ml) | 6 days | (II-9) 10.25 g (66.6%) 154.5–155.5 | (Nujol) 3440, 3280, 3220, 3179 1606, 1590, 1490, 1475 |
| 9 | CH$_3$ (o) 14.7 g (X-89) | KOH (18.21 g) | EtOH (350 ml) | 5 days | (II-10) 7.90 g (74.0%) 141.0–142.0 | (Nujol) 3440, 3280, 3220, 3170 1608, 1590, 1490 |
| 10 | 3,4-diMe 20.2 g (X-10) | KOH (23.76 g) | EtOH (500 ml) | 10 days | (II-11) 13.97 g (93.5%) — | (Nujol) 3590, 3380, 1600, 1502 1467, 1448 |
| 11 | 3,4-diMe 22.7 g (X-11) | KOH (26.7 g) | EtOH (650 ml) | 12 days | (II-12) 14.85 g (88.4%) 182.0–183.0 | (Nujol) 3280, 3120(br), 1605 1415 |
| 12 | Cl (m) 22.2 g (X-12) | KOH (25.5 g) | EtOH (350 ml) | 2 days | (II-13) 13.68 g (82.6%) 100.0–101.0 | (Nujol) 3220, 3080, 1595, 1570 1432, 1408 |
| 13 | Cl (o) 9.2 g (X-13) | NaOH (3.89 g) | THF/H$_2$O (10 ml/20 ml) | 5 days | (II-14) 4.95 g (72.0%) 166.5–167.5 | (KBr) 3440, 3280, 3060, 1475 1442, 1430 |
| 14 | 3,5-diCl 25.11 g (X-14) | KOH (25.74 g) | EtOH (550 ml) | 11 days | (II-15) 15.5 g (79.8%) 213.0–214.0 | (Nujol) 3310, 3100, 3080, 1591 1568, 1450, 1425, 1410 |
| 15 | Br (p) 21.0 g (X-15) | KOH (20.87 g) | EtOH (500 ml) | 10 days | (II-16) 9.23 g (56.3%) 159.5–161.5 | (Nujol) 3280, 3050, 1588, 1492 1478, 1420 |
| 16 | F (p) 23.2 g (X-16) | KOH (17.36 g) | Dioxane/H$_2$O (170/70 ml) | 6 days | (II-17) 9.82 g (58.8%) — | (Nujol) 3280, 3130, 1602, 1512 1455 |
| 17 | CF$_3$ (m) Cl (p) 41.8 g (X-17) | KOH (42.7 g) | nBuOH (580 ml) | 2 hours | (II-18) 22.30 g (67.0%) 135.0–136.5 | (CHCl$_3$) 3595, 2950, 2850, 1607 1576, 1483 |
| 18 | *1 (X-18) 27.1 g | KOH (18.30 g) | EtOH (350 ml) | 2 days | (II-19) 11.88 g 149.5–150.0 | (Nujol) 3290, 1540, 1417 |
| 19 | *2 (X-19) 19.7 g | KOH (19.82 g) | nBuOH (500 ml) | 2 days | (II-20) 9.51 g (62.1%) 151.0–152.5 | (Nujol) 3280, 1640, 1540 |

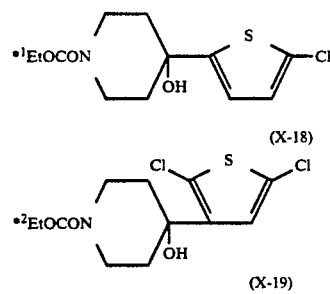

*1 EtOCON⟨ring⟩(OH)—S—Cl (X-18)

*2 EtOCON⟨ring⟩(OH)—(Cl)S(Cl) (X-19)

TABLE 16

| Compd. No. | m.p. (°C.) (solvent*) | Anal Calcd. (%) Found(%) | IR (cm$^{-1}$) | NMR (δ) |
|---|---|---|---|---|
| II-2 | 136.0–137.0 (ethyl acetate) | C$_{12}$H$_{14}$NOF$_3$: C, 58.83 (58.77) H, 5.74 (5.75) N, 5.73 (5.71) F, 23.13 (23.24) | (Nujol) 3290, 1619, 1443 1439, 1422, 1410 | (CD$_3$OD) 1.680(d-d, J$_1$=14Hz, J$_2$=2Hz, 2H); 2.004(t-d, J$_1$=14Hz, J$_2$=5Hz, 2H); 2.866 (d-d, J$_1$=13Hz, J$_2$=2Hz, 2H); 3.107(t-d, J$_1$=13Hz, J$_2$=2Hz, 2H); 7.625(d, J=9Hz, 2H); 7.698(d, J=9Hz, 2H) |
| II-3 | 178.5–179.5 (oxalate) (i-PrOH) | C$_{14}$H$_{21}$NO.C$_2$H$_2$O$_4$ C, 61.77 (62.12) H, 7.42 (7.49) N, 4.50 (4.53) | (CHCl$_3$) 3600, 3350(br). 1593, 1510, 1468 1422 | (CDCl$_3$) 0.933(t, J=7Hz, 3H); 1.620(sextet, J=8Hz, 2H); 1.876(d, J=14Hz, 2H); 2.330(t-d, J$_1$=14Hz, J$_2$=4Hz, 2H); 2.564(t, J=8Hz, 2H); 3.244 (d, J=12Hz, 2H); 3.367(t, J=12Hz, 2H); 7.164(d, J=*hz, 2H); 7.40 |

TABLE 16-continued

| Compd. No. | m.p. (°C.) (solvent*) | Anal Calcd. (%) Found(%) | IR (cm$^{-1}$) | NMR (δ) |
|---|---|---|---|---|
| II-4 | 119.0–120.0 (Et$_2$O—ethyl acetate) | C$_{13}$H$_{19}$NO<br>C, 75.97 (76.05)<br>H, 9.33 (9.33)<br>N, 6.78 (6.82) | (CHCl$_3$)<br>3600, 1510, 1469<br>1440, 1420, 1410<br>(sh) | (d, J=8Hz, 2H)<br>(CD$_3$OD)<br>1.204(t, J=8Hz, 3H); 1.676(d-d, J$_1$=14Hz, J$_2$=2Hz, 2H); 1.933<br>(t-d, J$_1$=14Hz, J$_2$=5Hz, 2H); 1.616(q, J=8Hz, 2H); 2.852(d-d, J$_1$=12<br>Hz, J$_2$=3Hz, 2H); 3.084(t-d, J$_1$=12Hz, J$_2$=3Hz, 2H); 7.156(d, J=8<br>Hz, 2H); 7.397(d, J=8Hz, 2H) |
| II-5 | 182.5–184.0 (MeOH—CH$_2$Cl$_2$) | C$_{17}$H$_{19}$NO.1/6H$_2$O<br>C, 79.84 (79.65)<br>H, 7.48 (7.60)<br>N, 5.44 (5.46) | (Nujol)<br>3320, 1595, 1581<br>1563, 1490, 1450 | (CDCl$_3$-CD$_3$OD=4/1)<br>1.804(d, J=12Hz, 2H); 2.052(t-d, J$_1$=14Hz, J$_2$=5Hz, 2H); 2.096(d-d,<br>J$_1$=13Hz, J$_2$=2Hz, 2H); 3.172(t-d, J$_2$=12Hz, J$_2$=3Hz, 2H); 7.29–<br>7.63(m, 9H) |
| II-6 | 185.0–186.0 (CHCl$_3$—MeOH) | C$_{15}$H$_{23}$NO.H$_2$O<br>C, 71.18 (71.67)<br>H, 9.86 (10.02)<br>N, 5.67 (5.57) | (Nujol)<br>3480(sh), 3390,<br>3320, 3290, 3090<br>1668, 1508, 1470 | (CD$_3$OD)<br>1.301(s, 9H); 1.684(d-d, J$_2$=14Hz, J$_2$=2Hz, 2H); 1.839(t-d, J$_1$=14<br>Hz, J$_2$=4Hz, 2H); 2.857(d-m, J$_1$=12Hz, 2H); 3.086(t-d, J$_1$=13Hz,<br>J$_2$=3Hz, 2H); 7.360(d, J=9Hz, 2H); 7.404(d, J=9Hz) |

*a solvent for recrystallization

EVALUATION OF BIOLOGICAL ACTIVITY

Experiment

After the decapitation of rats, the objective tissues were rapidly removed and each was weighed. Each tissue was homogenized with twenty-fold amount of ice-cold 50 mM Tris-HCl buffer (pH7.8), homogenized, and centrifuged at 40,000×g for 10 minutes. The supernatant was removed and pellets were then resuspended in the buffer and recentrifuged. The procedure is repeated 3 times. Then these obtained samples were freeze-dried in liquid nitrogen and preserved at −80° C. On the test day, the sample was thawed at room temperature and centrifuged at 40,000×g for 10 minutes, the pellets were then suspended in an incubation buffer and used as the receptor preparation. The preparation was added to the mixture containing the labelled ligand and the test drug, and filtered through Whatman GF/C filters and washed to terminate the reaction. Radioactivity on the filters was determined by a liquid scintillation counter and Ki value was calculated.

1. σ receptor

Sigma receptor binding was initiated by the addition of the receptor preparation (cortex tissue, 0.7 mg protein/ml) to a mixture containing 5 nM of [$^3$H]3PPP [3-hydroxyphenyl-N-(1-propyl)piperidine] and the test compound dissolved in 50 mM Tris-HCl buffer (pH 7.8). Incubation was carried out at 25° C. for 90 minutes. Specific sigma receptor binding was defined as the difference in amount of [$^3$H]3PPP bound to the tissue in the presence or the absence of 10 μM haloperidol.

2. DA2 receptor

DA2 receptor binding was initiated by the addition of the receptor preparation (striatal tissue, 0.3 mg protein/ml) to a mixture containing 0.2 nM of [$^3$H]spiroperidol and the test compound dissolved in 50 mM Tris-HCl buffer containing 100 mM-NaCl and 5 mM-KCl (pH 7.4). Incubation was carried out at 37° C. for 10 minutes. Specific DA2 receptor binding was defined as the difference in amount of [$^3$H]spiroperidol bound to the tissue in the presence or the absence of 10 μM haloperidol.

3. 5HT2 receptor

5HT2 receptor binding was initiated by the addition of the receptor preparation (cortex tissue, 0.5 mg protein/ml) to a mixture containing 1 nM of [$^3$H]spiroperidol and the test compound dissolved in 50 mM Tris-HCl buffer (pH 7.4). Incubation was carried out at 37° C. for 15 minutes. Specific 5HT2 receptor binding was defined as the difference in amount of [$^3$H]spiroperidol bound to the tissue in the presence or the absence of 1 mM serotonin.

4. PCP receptor

PCP receptor binding was initiated by the addition of the receptor preparation (cortex tissue, 0.2 mg protein/ml) to a mixture containing 5 mM of [$^3$H]TCP and the test compound dissolved in 5 mM Tris-HCl buffer (pH 7.8). Incubation was carried out at 25° C. for 30 minutes. Specific PCP receptor binding was defined as the difference in amount of [$^3$H]TCP bound to the tissue in the presence or the absence of 10 μM PCP.

The test results are shown in Table 17.

TABLE 17

| Test compound | Ki (μM) | | | |
|---|---|---|---|---|
| | PCP | σ | DA2 | 5-HT2 |
| Ia-2 | 31 | 0.0041 | 4.7 | 0.55 |
| Ia-3 | 16 | 0.0095 | 4.0 | 1.70 |
| Ia-6 | 49 | 0.0027 | 2.2 | 2.50 |
| Ia-8 | >62 | 0.0013 | 1.20 | 2.90 |
| Ia-9 | 33 | 0.0061 | 1.60 | 1.20 |
| Ia-11 | 23 | 0.0026 | 4.50 | 4.40 |
| Ia-13 | 26 | 0.0022 | 0.32 | 0.77 |
| Ia-24 | 32 | 0.0058 | 1.10 | 0.38 |
| Ia-30 | >63 | 0.0013 | 2.00 | 3.70 |
| Ia-35 | 18 | 0.0018 | 4.60 | 3.20 |
| Ia-56 | 44 | 0.0065 | 4.50 | 8.90 |
| Ia-57 | 44 | 0.0063 | 2.40 | 0.14 |
| Ia-94 | 27 | 0.0013 | 1.40 | 1.90 |
| Ia-101 | >63 | 0.00031 | 1.80 | 7.70 |
| Ia-102 | >71 | 0.00071 | 3.20 | 5.70 |
| Ia-111 | >63 | 0.0029 | 0.63 | 0.39 |
| Ia-112 | >63 | 0.0025 | >21 | 2.60 |

From the above, the compound of the present invention has low affinity to DA2 receptor and high affinity to σ receptor, and has useful activity as psychotropic agents.

What we claim is:

1. A compound of the formula:

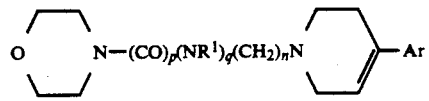

wherein
Ar is phenyl or thienyl which may have identically or differently one or two substituents selected from the group consisting of lower alkyl, lower alkoxy, halogen, substituted or unsubstituted phenyl, trifluoromethyl and hydroxy;

R$^1$ is hydrogen or lower alkyl;

the morpholino group may have identically or differently 1 to 3 substituents selected from the group consisting of lower alkyl, halogen, oxo pyrimidine and phenyl, which phenyl may be substituted by hydroxy, lower alkyl, lower alkoxy or halogen;

n is an integer of from 2 to 6;

p and q each is an integer of 0 or 1, excluding the case where p is 0 when q is 1;

or a pharmaceutically acceptable acid addition salt thereof.

2. A compound according to claim 1, wherein the substituted phenyl on the phenyl or thienyl for Ar is phenyl substituted by one or more substituents selected from the group consisting of hydroxy, lower alkyl, lower alkoxy and halogen.

* * * * *